(12) United States Patent
Op Den Camp et al.

(10) Patent No.: US 11,279,947 B2
(45) Date of Patent: Mar. 22, 2022

(54) METHOD FOR THE PRODUCTION OF HAPLOID AND SUBSEQUENT DOUBLED HAPLOID PLANTS

(71) Applicant: Keygene N.V., Wageningen (NL)

(72) Inventors: Rik Hubertus Martinus Op Den Camp, Wageningen (NL); Peter Johannes Van Dijk, Wageningen (NL); Anthony Gallard, Wageningen (NL)

(73) Assignee: KEYGENE N.V., Wageningen (NL)

( * ) Notice: Subject to any disclaimer, the term of this patent is extended or adjusted under 35 U.S.C. 154(b) by 347 days.

(21) Appl. No.: 15/763,701

(22) PCT Filed: Oct. 3, 2016

(86) PCT No.: PCT/NL2016/050682
§ 371 (c)(1),
(2) Date: Mar. 27, 2018

(87) PCT Pub. No.: WO2017/058022
PCT Pub. Date: Apr. 6, 2017

(65) Prior Publication Data
US 2019/0078117 A1 Mar. 14, 2019

(30) Foreign Application Priority Data
Oct. 2, 2015 (NL) ..................................... 2015552

(51) Int. Cl.
C12N 15/82 (2006.01)
C07K 14/415 (2006.01)
A01H 1/08 (2006.01)

(52) U.S. Cl.
CPC ........... *C12N 15/8287* (2013.01); *A01H 1/08* (2013.01); *C07K 14/415* (2013.01); *C12N 15/8201* (2013.01); *C12N 15/8241* (2013.01); *C12N 15/8261* (2013.01); *Y02A 40/146* (2018.01)

(58) Field of Classification Search
CPC .............................. A01H 1/08; C12N 15/8287
See application file for complete search history.

(56) References Cited

U.S. PATENT DOCUMENTS

2014/0090099 A1  3/2014 Chan

FOREIGN PATENT DOCUMENTS

WO  WO 2011/044132 A1  4/2011
WO  WO 2014/110274 A2  7/2014

OTHER PUBLICATIONS

NCBI Reference Sequence: XM_010320256.1; LOC543949 (LOC543949), transcript variant X1, mRNA PLN Nov. 19, 2014. (Year: 2014).*
UniProtKB A0A0D2RTA8 Gossypium raimondi, 638 a.a. CENP-C; entered Apr. 29, 2015. (Year: 2015).*
GenBank Accession XP_010318558 Version XP_010318558.1 centromere protein C isoform X1 [Solanum lycopersicum]PLN Aug. 8, 2018 . (Year: 2018).*
Talbert, P.B. et al. Journal of Biology (2004) vol. 13, No. 18; pp. 1-17Talbert, P.B. et al. Journal of Biology (2004) vol. 13, No. 18; pp. 1-17 (Year: 2004).*
NCBI Reference Sequence: XM_010320256.1; (LOC543949), transcript variant X1, MRNA Nov. 19, 2014 (Year: 2014).*
NCBI Reference Sequence: XM_004235650; (LOC543949), transcript variant X2, mRNA, Nov. 19, 2014. (Year: 2014).*
Burgos-Rivera et al., "An *Arabidopsis* tissue-specific RNAi method for studying genes essential to mitosis", PLOS One, Dec. 2012, vol. 7, No. 12, p. e51388 (7 pages).
Database Protein [Online], retrieved from NCBI Database accession No. XP_010318558 glutamin introduced between positions 552 and 553 of SEQ ID No. 4, Nov. 19, 2014, abstract.
Ravi et al., "Haploid plants produced by centromere-mediated genome elimination", Nature, Mar. 2010, vol. 464, pp. 615-620.
Ravi et al., "A haploid genetics toolbox for *Arabidopsis thaliana*". Nature Communications, Oct. 2014, pp. 1-8.
Talbert et al., "Adaptive evolution of centromere proteins in plants and animals", Journal of Biology, BioMed Central, Aug. 2004, vol. 3, No. 18, 18 pages.
International Search Report issued in International Patent Application No. PCT/NL2016/050682, dated Jan. 13, 2017.

\* cited by examiner

*Primary Examiner* — Russell Kallis
(74) *Attorney, Agent, or Firm* — Sunit Talapatra; Foley & Lardner LLP

(57) ABSTRACT

It was found that plants comprising modified CENPC protein comprising one or more active mutations which affect the functioning of CENPC protein yet allow plants expressing said modified CENPC protein to be viable, are able to induce haploid offspring after a cross to or with a wild type plant comprising a endogenous CENPC protein. The invention relates to generation of haploid and doubled haploid plants.

29 Claims, 1 Drawing Sheet
Specification includes a Sequence Listing.

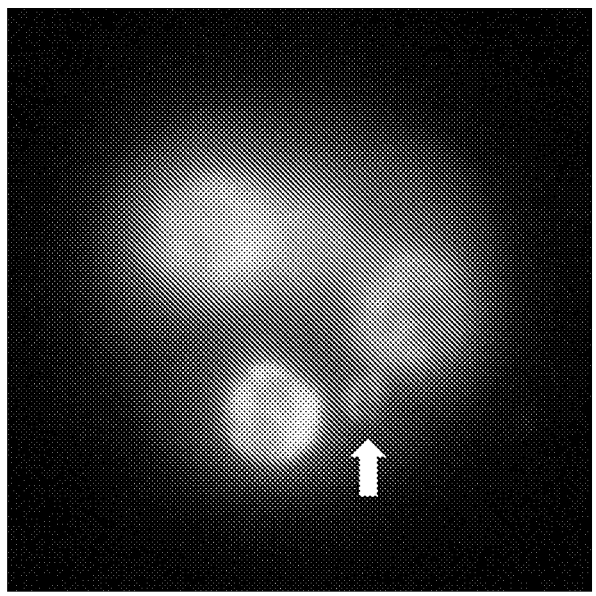

METHOD FOR THE PRODUCTION OF HAPLOID AND SUBSEQUENT DOUBLED HAPLOID PLANTS

CROSS-REFERENCE TO RELATED APPLICATIONS

This application is a national phase entry of International Patent Application No. PCT/NL2016/050682, filed Oct. 3, 2016, published on Apr. 6, 2017 as WO 2017/058022 A1, which claims priority to Netherlands Patent Application No. 2015552, filed Oct. 2, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. The ASCII copy, created on Sep. 28, 2018, 085342-2300_SL.txt and is 112,555 bytes.

FIELD OF THE INVENTION

The disclosure relates to the field of agriculture. In particular, the disclosure relates to the production of haploid and subsequent doubled haploid plants.

BACKGROUND OF THE INVENTION

A high degree of heterozygosity in breeding material can make plant breeding and selection for beneficial traits a very time consuming process. Extensive population screening, even with the latest molecular breeding tools, is both laborious and costly.

The creation of haploid plants followed by chemical or spontaneous genome doubling is an efficient way to solve the problem of high heterozygosity. Such doubled haploids bypass at least 7 generations of selfing otherwise needed to reduce the heterozygosity to an acceptable level. Haploid plants can be produced in some crops by microspore culture. However, this is costly and time-consuming. More importantly, in many crops microspore culture methods do not work. In some crop species, (doubled) haploid plants can be obtained by parthenogenesis of the egg cell or by elimination of one of the parental genomes. However, these methods are also restricted to a few selected crops and the production rates of doubled haploid plants are low.

WO2011/044132 discloses methods of producing haploid plants. One of the methods employed is inactivating or knocking out CenH3 protein. This was done by adding an N-terminal GFP to the CenH3 protein, thereby creating GFP-CenH3. This is also called a "tailswap". The tailswap was sufficient to induce uni-parental genome elimination upon a cross to a plant without such modified N-terminal part of the CenH3 protein. The uni-parental genome elimination resulted in the production of a haploid plant. So far this process has only been demonstrated in the model plant *Arabidopsis thaliana* and not in crop plants. Additionally, when another artificial construct, which consisted of a different trans-genetically modified N-terminal part of the CenH3 protein, was introduced in a plant with a genetic background lacking the endogenous CenH3, it appeared that this did not resulted in uni-parental genome elimination and subsequent production of a haploid plant (WO 2014/110274). Therefore it remains elusive which modifications of the CenH3 protein are sufficient for uni-parental genome elimination.

Thus, there remains a need in the art for methods that allow efficient generation of haploid plants which can subsequently be doubled, to produce doubled haploid plants. With doubled haploid production systems, homozygosity is achieved in one generation.

SUMMARY OF THE INVENTION

The present inventors have now found that plants with modified CENPC protein, due to unique single nucleotide polymorphisms, are both able to induce haploid offspring after a cross to or with a wild type plant lacking these particular unique single nucleotide polymorphisms. One polymorphism comprised four nucleotide changes in a single plant, resulting in; (1) a G to T nucleotide modification of a splice acceptor site of the CENPC genomic DNA sequence which leads to the insertion of an H amino acid in the CENPC protein, (2) a D to K amino acid modification in the CENPC protein and (3) a N to Y amino acid modification in the CENPC protein. The other unique single nucleotide polymorphism resulted in a M to V amino acid modification in the CENPC protein. Reciprocal crosses with control plants, never yielded any haploid offspring.

The invention relates to a CENPC protein of plant origin comprising one or more active mutations. The one or more active mutations may be present in a protein comprising the amino acid sequence of any of SEQ ID NO: 2, 3, 4 or 15-19. The one or more active mutations may be made in a protein comprising the amino acid sequence of any of SEQ ID NO:2, 3, 4 or 15-19, or a variant thereof having at least 70%, more preferably at least 80%, even more preferably at least 90%, yet even more preferably at least 95%, most preferably at least 98% or 99% sequence identity to the amino acid sequence of any of SEQ ID NO:2, 3, 4 or 15-19.

In an embodiment, the one or more active mutations are present in a doubled haploid inducer domain represented by the amino acid sequences as depicted in any of SEQ ID NO: 5 or 6.

Said one or more active mutations may be chosen from the group consisting of a mutation between amino acid residues at position 552 and 553, a mutation of an amino acid residue at position 554, a mutation of an amino acid residue at position 555 and a mutation of an amino acid residue at position 556, or any combination thereof, in the amino acid sequence of any of SEQ ID NO: 3 or 4; or of a mutation between amino acid residues at position 555 and 556, a mutation of an amino acid residue at position 557, a mutation of an amino acid residue at position 558 and a mutation of an amino acid residue at position 559, or any combination thereof, in the amino acid sequence of SEQ ID NO: 2.

In an embodiment, the amino acid that is mutated at position 554 of the amino acid sequence of any of SEQ ID NO: 3 or 4, or at position 557 in the amino acid sequence of SEQ ID NO: 2, is aspartic acid and/or the amino acid that is changed at position 555 of the amino acid sequence of any of SEQ ID NO: 3 or 4, or at position 558 in the amino acid sequence of SEQ ID NO: 2, is asparagine and/or the amino acid that is changed at position 556 of the amino acid sequence of any of SEQ ID NO: 3 or 4, or at position 559 in the amino acid sequence of SEQ ID NO: 2, is methionine.

In an embodiment, the amino acid at position 554 of the amino acid sequence of any of SEQ ID NO: 3 or 4, or at position 557 in the amino acid sequence of SEQ ID NO: 2, is changed into a positively charged amino acid residue, preferably into lysine, and/or the amino acid at position 555 of the amino acid sequence of any of SEQ ID NO: 3 or 4, or at position 558 in the amino acid sequence of SEQ ID NO: 2, is changed into a tyrosine and/or the amino acid at position 556 of the amino acid sequence of any of SEQ ID NO: 3 or 4, or at position 557 in the amino acid sequence of SEQ ID NO: 2, is changed into valine, and/or wherein a positively charged residue, preferably histidine, is inserted between amino acid residues 552 and 553 of the amino acid sequence of any of SEQ ID NO: 3 or 4, or between amino acid residues 555 and 556 in the amino acid sequence of SEQ ID NO: 2.

In an embodiment, a histidine is inserted between amino acid residues 552 and 553 of the amino acid sequence of any of SEQ ID NO: 3 or 4, or between amino acid residues 555 and 556 in the amino acid sequence of SEQ ID NO: 2, and/or an aspartic acid at position 554 of the amino acid sequence of any of SEQ ID NO: 3 or 4, or at position 557 in the amino acid sequence of SEQ ID NO: 2, is changed into a lysine and/or an asparagine at position 555 of the amino acid sequence of any of SEQ ID NO: 3 or 4, or at position 558 in the amino acid sequence of SEQ ID NO: 2, is changed into a tyrosine.

In an embodiment, said protein comprises the amino acid sequence of SEQ ID NO:8 or of SEQ ID NO:10.

Said protein may be encoded by a polynucleotide comprising the nucleic acid sequence of any of SEQ ID NO:7 or 12, or said protein may be encoded by a polynucleotide comprising the nucleic acid sequence of any of SEQ ID NO:9 or 13.

In an embodiment, said protein is encoded by a CENPC protein-encoding polynucleotide having an active mutation, which, when present in a plant in the absence of its endogenous CENPC protein-encoding polynucleotide and/or endogenous CENPC protein, allows said plant to be viable, and allows generation of some haploid progeny, or progeny with aberrant ploidy, when said plant is crossed with a wild-type plant.

Preferably, at least 0.1, 0.5, 1 or 5% of the progeny generated is haploid or has an aberrant ploidy.

Said protein may be derived from an endogenous CENPC protein by introducing mutations in the polynucleotide encoding said endogenous CENPC protein using targeted nucleotide exchange or by applying an endonuclease.

In an embodiment, the one or more active mutations are not present in a protein domain comprising the amino acid sequence depicted in SEQ ID NO:1.

In a further aspect, the present invention pertains to a polynucleotide encoding the CENPC protein as taught herein.

The invention also relates to a polynucleotide comprising the nucleic acid sequence of any of SEQ ID NO:11 or 14, or a variant thereof having at least 70%, more preferably at least 80%, even more preferably at least 90%, yet even more preferably at least 95%, most preferably at least 98% or 99% sequence identity to the amino acid sequence of any of SEQ ID NO:11 or 14, but in which one or more nucleotides at positions 2449-2450 and/or 2454-2462 of the nucleic acid sequence of SEQ ID NO:11 or at positions 1660-1668 in SEQ ID NO:14 are modified such that the nucleic acid encodes a CENPC protein in which the amino acid sequence of SEQ ID NO:3 has an altered residue at position 554 and/or at position 555 and/or at position 556, and/or has an insertion of an amino acid residue, such as a histidine between the amino acid residues 552 and 553 of the amino acid sequence of SEQ ID NO:3.

Additionally, a polynucleotide comprising the nucleic acid sequence of any of SEQ ID NO:7 or 12 is taught herein.

Also, a polynucleotide comprising the nucleic acid sequence of any of SEQ ID NO: 9 or 13 is taught herein.

The polynucleotide taught herein may be isolated.

The invention is further concerned with a chimeric gene comprising the polynucleotide as taught herein, a vector comprising the polynucleotide or the chimeric gene as taught herein, and a host cell comprising a polynucleotide as taught herein, a chimeric gene as taught herein, or a vector as taught herein. The host cell may be a plant cell, preferably a tomato plant cell.

The invention also provides a plant comprising a polynucleotide as taught herein, a chimeric gene as taught herein, or a vector as taught herein.

In an embodiment, the endogenous CENPC protein is not expressed in said plant.

The plant may be a *Solanum* plant, preferably a *Solanum lycopersicum* plant.

The invention further relates to a method for making a plant as taught herein, said method comprising the steps of:
 a) modifying an endogenous plant CENPC protein-encoding polynucleotide within a plant cell to obtain an plant CENPC protein-encoding polynucleotide having an active mutation;
 b) selecting a plant cell comprising the plant CENPC protein-encoding polynucleotide having an active mutation; and
 c) optionally, regenerating a plant from said plant cell.

Also, the invention relates to a method for making a plant as taught herein, said method comprising the steps of:
 a) transforming a plant cell with a polynucleotide as taught herein, a chimeric gene as taught herein, or a vector as taught herein;
 b) selecting a plant cell comprising said polynucleotide, chimeric gene or vector; and
 c) optionally, regenerating a plant from said plant cell.

Said method mat further comprise the step of modifying said plant cell to prevent expression of endogenous CENPC protein.

An endogenous plant CENPC protein-encoding polynucleotide within said plant cell may be modified to prevent expression of endogenous CENPC protein.

The invention further pertains to a method of generating a haploid plant, or a plant with aberrant ploidy, said method comprising the steps of:
 a) crossing a plant expressing an endogenous plant CENPC protein to the plant as taught herein, wherein the plant as taught herein does not express an endogenous CENPC protein at least in its reproductive parts and/or during embryonic development;
 b) harvesting seed;
 c) growing at least one seedling, plantlet or plant from said seed; and
 d) selecting a haploid seedling, plantlet or plant; a seedling, plantlet or plant with aberrant ploidy; or a doubled haploid seedling, plantlet or plant.

The disclosure further teaches a method of generating a doubled haploid plant, said method comprising the steps of converting the haploid plant obtained in step d) into a doubled haploid plant.

The conversion may be performed by treatment with colchicine.

In an embodiment, said plant expressing an endogenous plant CENPC protein is an F1 plant.

The plant expressing an endogenous CENPC protein may be a pollen parent of the cross, or may be an ovule parent of the cross.

In an embodiment, the cross is performed at a temperature in the range of about 24 to about 30° C.

In an embodiment, the methods taught herein do not comprise sexually crossing the whole genomes of said plants.

The polynucleotide taught herein may be used for producing a haploid inducer line.

A *Solanum lycopersicum* plant comprising the polynucleotide as taught herein, a chimeric gene as taught herein, or a vector as taught herein, is also provided.

Additionally, a *Solanum lycopersicum* plant comprising a polynucleotide encoding a protein comprising the amino acid sequence of any SEQ ID NO:8 or 10 is provided.

Further, a *Solanum lycopersicum* plant comprising a polynucleotide comprising the nucleic acid sequence of any of SEQ ID NO:7, 12, 9, or 13 is taught herein.

The invention further provides a *Solanum lycopersicum* plant comprising a polynucleotide that encodes a CENPC protein as taught herein.

A *Solanum lycopersicum* plant comprising one or more active mutations in the polypeptide comprising the amino acid sequence of SEQ ID NO:4, is also provided.

The *Solanum lycopersicum* plants as taught herein may be used for producing a haploid *Solanum lycopersicum* plant, and/or for producing a doubled haploid *Solanum lycopersicum* plant.

In an embodiment, the *Solanum lycopersicum* plant as taught herein does not express an endogenous CENPC protein at least in its reproductive parts and/or during embryonic development.

In a final aspect, the present invention is concerned with a method of generating a haploid or doubled haploid plant, said method comprising identifying a plant expressing an endogenous CENPC protein and a plant as taught herein, wherein the plant as taught herein does not express an endogenous CENPC protein.

In an embodiment, said method does not comprise sexually crossing the whole genomes of said plants.

DEFINITIONS

The abbreviation "CENPC" or "CENP-C" denotes Centromere Protein C. Centromere Protein C is characterized by a CENPC motif, which is a protein sequence defining a CENPC protein from any organism. The CENPC motif is highly conserved among animals, yeast and plants (Talbert et al 2004 Journal of biology 3(4), 18). The consensus CENPC motif from human; mouse; cow; chicken; Caenorhabditis elegans; budding yeast; *Schizosaccharomyces pombe*; *Physcomitrella patens*; maize; rice; *Arabidopsis thaliana*; black cottonwood, soybean and tomato is provided as SEQ ID NO:1.

A "mutation" is a permanent change of the nucleotide sequence of the genome of an organism, virus, or extrachromosomal DNA or other genetic elements. Mutations result from damage to DNA which is not repaired or to RNA genomes (typically caused by radiation or chemical mutagens), errors in the process of replication, or from the insertion or deletion of segments of DNA by mobile genetic elements. Mutations may or may not produce discernible changes in the observable characteristics (phenotype) of an organism. A mutation can result in several different types of change in sequences. Mutations in genes can either have no effect, alter the product of a gene, or prevent the gene from functioning properly or completely. Mutations can also occur in nongenic regions.

An "CENPC-encoding polynucleotide having an active mutation" refers to a non-endogenous, mutated CENPC-encoding polynucleotide that encodes a CENPC protein having an active mutation, which, when present in a plant in the absence of its endogenous CENPC-encoding polynucleotide and/or endogenous CENPC protein, allows said plant to be viable, and allows generation of some haploid progeny, or progeny with aberrant ploidy, when said plant is crossed with a wild-type plant, preferably a wild-type plant of the same species. The plant comprising a CENPC-encoding polynucleotide having an active mutation may be referred to as a "modified plant". The percentage of haploid progeny or progeny with aberrant ploidy that is generated upon crossing with a wild-type plant can, for instance, be at least 0.1, 0.5, 1, 5, 10, 20% or more. A mutation that causes a transition from the endogenous CENPC-encoding polynucleotide to a CENPC-encoding polynucleotide having an active mutation is herein referred to as an "active mutation". An active mutation in a CENPC protein context may result, among other things, in reduced centromere loading, a less functional CENPC protein and/or a reduced functionality in the separation of chromosomes during cell division. An active mutation may be introduced into the CENPC-encoding polynucleotide by any of several methods well-known to the skilled person, for example, by random mutagenesis, such as induced by treatment of seeds or plant cells with chemicals or radiation, targeted mutagenesis, the application of endonucleases, by generation of partial or complete protein domain deletions, or by fusion with heterologous sequences. Alternatively, several of these technologies may be used to introduce one or more active mutations.

A "CENPC protein having an active mutation" is encoded by a CENPC-encoding polynucleotide having an active mutation. The endogenous CENPC-encoding polynucleotide encodes the endogenous CENPC protein.

A plant may be made to lack the endogenous CENPC-encoding polynucleotide by knocking out or inactivating said endogenous CENPC-encoding polynucleotide. Alternatively, said endogenous CENPC-encoding polynucleotide may be modified to encode an inactive or non-functional CENPC protein.

The modified plant comprising the CENPC-encoding polynucleotide having an active mutation taught herein may be crossed to a wild-type plant either as a pollen parent or as an ovule parent. In an embodiment, a CENPC protein having an active mutation may comprise 1, 2, 3, 4, 5, 6, 7, 8, 9, 10, 12, 15, 20 or more amino acid changes relative to the endogenous CENPC protein. In an embodiment, a CENPC-encoding polynucleotide having an active mutation has 70, 75, 80, 85, 90, 95, 96, 97, 98, 99, 99.5% sequence identity to the endogenous CENPC-encoding polynucleotide, preferably over the full length.

The skilled person would readily be able to ascertain whether or not a modified plant as taught herein comprises an active mutation. For example, the skilled person may make use of predictive tools such as SIFT (Kumar P, Henikoff S, Ng P C. (2009) Predicting the effects of coding non-synonymous variants on protein function using the SIFT algorithm. Nat Protoc; 4(7):1073-81. doi:10.1038/nprot.2009.86) to propose such active mutation. The active mutation may then be made in a plant, and expression of endogenous CENPC protein in said plant should be knocked out. The plant may be considered to comprise an active mutation when the percentage of haploid progeny or progeny with aberrant ploidy that is generated upon crossing with a wild-type plant is at least 0.1, 0.5, 1, 5, 10, 20% or more.

Crossing a plant that lacks an endogenous CENPC-encoding polynucleotide or that lacks expression of endogenous CENPC protein and that expresses a CENPC protein having an active mutation either as a pollen or as an ovule parent with a plant that expresses an endogenous CENPC protein results in a certain percentage (for instance at least 0.1, 0.5, 1, 5, 10, 20% or more) of progeny that is haploid or shows aberrant ploidy. Such a plant comprises only chromosomes of the parent that expresses the endogenous CENPC protein, and no chromosomes of the plant expressing the CENPC protein having an active mutation.

Two plants that are crossed have to be sexually compatible. They may be of the same genus or of the same species.

The term "endogenous" as used in the context of the present invention in combination with protein or gene means that said protein or gene originates from the plant in which it is still contained. Often an endogenous gene will be present in its normal genetic context in the plant.

The term "haploid inducer line" used in the context of the present disclosure refers to a plant line which differs in at least one single nucleotide polymorphism from the non-inducer line. When an haploid inducer line is crossed, either used as female or as pollen donor, it results in uni-parental genome elimination of the haploid inducer line's genome.

The term "uni-parental genome elimination" as used herein refers to the effect of losing all the genetic information, meaning all chromosomes, of one parent after a cross irrespective of the direction of the cross. This occurs in such way that the offspring of such cross will only contain chromosomes of the non-eliminated parental genome. The genome which is eliminated always has the origin in the haploid inducer parent.

A "doubled haploid" is a genotype formed when haploid cells undergo chromosome doubling. It may be produced by induced or spontaneous chromosome doubling from haploid cells. For diploid plants, the haploid cells are monoploid, and the term "doubled monoploid" may also be used for the doubled haploids.

The "Solanaceae CENPC DH-inducer domain protein sequence" defines a specific region of the CENPC protein from a species belonging to the Solanaceae plant family that is highly conserved among Solanaceae species. It represents the consensus protein sequence of the CENPC DH-inducer domain of *Solanum lycopersicum, Nicotiana tabacum, Nicotiana tomentosiformis, Capsicum annuum, Solanum tuberosum* and *Solanum frutescence*, and its amino acid sequence is shown in SEQ ID NO:5.

The "*Solanum* CENPC DH-inducer domain protein sequence" defines a specific region of the CENPC protein from species belonging to the *Solanum* plant genus. It is highly conserved among *Solanum* species. The amino acid sequence of the consensus protein sequence of the CENPC DH-inducer domain of *Solanum lycopersicum, Solanum pimpinellifolium, Solanum peruvianum, Solanum chiemliewskii, Solanum cheesmaniae, Solanum neorickii, Solanum Arcanum, Solanum peruvianum, Solanum huayiasense, Solanum chilense, Solanum habrochaites, Solanum pennellii, Solanum galapagense* and *Solanum tuberosum* is shown as SEQ ID NO:6.

The term "indeterminate" as used herein refers to the type of growth habit of tomato plants, which is commonly classified as determinate or indeterminate. This classification preferably depends on the capacity of the shoot system for continued sympodial growth. The terms are used in their art-recognized meaning.

The terms "polynucleotide" and "nucleic acid" are used interchangeably herein.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc.

A "host cell" or a "recombinant host cell" or "transformed cell" are terms referring to a new individual cell (or organism) arising as a result of introduction of at least one nucleic acid molecule, especially comprising a chimeric gene encoding a desired protein. The host cell is preferably a plant cell or a bacterial cell. The host cell may contain the nucleic acid molecule or chimeric gene as an extra-chromosomally (episomal) replicating molecule, or more preferably, comprises the nucleic acid molecule or chimeric gene integrated in the nuclear or plastid genome of the host cell.

As used herein, the term "plant" includes plant cells, plant tissues or organs, plant protoplasts, plant cell tissue cultures from which plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

In this document and in its claims, the verb "to comprise" and its conjugations is used in its non-limiting sense to mean that items following the word are included, but items not specifically mentioned are not excluded. It encompasses the verbs "to essentially consist of" and "to consist of".

In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

DETAILED DESCRIPTION OF THE INVENTION

The present inventor found that elimination of an endogenous CENPC in combination with expression of a non-endogenous CENPC protein having an active mutation in a plant resulted in a plant that has useful properties for breeding. It was found that such plant can function as a haploid inducer line. When such haploid inducer line is crossed with a plant having an endogenous CENPC protein, a portion of the resulting progeny lacks the chromosomes derived from the hapoid inducer line, thereby allowing the production of haploid progeny or progeny with aberrant ploidy. Haploid plants are useful for improving breeding.

Equal distribution of DNA in mitosis requires the assembly of a large proteinaceous ensemble onto the centromeric DNA, called the kinetochore. Kinetochores are multisubunit complexes that assemble on centromeres to bind spindle microtubules and promote faithful chromosome segregation during cell division. A 16-subunit complex named the constitutive centromere-associated network (CCAN) creates the centromere-kinetochore interface. CENPC, a CCAN subunit, is crucial for kinetochore assembly because it links centromeres with the microtubule-binding interface of kinetochores. The exact role of CENPC in CCAN organization is not yet fully understood, but certain data point to CENPC as a blueprint for kinetochore assembly. When CENPC is depleted, the proper formation of both centromeres and kinetochores is prevented.

CENPC Proteins Having an Active Mutation

The present invention provides a CENPC protein having an active mutation. Such CENPC protein having an active mutation comprises one or more active mutations. When a plant that expresses such CENPC protein having an active mutation and lacks expression of, or has suppressed expression of, endogenous CENPC protein, is crossed to a wild type plant expressing endogenous CENPC protein, haploid plants are formed at relatively high frequency. CENPC proteins having an active mutation can be created by a variety of means known to the skilled person. These include, without limitation, random mutagenesis, single or multiple amino acid targeted mutagenesis, generation of complete or partial protein domain deletions, fusion with heterologous amino acid sequences, and the like. Typically, the polynucleotide encoding endogenous CENPC protein will be knocked out or inactivated. Haploid plants are formed at a more than normal frequency, such as at least 0.1, 0.5, 1, 5, 10, 20% or more. CENPC proteins having an active mutation can, for example, be tested by recombinant expression of the CENPC protein having an active mutation in a plant lacking endogenous CENPC protein, crossing the transgenic plant to a plant expressing endogenous CENPC protein, and then screening for the production of haploid progeny.

Any number of mutations can be introduced into an endogenous CENPC protein to generate a CENPC protein having an active mutation. For example, the CENPC protein having an active mutation may be identical to the endogenous CENPC protein but for 1, 2, 3, 4, 5, 6, 7, 8, or more amino acids.

The active mutation preferably is not present in the CENPC motif.

The CENPC protein is preferably a plant CENPC protein. The plant may be any plant, but preferably belongs to the Solanaceae family, more preferably to the genus *Solanum*, even more preferably to the species *Solanum lycopersicum*.

In an embodiment, the one or more active mutations are made in the endogenous CENPC protein as represented by an amino acid sequence as shown in any of SEQ ID NO: 2, 3, 4, or 15-19, or a variant thereof having at least 70%, 75%, 80%, 85%, 90%, 91%, 92%, 93%, 94%, 95%, 96%, 97%, 98%, 99% or more, such as 100%, amino acid sequence identity to the amino acid sequence of any of SEQ ID NO: 2, 3, 4, or 15-19, preferably over the entire length. Amino acid sequence identity is determined by pairwise alignment using the Needleman and Wunsch algorithm and GAP default parameters as defined above.

The active mutation within the CENPC protein having an active mutation may be located throughout the protein. In an embodiment, the active mutation is located between amino acid residue Glu548 and Pro562 of the endogenous CENPC protein as represented by an amino acid sequence as shown in any of SEQ ID NO: 3 or 4, or a variant of the CENPC protein having an amino acid sequence as shown in SEQ ID NO: 3 or 4 as taught herein.

The active mutation within the CENPC protein having an active mutation may be located between amino acid residues Glu551 and His565 of SEQ ID NO:2, or a variant of the CENPC protein having an amino acid sequence as shown in SEQ ID NO: 2 as taught herein.

In an embodiment, one or more of the amino acid residues on positions corresponding to amino acid residues 552, 553, 554, 555, or 556 of the endogenous *Solanum lycopersicum* CENPC protein (the amino acid sequence of which is shown in SEQ ID NO:4) are mutated. For example, aspartic acid on position 554, asparagine on position 555, or the methionine on position 556 of SEQ ID NO:4, or a variant of the CENPC protein having an amino acid sequence as shown in SEQ ID NO: 4 as taught herein, or the corresponding amino acid residue in any of SEQ ID NO: 2 or 3, may be mutated.

In SEQ ID NO:2 or variants thereof as taught herein, Asp557 corresponds to Asp554 in the amino acid sequence of SEQ ID NO:4, Asn 558 corresponds to Asn555 in the amino acid sequence of SEQ ID NO:4, and Met559 corresponds to Met556 in the amino acid sequence of SEQ ID NO:4. In SEQ ID NO:3 or variants thereof as taught herein, Asp554 corresponds to Asp554 in the amino acid sequence of SEQ ID NO:4, Asn 555 corresponds to Asn555 in the amino acid sequence of SEQ ID NO:4, and Met556 corresponds to Met556 in the amino acid sequence of SEQ ID NO:4.

The amino acid residue on position 554 of the amino acid sequence of SEQ ID NO:4 or a variant thereof, or the amino acid residue corresponding to this amino acid residue in any of SEQ ID NO: 2 or 3 or variants thereof as taught herein, e.g., aspartic acid, may, for example, be mutated into a positively charged amino acid residue such as histidine, lysine, or arginine, preferably into lysine. The amino acid residue on position 555 of the amino acid sequence of SEQ ID NO:4 or a variant thereof, or the amino acid residue corresponding to this amino acid residue in any of SEQ ID NO: 2 or 3 or variants thereof as taught herein, e.g., asparagine, may, for example, be mutated into an aromatic amino acid residue such as phenylalanine, tryptophan, or tyrosine, preferably into tyrosine. The amino acid residue at position 556 of the amino acid sequence of SEQ ID NO:4 or a variant thereof, or the amino acid residue corresponding to this amino acid residue in any of SEQ ID NO: 2 or 3 or variant thereof as taught herein, e.g., methionine, may, for example, be mutated into an amino acid residue with a small side chain such as glycine, serine, cysteine, alanine, threonine, or valine, preferably into valine.

In an embodiment, an amino acid residue may be inserted in the domain between amino acid residues Glu548 and Pro562, particularly between amino acid residues 552 and 553, of the endogenous CENPC protein as represented by an amino acid sequence as shown in any of SEQ ID NO: 3 or 4, or a variant thereof as taught herein, or between amino acid residues Glu561 and Pro565 of the CENPC protein as represented by an amino acid sequence as shown in SEQ ID NO:2, or a variant thereof as taught herein.

For example, a positively charged residue such as a His residue may be inserted between amino acid residues 552 and 553 of the amino acid sequence as shown in SEQ ID NO: 3 or 4, or a variant thereof as taught herein, or between amino acid residues 555 and 556 of the amino acid sequence depicted in SEQ ID NO:2, or a variant thereof as taught herein.

In an embodiment, the amino acid residue inserted between amino acid residues 552 and 553 of the amino acid sequence as shown in SEQ ID NO: 4 is not a glutamine residue.

In an embodiment, the active mutations that are made in the endogenous CENPC protein having the amino acid sequence of any of SEQ ID NO:3 or 4, or a variant thereof, to yield a CENPC protein having an active mutation are selected from the group consisting of insertion of His between amino acid residues 552 and 553 (552_553insH), and the mutations D554K, N555Y, M556V, or any combinations thereof, such as 552_553insH/D554K/N555Y/M556V, 552_553insH/554K/N555Y, 552_553insH/D554K/M556V, 552_553insH/N555Y/M556V, 552_553insH/D554K, 552_553insH/N555Y, 552_553insH/M556V, D554K/N555Y, D554K/M556V, and N555Y/M556V, or the corresponding mutations in SEQ ID NO:2, or a variant thereof (D557K, N558Y, M559V and 555_556insH).

CENPC-Encoding Polynucleotides Having an Active Mutation, Chimeric Genes, Vectors, Host Cells Polynucleotides having nucleic acid sequences, such as cDNA, genomic DNA and RNA molecules, encoding any of the above proteins are also provided. Due to the degeneracy of the genetic code a variety of nucleic acid sequences may encode the same amino acid sequence. Any polynucleotides encoding CENPC proteins or variants thereof are herein referred to as "CENPC-encoding polynucleotides". The polynucleotides provided include naturally occurring, artificial or synthetic nucleic acid sequences. It is understood that when sequences are depicted as DNA sequences while RNA is referred to, the actual base sequence of the RNA molecule is identical with the difference that thymine (T) is replaced by uracil (U).

The present invention further relates to a polynucleotide encoding a CENPC protein having an active mutation as taught herein. Said polynucleotide may be a synthetic, recombinant and/or isolated polynucleotide. In an embodiment, said polynucleotide is derived from an endogenous CENPC-encoding polynucleotide that comprises the nucleic acid sequence of SEQ ID NO:11 or 14 or a variant thereof having at least 70%, preferably at least 75%, such as 80%, 85%, 90%, 95%, more preferably at least 97%, 98%, or 99% sequence identity to the nucleic acid sequence of SEQ ID NO:11 or 14, preferably over the full length, and which shares the endogenous CENPC activity of the polypeptide comprising the amino acid sequence of SEQ ID NO:4. In contrast, the CENPC-encoding polynucleotide having an active mutation taught herein comprises one or more active mutations that reduce(s) or eliminate(s) endogenous CENPC activity to less than 90, 80, 70, 60, 50, 40, 30, 20, 10% of CENPC activity of the endogenous CENPC protein from which it is derived. CENPC activity may be measured in vitro by measuring centromeric localization during separation of the chromosomes, for example, using a GFP fusion, where the level of fluorescence is a measure of CENPC activity. Alternatively, yeast-2-hybrid interactions may be measured in vitro using all known proteins and/or centromeric DNA that interact with CENPC protein. If the interaction is impaired, functionality of CENPC is impaired.

In an embodiment, one or more nucleotides at positions 1660-1668 of the polynucleotide comprising the nucleic acid sequence of SEQ ID NO:14 are modified such that the polynucleotide encodes a CENPC protein in which the amino acid sequence of SEQ ID NO:4 has an altered amino acid residue at position 554 and/or at position 555 and/or at position 556.

In an embodiment, one or more nucleotides at positions 2449-2450 and/or 2454-2462 of the polynucleotide comprising the nucleic acid sequence of SEQ ID NO:11 are modified such that the polynucleotide encodes a CENPC protein in which the amino acid sequence of SEQ ID NO:4 has an amino acid residue inserted between residues 552 and 553, and/or has an altered amino acid residue at position 554 and/or at position 555 and/or at position 556.

For example, aspartic acid on position 554, asparagine on position 555, or the methionine on position 556 of any of SEQ ID NO:4, or a variant of the CENPC protein having an amino acid sequence as shown in SEQ ID NO: 4 as taught herein, or the corresponding amino acid residue in any of SEQ ID NO: 2 or 3, or variants thereof as taught herein, may be mutated. The amino acid residue on position 554 of the amino acid sequence of SEQ ID NO:4 or a variant thereof, or the amino acid residue corresponding to this amino acid residue in any of SEQ ID NO: 2 or 3, or variant thereof as taught herein, e.g., aspartic acid, may, for example, be mutated into a positively charged amino acid residue such as histidine, lysine, or arginine, preferably into lysine. The amino acid residue on position 555 of the amino acid sequence of SEQ ID NO:4 or a variant thereof, or the amino acid residue corresponding to this amino acid residue in any of SEQ ID NO: 2 or 3, or variants thereof as taught herein, e.g., asparagine, may, for example, be mutated into an aromatic amino acid residue such as phenylalanine, tryptophan, or tyrosine, preferably into tyrosine. The amino acid residue at position 556 of the amino acid sequence of SEQ ID NO:4 or a variant thereof, or the amino acid residue corresponding to this amino acid residue in any of SEQ ID NO: 2 or 3, or variants thereof as taught herein, e.g., methionine, may, for example, be mutated into an amino acid residue with a small side chain such as glycine, serine, cysteine, alanine, threonine, or valine, preferably into valine.

In an embodiment, the active mutations that are made in the endogenous CENPC protein to yield an actively mutated CENPC protein are selected from the group consisting of 552_553insH, D554K, N555Y, M556V, or any combinations thereof as taught herein.

In certain embodiments, said polynucleotide comprises the nucleic acid sequence of any of SEQ ID NO:7, 9, 12, or 13.

In one embodiment of the invention, nucleic acid sequences encoding CENPC proteins (including CENPC proteins, or variants or fragments thereof, having an active mutation), as described above, are used to make chimeric genes, and/or vectors for transfer of the CENPC protein encoding polynucleotides into a host cell and production of the CENPC protein(s) in host cells, such as cells, tissues, organs or organisms derived from transformed cell(s). Vectors for the production of CENPC protein (or protein fragments or variants thereof) as taught herein in plant cells are herein referred to as "expression vectors".

Suitable host cells for expression of CENPC proteins include prokaryotes, yeast, or higher eukaryotic cells. Appropriate cloning and expression vectors for use with bacterial, fungal, yeast, and mammalian cellular hosts are described, for example, in Pouwels et al., Cloning vectors: A Laboratory Manual, Elsevier, N.Y., (1985). Cell-free translation systems could also be employed to produce the proteins of the present invention using RNAs derived from nucleic acid sequences disclosed herein.

Suitable prokaryotic host cells include gram-negative and gram-positive organisms, for example, *Escherichia coli* or *Bacilli*. Another suitable prokaryotic host cell is *Agrobacterium*, in particular *Agrobacterium tumefaciens*.

CENPC proteins as taught herein can also be expressed in yeast host cells, for example from the *Saccharomyces* genus (e.g., *Saccharomyces cerevisiae*). Other yeast genera, such as *Pichia* or *Kluyveromyces*, can also be employed.

Alternatively, CENPC proteins as taught herein may be expressed in higher eukaryotic host cells, including plant cells, fungal cells, insect cells, and mammalian, optionally non-human, cells.

One embodiment of the invention is a non-human organism modified to comprise a polynucleotide as taught herein. The non-human organism and/or host cell may be modified by any methods known in the art for gene transfer including, for example, the use of delivery devices such as lipids and viral vectors, naked DNA, electroporation, chemical methods and particle-mediated gene transfer. In an advantageous embodiment, the non-human organism is a plant.

Any plant cell may be a suitable host cell. Suitable plant cells include those from monocotyledonous plants or dicotyledonous plants. For example, the plant may belong to the genus *Solanum* (including *Lycopersicon*), *Nicotiana*, *Capsicum*, *Petunia* and other genera.

The following host species may suitably be used: Tobacco (*Nicotiana* species, e.g. *N. benthamiana, N. plumbaginifolia, N. tabacum*, etc.), vegetable species, such as tomato (*L. esculentum*, syn. *Solanum lycopersicum*) such as e.g. cherry tomato, var. cerasiforme or currant tomato, var. pimpinellifolium) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*), coffee (*Coffea*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), Brassica spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or japonica cultivar-group), forage grasses, pearl millet (*Pennisetum* spp. e.g. *P. glaucum*), tree species (Pinus, poplar, fir, plantain, etc), tea, coffea, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia, Chrysanthemum*, Lily, *Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

Preferred host cells are derived from "crop plants" or "cultivated plants", i.e. plant species which is cultivated and bred by humans. A crop plant may be cultivated for food or feed purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork, fibres (such as cotton) and the like.

The construction of chimeric genes and vectors for, preferably stable, introduction of CENPC protein-encoding nucleic acid sequences as taught herein into the genome of host cells is generally known in the art. To generate a chimeric gene the nucleic acid sequence encoding a CENPC protein as taught herein is operably linked to a promoter sequence, suitable for expression in the host cells, using standard molecular biology techniques. The promoter sequence may already be present in a vector so that the CENPC protein encoding nucleic acid sequence is simply inserted into the vector downstream of the promoter sequence. The vector may then be used to transform the host cells and the chimeric gene may be inserted in the nuclear genome or into the plastid, mitochondrial or chloroplast genome and expressed using a suitable promoter (e. g., Mc Bride et al., 1995 Bio/Technology 13, 362; U.S. Pat. No. 5,693,507). In an embodiment the chimeric gene as taught herein comprises a suitable promoter for expression in plant cells or microbial cells (e.g. bacteria), operably linked to a nucleic acid sequence encoding a CENPC protein as taught herein, optionally followed by a 3'nontranslated nucleic acid sequence. The bacteria may subsequently be used for plant transformation (*Agrobacterium*-mediated plant transformation).

Plants Expressing CENPC Polypeptides Having an Active Mutation

The present invention provides plants or plant cells expressing a CENPC polypeptide having an active mutation as taught herein. The present invention also provides plants comprising a polynucleotide as taught herein, a chimeric gene as taught herein, or a vector as taught herein. The plant preferably belongs to the family Solanaceae, more preferably to the genus *Solanum*, yet more preferably to the species *Solanum lycopersicum*.

The plants or plant cells preferably do not express, or express at reduced levels (e.g., less than 90, 80, 70, 60, 50, 40, 30, 20, 10% of wild type levels), an endogenous CENPC protein. For example, one can generate a mutation in an endogenous CENPC protein that reduces or eliminates endogenous CENPC protein activity or expression, or one can generate a knockout for endogenous CENPC protein. In this case, one may generate a plant heterozygous for the gene knockout or mutation and introduce an expression vector for expression of a CENPC protein having an active mutation in the plant. Progeny from the heterozygote can then be selected that are homozygous for the mutation or knockout but that comprise the CENPC protein having an active mutation.

Accordingly, in plants or plant cells taught herein preferably one or both endogenous CENPC alleles are knocked out or mutated such that said plants or plant cells significantly or essentially completely lack endogenous CENPC activity, i.e., sufficient to induce embryo lethality without complementary expression of a CENPC protein having an active mutation as taught herein. In plants having more than a diploid set of chromosomes, all endogenous CENPC alleles may be inactivated, mutated or knocked out. Alternatively, the expression of endogenous CENPC protein may be silenced by any way known in the art, e.g. by introducing a siRNA or microRNA that reduces or eliminates expression of endogenous CENPC protein. Ideally, the silencing agent is selected to silence the endogenous CENPC protein but not the CENPC protein having an active mutation.

Methods for the Generation of Plants

It is an embodiment of the invention to modify an endogenous CENPC gene using targeted mutagenesis methods (also referred to as targeted nucleotide exchange (TNE) or oligo-directed mutagenesis (ODM)). Targeted mutagenesis methods include, without limitation, those employing zinc finger nucleases, Cas9-like, Cas9/crRNA/tracrRNA or Cas9/gRNA CRISPR systems, or targeted mutagenesis methods employing mutagenic oligonucleotides, possibly containing chemically modified nucleotides for enhancing mutagenesis with sequence complementarity to the CENPC gene, into plant protoplasts (e.g., KeyBase® or TALENs).

Alternatively, mutagenesis systems such as TILLING (Targeting Induced Local Lesions I N Genomics; McCallum et al., 2000, Nat Biotech 18:455, and McCallum et al. 2000, Plant Physiol. 123, 439-442, both incorporated herein by reference) may be used to generate plant lines which comprise a CENPC gene encoding a CENPC protein having an active mutation. TILLING uses traditional chemical mutagenesis (e.g. EMS mutagenesis) followed by high-throughput screening for mutations. Thus, plants, seeds and tissues comprising a CENPC gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Modified plants may be distinguished from non-modified plants, i.e., wild type plants, by molecular methods, such as the mutation(s) present in the DNA, and by the modified phenotypic characteristics. The modified plants may be homozygous or heterozygous for the mutation.

Thus, a method for making a plant as taught herein is provided, which method comprises the steps of: i) modifying an endogenous plant CENPC-encoding polynucleotide within a plant cell to obtain a plant CENPC-encoding polynucleotide having an active mutation; ii) selecting a plant cell comprising the plant CENPC-encoding polynucleotide having an active mutation; and iii) optionally, regenerating a plant from said plant cell.

The present invention also provides a method for making a plant as taught herein, comprising the steps of: i) transforming a plant cell with a polynucleotide as taught herein, a chimeric gene as taught herein, or a vector as taught herein; ii) selecting a plant cell comprising said polynucleotide; and iii) optionally, regenerating a plant from said plant cell.

The methods for making a plant as taught herein may further comprise the step of modifying an endogenous plant CENPC protein-encoding polynucleotide or any other endogenous plant polynucleotide involved in expression of said polynucleotide within said plant cell to prevent expression of endogenous CENPC protein.

The CENPC protein-encoding polynucleotides, preferably a CENPC protein-encoding chimeric gene, as taught herein can be stably inserted in a conventional manner into the nuclear genome of a single plant cell, and the so-transformed plant cell can be used in a conventional manner to produce a transformed plant that has an altered phenotype due to the presence of the CENPC protein as taught herein in certain cells at a certain time. In this regard, a T-DNA vector, comprising a CENPC protein-encoding polynucleotide as taught herein, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Likewise, selection and regeneration of transformed plants from transformed plant cells is well known in the art. Obviously, for different species and even for different varieties or cultivars of a single species, protocols are specifically adapted for regenerating transformants at high frequency.

The resulting transformed plant can be used in a conventional plant breeding scheme to produce haploid plants that may subsequently become doubled haploid plants.

Methods for the Generation of Haploid Plants and/or Doubled Haploid Plants

The invention also relates to a method of generating a haploid plant, a plant with aberrant ploidy or a doubled haploid plant, said method comprising the steps of:

crossing a plant expressing an endogenous CENPC protein to the plant as taught herein; and selecting a haploid plant, a plant with aberrant ploidy, or a doubled haploid plant.

The skilled person is capable of selecting a haploid plant. Exemplary techniques include flow cytometry, or validation by specific SNP calling.

Said plant expressing an endogenous CENPC protein may be an F1 plant.

The plant expressing an endogenous CENPC protein may be a pollen parent of the cross, or may be an ovule parent of the cross.

Crossing a plant as taught herein, lacking expression of an endogenous CENPC protein to take part in the kinetochore complex and expressing a CENPC protein having an active mutation as taught herein, to a wild-type plant will result in at least some progeny that is haploid and comprises only chromosomes from the plant that expresses the endogenous CENPC protein. Thus, the present invention allows for the generation of haploid plants having all of its chromosomes from a plant of interest by crossing the plant of interest with a plant expressing a CENPC protein having an active mutation as taught herein, and collecting the resulting haploid seed.

Thus, genome elimination can be engineered with a precise molecular change independent of parental genotype. CENPC protein is found in any plant species. This allows haploid plants to be made in species where conventional methods for haploid plant production, such as tissue culture of haploid cells and wide crosses, are unsuccessful.

The plant expressing a CENPC protein having an active mutation as taught herein may be crossed as either the male or female parent. The methods taught herein allow for transfer of paternal chromosomes into maternal cytoplasm. Thus, it can generate cytoplasmic male sterile lines with a desired genotype in a single step.

Additionally, the present disclosure teaches a method of generating a doubled haploid plant, said method comprising the steps of:

crossing a plant expressing an endogenous CENPC protein to the modified plant as taught herein; selecting a haploid plant; and converting said haploid plant into a doubled haploid plant.

Thus, once generated, haploid plants can be used for the generation of doubled haploid plants, which comprise an exact duplicate copy of chromosomes. A wide variety of methods are known for generating doubled haploid organisms from haploid organisms. For example, chemicals such as colchicine may be applied to convert the haploid plant into a doubled haploid plant. Alternatively, ploidy may double spontaneously during embryonal development or at a later developmental stage of a plant.

In an embodiment, the methods for generation of haploid plants, plants with aberrant ploidy and/or doubled haploid plants as taught herein do not comprise sexually crossing the whole genomes of said plant. Instead, one set of chromosomes is eliminated during the cross.

Doubled haploid plants can be further crossed to other plants to generate F1, F2, or subsequent generations of plants with desired traits.

Doubled haploids plants may be obtained that do not bear transgenic or mutagenized genes. Additionally, doubled haploid plants can rapidly create homozygous F2s from a hybrid F1.

Sequence Listing

SEQ ID NO:1: *Consensus* CENPC motif, protein sequence
SEQ ID NO:2: *Consensus Solanaceae* CENPC protein sequence
SEQ ID NO:3: *Consensus Solanum* CENPC protein sequence
SEQ ID NO:4: *Solanum lycopersicum* CENPC protein sequence (Solyc03g120340.2.1)
SEQ ID NO:5: *Consensus Solanaceae* CENPC DH-inducer domain protein sequence
SEQ ID NO:6: *Consensus Solanum* CENPC DH-inducer domain protein sequence
SEQ ID NO:7: *Solanum lycopersicum* CENPC-552_553insH-D554K-N555Y coding sequence
SEQ ID NO:8: *Solanum lycopersicum* CENPC-552_553insH-D554K-N555Y protein sequence
SEQ ID NO:9: *Solanum lycopersicum* CENPC-M556V coding sequence
SEQ ID NO:10: *Solanum lycopersicum* CENPC-M556V protein sequence
SEQ ID NO:11: *Solanum lycopersicum* CENPC genomic DNA sequence (Solyc03g120340.2.1)
SEQ ID NO:12: *Solanum lycopersicum* CENPC-552_553insH-D554K-N555Y genomic DNA sequence
SEQ ID NO:13: *Solanum lycopersicum* CENPC-M556V genomic DNA sequence
SEQ ID NO:14: *Solanum lycopersicum* CENPC coding sequence (Solyc03g120340.2.1)
SEQ ID NO: 15: Consensus Cucurbitaceae CENPC protein sequence
SEQ ID NO:16: Consensus Brassicaceae CENPC protein sequence
SEQ ID NO:17: Consensus Fabaceae CENPC protein sequence
SEQ ID NO:18: Consensus Poaceae CENPC protein sequence
SEQ ID NO:19: Consensus Rosaceae CENPC protein sequence

BRIEF DESCRIPTION OF THE FIGURE

FIG. 1 shows a tetrad of a CENPC-552_553insH-D554K-N555Y mutant. The arrow indicates a micronucleus.

EXAMPLES

Material and Methods
Plant Material

Two tomato cultivars were used, namely "MoneyBergTMV+" and "MicroTom". From a tomato MoneyBergTMV+ mutant population two somatic non-synonymous mutants were selected, following methods described in WO 2007/037678 and WO2009/041810 in the gene CENPC, namely CENPC-552_553insH-D554K-N555Y and CENPC-M556V. The CENPC-552_553insH-D554K-N555Y mutations are in amino acid residues 554 and 555 of the endogenous CENPC protein, with an insertion of an additional amino acid residue between protein positions 552 and 553 due to a splice acceptor site mutation. The CENPC-M556V is mutated at amino acid residue 556 of the endogenous CENPC protein. From the same tomato MoneyBerg TMV+ mutant population a somatic synonymous mutant was selected, following methods described in WO 2007/037678 and WO2009/041810 in the gene Msi2, namely Msi2_D337D, which is mutated at amino acid position 337. The selected mutant plants were self-pollinated and in the offspring, plants were selected that were homozygous for the mutated loci or locus, respectively.

Method

Uni-parental genome elimination and the resulting production of a haploid plant was provoked by making a cross between a so called haploid inducer line and another not haploid inducer line, for example a breeding line or MicroTom. Crosses of tomato lines for uni-parental genome elimination were performed at relatively high temperatures (26-28° C.), since it is known that an elevated temperature can, but only in some cases, have a positive effect on the occurrence of uni-parental genome elimination (Sanei et al. PNAS 108.33 (2011): E498-E505).

Results

The non-synonymous mutations of G to T, G to A, C to A and A to T in the CENPC-552_553insH-D554K-N555Y mutant resulted in three changes at the protein level. (1) The splice acceptor site just before exon 7 with the wild type sequence "tagcag^GTT" (intron 6 in lower case type setting, exon 7 first codon in uppercase type setting, splice site is indicated by the caret symbol) has a G to T mutation, which resulted in the creation of a novel splice acceptor site: "tag^CATGTT". Hereby a "CAT" codon encoding for a histidine is inserted between amino acid positions 552 and 553, extending exon 7 at the 5'-end (SEQ ID NO:7). (2) The G to A and C to A mutation resulted in an amino acid modification of an aspartic acid to a lysine at protein position 554. (3) The A to T mutation resulted in an amino acid modification of an asparagine to a tyrosine at protein position 555. The non-synonymous mutation of A to G in the CENPC-M556V mutant resulted in an amino acid modification of a methionine to a valine at protein position 556. The synonymous mutation of C to T in the Msi2_D337D mutant did not result in an amino acid modification. Furthermore this plant has been equally treated during selection from the mutant population and did not have any mutation in the CENPC gene. Therefore the Msi2_D337D mutant was used as a control for the uni-parental genome elimination crosses.

Mutant plants homozygous for the CENPC-552_553insH-D554K-N555Y, the CENPC-M556V or the Msi2_D337D mutation were used as pollen donor and as female in crosses at relatively high temperatures (26-28° C.) using non-mutated wild type MicroTom plants as female or pollen donor, respectively. Table 1 lists an overview of all crosses made and the number of offspring plants which were evaluated for the MicroTom phenotype.

TABLE 1

List of crosses made. Genetic background of all listed mutant plants is MoneyBergTMV+. Shown are the number of offspring plants tested and the number of offspring plants which showed MicroTom dwarf phenotype and the year the cross was performed.

| Plant used as female | Plant used as male | Number of plants tested | Number of plants with MicroTom phenotype | Year |
|---|---|---|---|---|
| CenPC-552_553insH-D554K-N555Y | MicroTom | 188 | 2 | 2014 |
| MicroTom | CenPC-552_553insH-D554K-N555Y | 65 | 1 | 2014 |
| CenPC-552_553insH-D554K-N555Y | MicroTom | 564 | 3 | 2015 |
| MicroTom | CenPC-552_553insH-D554K-N555Y | 306 | 2 | 2015 |
| MicroTom | CenPC-M556V | 188 | 4 | 2014 |
| MicroTom | CenPC-M556V | 317 | 1 | 2015 |
| Msi2_D337D | MicroTom | 160 | 0 | 2014 |
| MicroTom | Msi2_D337D | 36 | 0 | 2014 |
| MoneyBergTMV+ | MicroTom | 188 | 0 | 2015 |
| MicroTom | MoneyBergTMV+ | 188 | 0 | 2015 |

Seeds derived from CENPC-552_553insH-D554K-N555Y, CENPC-M556V, Msi_D337D and MoneyBerg TMV+ crosses listed in table 1 were sown and the plants were evaluated for their DNA content by means of flow cytometry. The flow cytometry analysis resulted in a determination of only normal diploid ploidy levels for all plants tested, similar to wild type tomato cultivars such as MoneyBergTMV+, with the exception of one plant derived from a CENPC-M556V x MicroTom cross from 2015; this plant was found to be aneuploid. The cultivar MicroTom has a dwarf phenotype, which is known to be recessive (Marti et al, J Exp Bot, Vol. 57, No. 9, pp. 2037-2047, 2006). After a cross of MicroTom to or with, for instance a MoneyBergTMV+ wild type cultivar, one only finds offspring with the indeterminate non-dwarf phenotype of the MoneyBergTMV+ wild type cultivar. The same was found for crosses with the Msi2_D337D synonymous mutant and MicroTom; all offspring of a MicroTom and Msi2_D337D mutant crosses showed the indeterminate non-dwarf phenotype of the MoneyBergTMV+ parent. Remarkably, using the CENPC-552_553insH-D554K-N555Y mutant as male or female parent, in total 8 plants were found which showed a MicroTom phenotype. Furthermore, using the CENPC-M556V as male parent, in total 5 plants were found which showed a MicroTom phenotype. For all mentioned 13 plants with MicroTom phenotype, their phenotype indicates that the MoneyBergTMV+ parent genetic material is not part of the resulting offspring and this indicates that these 13 offspring plants are of haploid MicroTom origin. The ploidy of all mentioned 13 plants with MicroTom phenotype was found to be diploid, which indicates that spontaneous doubling had occurred, a phenomena which has been described to have an exceptional high frequency of appearance for tomato (Report of the Tomato Genetics Cooperative Number 62—December 2012).

For CENPC-552_553insH-D554K-N555Y offspring with MicroTom phenotype, in order to determine whether and to what extent uni-parental genome elimination had occurred, a single nucleotide polymorphism (SNP) assay was run for in total 44 positions for the 2014 offspring, spread across each of the 12 tomato chromosomes (4 SNPs on chromosome 1, 2, 3, 4, 5, 6, 10 and 12; 3 SNPs on chromosome 8 and 11; 2 SNPs on chromosome 9). The same analysis was performed for the 2015 offspring, now on 22 positions (2 SNPs on chromosome 1, 2, 3, 4, 5, 6, 7, 8, 10 and 12; 1 SNP on chromosome 9 and 11). The single nucleotide polymorphisms selected were homozygous for one base pair for the MicroTom parent and homozygous for all but not the MicroTom base pair in the MoneyBergTMV+ parent. A regular cross between a wild type MicroTom cultivar and the MoneyBergTMV+ cultivar would result in a heterozygous single nucleotide polymorphism score. However, when the process of uni-parental genome elimination has occurred, one expects the loss of the haploid inducer line genome.

The single nucleotide polymorphism test resulted in calling of only homozygous base pair scores from the MicroTom parent for each of the 8 offspring plants which also showed the MicroTom phenotype and none of the MoneyBergTMV+ parent were called. Based on the single nucleotide polymorphism scores it was concluded that the complete genome of the CENPC-552_553insH-D554K-N555Y mutant was no longer present in the offspring. Therefore, it can be concluded that the CENPC-552_553insH-D554K-N555Y mutant functions as a highly efficient haploid inducer line. In the crosses in which the CENPC-552_553insH-D554K-N555Y mutant was used as female parent, a selfing of MicroTom can be ruled out. It is highly unlikely that in the experiment using MicroTom as female parent selfing took place, given the very low number of offspring showing the MicroTom phenotype (only 1 seed out of 65 and 2 seeds out of 306), and the fact that only homozygous base pairs were scored.

For CENPC-M556V offspring with MicroTom phenotype, in order to determine whether and to what extent uni-parental genome elimination had occurred, a single nucleotide polymorphism (SNP) assay was run for in total 24 positions, spread across each of the 12 tomato chromosomes, with 2 SNPs per chromosome in 2014 and 22 positions were tested in 2015 (2 SNPs on chromosome 1, 2, 3, 4, 5, 6, 7, 8, 10 and 12; 1 SNP on chromosome 9 and 11). The single nucleotide polymorphisms selected were homozygous for one base pair for the MicroTom parent and homozygous for all but not the MicroTom base pair in the MoneyBergTMV+ parent. A regular cross between a wild type MicroTom cultivar and the MoneyBergTMV+ cultivar would result in a heterozygous single nucleotide polymorphism score. However, when the process of uni-parental genome elimination has occurred, one expects the loss of the haploid inducer line genome.

The single nucleotide polymorphism test resulted in calling of only homozygous base pair scores from the MicroTom parent for each of the 5 offspring plants which also showed the MicroTom phenotype and none of the MoneyBergTMV+ parent were called. Based on the single nucleotide polymorphism scores it was concluded that the complete genome of the CENPC-M556V mutant was no longer present in the offspring. Therefore, it can be concluded that the CENPC-M556V mutant functions as a highly efficient haploid inducer line. In the crosses in which the CENPC-M556V mutant was used as female parent, a selfing of MicroTom can be ruled out. It is highly unlikely that in the experiment using MicroTom as female parent selfing took place, given the very low number of offspring showing the MicroTom phenotype (only 4 seed out of 188 and 1 out of 317), and the fact that only homozygous base pairs were scored.

Phenotype of the CENPC-552_553insH-D554K-N555Y Mutant

Pollen tetrads of the CENPC-552_553insH-D554K-N555Y mutant and of not mutated RZ52201 control plants were checked for occurrence of aberrancies. From four different flower trusses at least one flower was taken, its anthers were stained with DAPI (4',6-diamidino-2-fenylindool) and stained anthers squashed in order to look at pollen tetrads. For the CENPC-552_553insH-D554K-N555Y mutant, micronuclei were observed with an average frequency of 2.34±0.90% (FIG. 1). For the control plant flowers, micronuclei were observed with an average frequency of 0.58±0.36%. The difference between control and mutant frequencies was evaluated with a Mann-Whitney rank sum test and it was found that the difference in the median values between the two groups is greater than would be expected by chance, therefore it is concluded that there was a statistically significant difference (P=0.016).

It can therefore be concluded that the separation of chromosomes during meiosis is much more frequently disturbed as a result of the CENPC-552_553insH-D554K-N555Y mutation compared to the control. Aberrant mitosis, for instance observations of micronuclei, are often used as direct evidences of chromosome elimination and haploid production in inter-, intra-specific hybridizations in crops. For example, aberrant mitosis as well as aberrant meiosis, for instance micronuclei, were found in a study of a maize DH-inducer line (Qiu, Fazhan, et al. Current Plant Biology 1 (2014): 83-90). The observations of meiosis micronuclei in the CENPC-552_553insH-D554K-N555Y mutant, suggest that during mitosis similar processes occur. It is likely that the process of uniparental genome elimination during the first mitotic divisions after fusion of wild type and CENPC-552_553insH-D554K-N555Y zygotes takes place and that this results in the observed induction of haploids.

The invention claimed is:

1. A modified CENPC protein of plant origin comprising one or more active mutations, wherein the one or more active mutations are in a protein comprising at least 75% sequence identity to the amino acid sequence of any of SEQ ID NO:2, 3, 4 or 15-19, wherein the one or more active mutations are chosen from the group consisting of an insertion between amino acid residues at position 552 and 553, a mutation of an amino acid residue at position 554, a mutation of an amino acid residue at position 555 and a mutation of an amino acid residue at position 556, or any combination thereof, in the amino acid sequence of any of SEQ ID NO: 3 or 4, and wherein the insertion is not an insertion of a glutamine residue between amino acid residues 552 and 553; or of an insertion between amino acid residues at position 555 and 556, a mutation of an amino acid residue at position 557, a mutation of an amino acid residue at position 558 and a mutation of an amino acid residue at position 559, or any combination thereof, in the amino acid sequence of SEQ ID NO: 2, and wherein the protein, when present in a plant in the absence of its endogenous CENPC protein, allows generation of haploid progeny, or progeny with aberrant ploidy, at a higher frequency than when the plant is crossed with a wild-type plant.

2. The CENPC protein according to claim 1, wherein the amino acid that is mutated at position 554 of the amino acid sequence of any of SEQ ID NO: 3 or 4, or at position 557 in the amino acid sequence of SEQ ID NO: 2, is aspartic acid and/or the amino acid that is changed at position 555 of the amino acid sequence of any of SEQ ID NO: 3 or 4, or at position 558 in the amino acid sequence of SEQ ID NO: 2, is asparagine and/or the amino acid that is changed at position 556 of the amino acid sequence of any of SEQ ID NO: 3 or 4, or at position 559 in the amino acid sequence of SEQ ID NO: 2, is methionine.

3. The CENPC protein according to claim 1, wherein the amino acid at position 554 of the amino acid sequence of any of SEQ ID NO: 3 or 4, or at position 557 in the amino acid sequence of SEQ ID NO: 2, is changed into a positively charged amino acid residue, and/or the amino acid at position 555 of the amino acid sequence of any of SEQ ID NO: 3 or 4, or at position 558 in the amino acid sequence of SEQ ID NO: 2, is changed into a tyrosine and/or the amino acid at position 556 of the amino acid sequence of any of SEQ ID NO: 3 or 4, or at position 557 in the amino acid sequence of SEQ ID NO: 2, is changed into valine, and/or wherein a positively charged residue is inserted between amino acid residues 552 and 553 of the amino acid sequence of any of SEQ ID NO: 3 or 4, or between amino acid residues 555 and 556 in the amino acid sequence of SEQ ID NO: 2.

4. The CENPC protein according to claim 1, wherein a histidine is inserted between amino acid residues 552 and 553 of the amino acid sequence of any of SEQ ID NO: 3 or 4, or between amino acid residues 555 and 556 in the amino acid sequence of SEQ ID NO: 2, and/or an aspartic acid at position 554 of the amino acid sequence of any of SEQ ID NO: 3 or 4, or at position 557 in the amino acid sequence of SEQ ID NO: 2, is changed into a lysine and/or an asparagine at position 555 of the amino acid sequence of any of SEQ ID NO: 3 or 4, or at position 558 in the amino acid sequence of SEQ ID NO: 2, is changed into a tyrosine.

5. The CENPC protein according to claim 4, which comprises the amino acid sequence of SEQ ID NO:8.

6. The CENPC protein according to claim 4, which comprises the amino acid sequence of SEQ ID NO:10.

7. A polynucleotide encoding the CENPC protein according to claim 1.

8. The polynucleotide according to claim 7, comprising the nucleic acid sequence of SEQ ID NO:11 or 14, or a variant thereof having at least 70% sequence identity to SEQ ID NO:11 or 14, respectively, but in which one or more nucleotides at positions 2449-2450 and/or 2454-2462 of the nucleic acid sequence of SEQ ID NO:11 or at positions 1660-1668 in SEQ ID NO:14 are modified such that the nucleic acid encodes a CENPC protein in which the amino acid sequence of SEQ ID NO:3 has an altered residue at position 554 and/or at position 555 and/or at position 556, and/or has an insertion of an amino acid residue, between the amino acid residues 552 and 553 of the amino acid sequence of SEQ ID NO:3.

9. The polynucleotide according to claim 7, comprising the nucleic acid sequence according to any one of SEQ ID NO:7, 9, 12 or 13.

10. A vector comprising the polynucleotide according to claim 7.

11. A host cell comprising a polynucleotide according to claim 7.

12. A plant, seed or plant cell comprising a polynucleotide according to claim 7.

13. The plant, seed or plant cell according to claim 12, wherein the endogenous CENPC protein is not expressed.

14. The plant, seed or plant cell according to claim 12, which is a *Solanum* plant.

15. A method for making a plant, comprising:
(a) modifying an endogenous plant CENPC protein-encoding polynucleotide within a plant cell to obtain a modified plant CENPC protein-encoding;
(b) selecting a plant cell comprising the modified plant CENPC protein-encoding polynucleotide; and
(c) optionally, regenerating a plant from the plant cell, wherein the endogenous plant CENPC protein-encoding polynucleotide encodes a CENPC protein having at least 75% sequence identity to the amino acid sequence of any one of SEQ ID NO:2, 3, 4 or 15-19, and wherein the modified plant CENPC protein-encoding polynucleotide encodes a modified CENPC protein comprising one or more active mutations, which protein, when present in a plant in the absence of its endogenous CENPC protein, allows generation of haploid progeny, or progeny with aberrant ploidy, at a higher frequency than when the plant is crossed with a wild-type plant.

16. A method for making a plant, comprising:
(a) transforming a plant cell with a modified plant CENPC protein-encoding polynucleotide;
(b) selecting a plant cell comprising the polynucleotide; and
(c) optionally, regenerating a plant from the plant cell, wherein the plant CENPC protein-encoding polynucleotide encodes a modified CENPC protein comprising one or more active mutations, wherein the one or more active mutations are in a protein comprising at least 75% sequence identity to the amino acid sequence of any of SEQ ID NO:2, 3, 4 or 15-19, and wherein the protein, when present in a plant in the absence of its endogenous CENPC protein, allows generation of haploid progeny, or progeny with aberrant ploidy, at a higher frequency than when the plant is crossed with a wild-type plant.

17. The method according to claim 16, further comprising:
modifying the plant cell to prevent expression of endogenous CENPC protein,
wherein the endogenous plant CENPC protein-encoding polynucleotide encodes a CENPC protein having at least 75% sequence identity to the amino acid sequence of any of SEQ ID NO:2, 3, 4 or 15-19.

18. A method of generating a haploid plant, or a plant with aberrant ploidy, comprising:
(a) crossing a plant expressing an endogenous plant CENPC protein to a plant obtained by the method of claim 15, wherein the plant does not express an endogenous CENPC protein at least in its reproductive parts and/or during embryonic development;
(b) harvesting seed;
(c) growing at least one seedling, plantlet or plant from said seed; and
(d) selecting a haploid seedling, plantlet or plant; a seedling, plantlet or plant with aberrant ploidy; or a doubled haploid seedling, plantlet or plant.

19. A method of generating a doubled haploid plant, comprising: converting the haploid plant obtained in step d) of claim 18 into a doubled haploid plant.

20. The method according to claim 19, wherein the conversion is performed by treatment with colchicine.

21. The method of claim 15, wherein the one or more active mutations are present in a doubled haploid inducer domain represented by the amino acid sequences in any of SEQ ID NO: 5 or 6.

22. The method of claim 15, wherein the one or more active mutations are chosen from the group consisting of a mutation between amino acid residues at position 552 and 553, a mutation of an amino acid residue at position 554, a mutation of an amino acid residue at position 555 and a mutation of an amino acid residue at position 556, or any combination thereof, in the amino acid sequence of any of SEQ ID NO: 3 or 4; or of a mutation between amino acid residues at position 555 and 556, a mutation of an amino acid residue at position 557, a mutation of an amino acid residue at position 558 and a mutation of an amino acid residue at position 559, or any combination thereof, in the amino acid sequence of SEQ ID NO: 2.

23. The method of claim 22, wherein the amino acid that is mutated at position 554 of the amino acid sequence of any of SEQ ID NO: 3 or 4, or at position 557 in the amino acid sequence of SEQ ID NO: 2, is aspartic acid and/or the amino acid that is changed at position 555 of the amino acid sequence of any of SEQ ID NO: 3 or 4, or at position 558 in the amino acid sequence of SEQ ID NO: 2, is asparagine and/or the amino acid that is changed at position 556 of the amino acid sequence of any of SEQ ID NO: 3 or 4, or at position 559 in the amino acid sequence of SEQ ID NO: 2, is methionine.

24. The method of claim 22, wherein the amino acid at position 554 of the amino acid sequence of any of SEQ ID NO: 3 or 4, or at position 557 in the amino acid sequence of SEQ ID NO: 2, is changed into a positively charged amino acid residue and/or the amino acid at position 555 of the amino acid sequence of any of SEQ ID NO: 3 or 4, or at position 558 in the amino acid sequence of SEQ ID NO: 2, is changed into a tyrosine and/or the amino acid at position 556 of the amino acid sequence of any of SEQ ID NO: 3 or 4, or at position 557 in the amino acid sequence of SEQ ID NO: 2, is changed into valine, and/or wherein a positively charged residue is inserted between amino acid residues 552 and 553 of the amino acid sequence of any of SEQ ID NO: 3 or 4, or between amino acid residues 555 and 556 in the amino acid sequence of SEQ ID NO: 2.

25. The method of claim 22, wherein a histidine is inserted between amino acid residues 552 and 553 of the amino acid sequence of any of SEQ ID NO: 3 or 4, or between amino acid residues 555 and 556 in the amino acid sequence of SEQ ID NO: 2, and/or an aspartic acid at position 554 of the amino acid sequence of any of SEQ ID NO: 3 or 4, or at position 557 in the amino acid sequence of SEQ ID NO: 2, is changed into a lysine and/or an asparagine at position 555 of the amino acid sequence of any of SEQ ID NO: 3 or 4, or at position 558 in the amino acid sequence of SEQ ID NO: 2, is changed into a tyrosine.

26. The method of claim 15, wherein the modified protein comprises the amino acid sequence of SEQ ID NO: 8.

27. The method of claim 15, wherein the modified protein comprises the amino acid sequence of SEQ ID NO: 10.

28. The method of claim 15, wherein the modified protein is encoded by a polynucleotide comprising the sequence of SEQ ID NO: 7, 9, 12 or 13.

29. The CENPC protein according to claim 1, wherein the one or more active mutations are in a protein comprising at least 75% sequence identity to the amino acid sequence of SEQ ID NO: 3 or 4, wherein the one or more active mutations are chosen from the group consisting of an insertion between amino acid residues at position 552 and 553, a mutation of an amino acid residue at position 554, a mutation of an amino acid residue at position 555 and a mutation of an amino acid residue at position 556, or any combination thereof, in the amino acid sequence of any of SEQ ID NO: 3 or 4, and wherein the insertion is not an insertion of a glutamine residue between amino acid residues 552 and 553.

* * * * *

SEQUENCE LISTING

```
<160> NUMBER OF SEQ ID NOS: 19

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      consensus CenPC motif
<220> FEATURE:
<221> NAME/KEY: MOD_RES
<222> LOCATION: (1)..(1)
<223> OTHER INFORMATION: Asn or Gly
<220> FEATURE:
<221> NAME/KEY: MOD_RES
<222> LOCATION: (2)..(2)
<223> OTHER INFORMATION: Arg, Leu or Val
<220> FEATURE:
<221> NAME/KEY: MOD_RES
<222> LOCATION: (4)..(4)
<223> OTHER INFORMATION: Arg, Lys or Val
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Asn, Lys, Met, Ser or Thr
<220> FEATURE:
<221> NAME/KEY: MOD_RES
<222> LOCATION: (8)..(8)
<223> OTHER INFORMATION: Ile, Met, Thr or Val
<220> FEATURE:
<221> NAME/KEY: MOD_RES
<222> LOCATION: (9)..(9)
<223> OTHER INFORMATION: Arg or Lys
<220> FEATURE:
<221> NAME/KEY: MOD_RES
<222> LOCATION: (10)..(10)
```

```
<223> OTHER INFORMATION: Ile, Leu, Ser, Thr or Val
<220> FEATURE:
<221> NAME/KEY: MOD_RES
<222> LOCATION: (11)..(11)
<223> OTHER INFORMATION: Ala, Arg or Lys
<220> FEATURE:
<221> NAME/KEY: MOD_RES
<222> LOCATION: (13)..(13)
<223> OTHER INFORMATION: Leu or Val
<220> FEATURE:
<221> NAME/KEY: MOD_RES
<222> LOCATION: (14)..(14)
<223> OTHER INFORMATION: Ala, Arg, Asn, Gln or Glu
<220> FEATURE:
<221> NAME/KEY: MOD_RES
<222> LOCATION: (15)..(15)
<223> OTHER INFORMATION: His, Phe, Ser, Trp or Tyr
<220> FEATURE:
<221> NAME/KEY: MOD_RES
<222> LOCATION: (17)..(17)
<223> OTHER INFORMATION: Arg, Leu or Lys
<220> FEATURE:
<221> NAME/KEY: MOD_RES
<222> LOCATION: (18)..(18)
<223> OTHER INFORMATION: Asn or Gly
<220> FEATURE:
<221> NAME/KEY: MOD_RES
<222> LOCATION: (20)..(20)
<223> OTHER INFORMATION: Arg, Gln or Lys
<220> FEATURE:
<221> NAME/KEY: MOD_RES
<222> LOCATION: (21)..(21)
<223> OTHER INFORMATION: Ile, Met, Leu, Phe, Pro or Val
<220> FEATURE:
<221> NAME/KEY: MOD_RES
<222> LOCATION: (22)..(22)
<223> OTHER INFORMATION: Asp, Ile, Leu, Thr or Val
<220> FEATURE:
<221> NAME/KEY: MOD_RES
<222> LOCATION: (24)..(24)
<223> OTHER INFORMATION: Gln, Glu, Gly, Lys, Thr or Val

<400> SEQUENCE: 1

Xaa Xaa Arg Xaa Xaa Xaa Arg Xaa Xaa Xaa Pro Xaa Xaa Xaa Trp
1               5                   10                  15

Xaa Xaa Glu Xaa Xaa Xaa Tyr Xaa
            20

<210> SEQ ID NO 2
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (99)..(99)
<223> OTHER INFORMATION: Any naturally occurring amino acid
<220> FEATURE:
<221> NAME/KEY: MOD_RES
<222> LOCATION: (150)..(150)
<223> OTHER INFORMATION: Any naturally occurring amino acid
<220> FEATURE:
<221> NAME/KEY: MOD_RES
<222> LOCATION: (161)..(161)
<223> OTHER INFORMATION: Any naturally occurring amino acid
<220> FEATURE:
<221> NAME/KEY: MOD_RES
<222> LOCATION: (196)..(196)
<223> OTHER INFORMATION: Any naturally occurring amino acid
<220> FEATURE:
<221> NAME/KEY: MOD_RES
<222> LOCATION: (255)..(255)
<223> OTHER INFORMATION: Any naturally occurring amino acid
<220> FEATURE:
```

```
<221> NAME/KEY: MOD_RES
<222> LOCATION: (260)..(260)
<223> OTHER INFORMATION: Any naturally occurring amino acid
<220> FEATURE:
<221> NAME/KEY: MOD_RES
<222> LOCATION: (390)..(390)
<223> OTHER INFORMATION: Any naturally occurring amino acid
<220> FEATURE:
<221> NAME/KEY: MOD_RES
<222> LOCATION: (554)..(554)
<223> OTHER INFORMATION: Any naturally occurring amino acid
<220> FEATURE:
<221> NAME/KEY: MOD_RES
<222> LOCATION: (696)..(696)
<223> OTHER INFORMATION: Any naturally occurring amino acid
<220> FEATURE:
<221> NAME/KEY: MOD_RES
<222> LOCATION: (700)..(700)
<223> OTHER INFORMATION: Any naturally occurring amino acid
<220> FEATURE:
<221> NAME/KEY: MOD_RES
<222> LOCATION: (708)..(708)
<223> OTHER INFORMATION: Any naturally occurring amino acid

<400> SEQUENCE: 2

Met Val Asn Glu Ala Leu Thr Ser Asp Pro Val Asp Pro Leu Arg Gly
1               5                   10                  15

Leu Ala Gly Leu Ser Leu Leu Pro Lys Thr Ile Arg Val Ser Thr Asp
            20                  25                  30

Ala Ser Val Ser Val Asp Pro Lys Asp Leu Glu Ser Ile His Asn Phe
        35                  40                  45

Met Lys Ser Met Glu Thr Lys Gly Pro Gly Leu Leu Glu Glu Ala Arg
50                  55                  60

Ala Ile Val Asp Asn Gly Ala Glu Leu Leu Asn Thr Lys Phe Thr Ser
65                  70                  75                  80

Phe Ile Met Ser Lys Gly Ile Asp Gly Asp Leu Ala Met Lys Gly Lys
                85                  90                  95

Glu Lys Xaa Gln Glu Arg Arg Pro Gly Leu Gly Arg Lys Arg Ala Arg
            100                 105                 110

Phe Ser Leu Lys Pro Ser Thr Ser Gln Pro Pro Val Ser Thr Ala Pro
        115                 120                 125

Arg Leu Asp Ile Asp Gln Leu Ser Asp Pro Val Glu Phe Phe Ser Ala
130                 135                 140

Ala Glu Arg Leu Glu Xaa Ala Glu Lys Glu Ile Glu Arg Leu Lys Gly
145                 150                 155                 160

Xaa Ser Ile His Asp Pro Asp Val Asn Asn Pro Ala Asn Ala Arg
                165                 170                 175

Arg Arg Arg Pro Gly Ile Leu Gly Lys Ser Val Arg Tyr Lys His Arg
            180                 185                 190

Phe Ser Ser Xaa Gln Pro Glu Asn Asp Asp Ala Phe Ile Ser Ser Gln
        195                 200                 205

Glu Thr Leu Glu Ser Asp Ile Leu Ala Glu His Gly Ser Gln Leu Pro
210                 215                 220

Glu Glu Leu Pro Gly Leu Asn Val Glu Leu Gln Glu Ala Asp Ser Pro
225                 230                 235                 240

Gly Ser Ile Lys Lys Thr Glu Asn Arg Ile Asn Gly Ile Leu Xaa Glu
            245                 250                 255

Leu Leu Ser Xaa Asn Gly Glu Asp Leu Asp Gly Asp Met Ala Val Ser
        260                 265                 270

Lys Leu Gln Glu Arg Leu Gln Ile Lys Pro Ile Glu Leu Gly Thr Leu
    275                 280                 285
```

```
Cys Ile Pro Glu Phe Pro Val Thr Gly Lys Val Asp Gly Lys Ala Phe
    290                 295                 300
Gly Glu Arg Ile Gln Lys Pro Arg Lys Phe Ser Leu Glu Ile Arg Glu
305                 310                 315                 320
Leu Val Lys Ser Ala Thr Glu Gly Thr Pro Ser Thr His Lys Gln His
                325                 330                 335
Glu Glu Ser Pro Ala Ser Asn Leu Ala Ser Pro Thr Pro Pro Lys Ser
            340                 345                 350
Pro Phe Gly Ser Leu Ser Leu Leu Lys Lys Ile Met Gln Ser Asn
        355                 360                 365
Pro Leu Arg Asp Pro Phe Ser Pro Leu Asn Ile Asp Leu Gln Ser Glu
    370                 375                 380
His Pro Asp Trp Ser Xaa Lys Met Asn Ser Gln Cys Val Asn Asn Asn
385                 390                 395                 400
Ala Gly Pro Thr Glu Ser His Gly Glu Thr Glu Asn Asp Asn Thr Asn
                405                 410                 415
Ile Met Val Pro Leu Arg Gly Ser Asp Leu Ser His Glu Gln Leu Met
            420                 425                 430
Glu Lys Asn Ser Gly Arg Asp Ser Val Lys Thr Gly Pro Asn Gly Ser
        435                 440                 445
Arg Ser Gly Met Glu Gln Glu Asn Gly Tyr Asp Asp Ile Asp Ile Asn
450                 455                 460
Thr Asp Ile Asn Leu Asn Met Arg Asn Met Asp Ser His Tyr Glu Ser
465                 470                 475                 480
Asp Gly Leu Asp Lys Val Lys Asp Ser Val Ile Asn Asn Val Leu
                485                 490                 495
Lys Asp Gln Gln Gly Leu Glu Thr Glu Ser Tyr Ile Ser Cys Gln Lys
        500                 505                 510
Met Gln Asp Gly Glu Val Leu Ala Glu Thr Leu Pro Ser Leu Gln Ala
    515                 520                 525
Gln Gly Lys Ala Asp Asp Thr Ala Asn Tyr Thr Val Glu Thr Ala Val
        530                 535                 540
Glu Asp Phe Gly Ser Thr Glu Ile Asp Xaa Gln Val Asp Asn Met Pro
545                 550                 555                 560
Pro Glu Thr Ala His Pro Ser Ala Glu Gln Asp His His Phe Glu Asp
                565                 570                 575
Ser Val Lys Asp Leu Thr Ser Asp Gln Leu Ser Ser Val Ala Val Glu
            580                 585                 590
Val Pro Ser Thr Glu Val Arg Ser Lys Phe Pro Glu Met Ser Pro Gln
        595                 600                 605
His His Ala Gln Ala Lys Asp Lys Gln Gln Lys Ala Lys Arg Pro Ala
    610                 615                 620
Gly Gly Arg Arg Glu Arg Lys Ala Leu Ser Ser Arg Pro Ser Leu Ala
625                 630                 635                 640
Asp Ala Gly Thr Ser Phe Glu Ser Gly Val Arg Arg Ser Lys Arg Met
                645                 650                 655
Lys Thr Arg Pro Leu Glu Tyr Trp Lys Gly Glu Arg Leu Leu Tyr Gly
            660                 665                 670
Arg Val Asn Glu Ser Leu Lys Leu Val Gly Leu Lys Tyr Ile Ser Pro
        675                 680                 685
Gly Lys Gly Ser Val Lys Val Xaa Ser Tyr Ile Xaa Asp Asp Tyr Lys
690                 695                 700
```

-continued

```
Asp Leu Val Xaa Leu Ala Ala Arg Tyr
705             710
```

<210> SEQ ID NO 3
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Val Asn Glu Ala Leu Ile Ser Asp Pro Val Asp Pro Leu His Ser
1               5                   10                  15

Leu Ala Gly Leu Ser Leu Leu Pro Thr Thr Val Arg Val Ser Thr Gly
            20                  25                  30

Ala Ser Val Ser Val Asp Ser Lys Asp Leu Glu Ser Ile His Asn Phe
        35                  40                  45

Met Lys Ser Met Glu Thr Lys Gly Pro Gly Leu Leu Glu Glu Ala Arg
    50                  55                  60

Glu Ile Val Asp Asn Gly Ala Glu Leu Leu Asn Thr Lys Phe Thr Ser
65              70                  75                  80

Phe Ile Arg Ser Lys Gly Ile Asp Gly Asp Leu Ala Ile Lys Gly Lys
                85                  90                  95

Glu Lys Leu Gln Glu Arg Arg Pro Gly Leu Gly Arg Lys Arg Ala Arg
            100                 105                 110

Phe Ser Leu Lys Pro Ser Thr Ser Gln Pro Thr Val Ser Ile Ala Pro
        115                 120                 125

Arg Leu Asp Ile Asp Gln Leu Ser Asp Pro Val Glu Phe Phe Ser Val
    130                 135                 140

Ala Glu Lys Leu Glu Val Ala Glu Lys Glu Ile Glu Arg Gln Lys Gly
145             150                 155                 160

Gly Ser Ile His Asp Pro Asp Val Asn Asn Pro Ala Asn Ala Arg
                165                 170                 175

Arg Arg Arg Pro Gly Ile Leu Gly Lys Ser Val Lys Tyr Lys His Arg
            180                 185                 190

Phe Ser Ser Ser Gln Pro Glu Asn Asp Asp Ala Phe Ile Ser Ser Gln
        195                 200                 205

Glu Thr Leu Glu Asp Asp Ile Leu Val Glu His Gly Ser Gln Leu Pro
    210                 215                 220

Glu Glu Leu His Gly Leu Asn Val Glu Leu Gln Glu Ala Glu Leu Thr
225             230                 235                 240

Gly Pro Ile Lys Lys Ser Glu Asn Arg Ile Asn Lys Ile Leu Asp Glu
                245                 250                 255

Leu Leu Ser Gly Ser Gly Glu Asp Leu Asp Arg Asp Met Ala Val Ser
            260                 265                 270

Lys Leu Gln Glu Gln Leu Lys Ile Lys Pro Ile Glu Leu Gly Thr Leu
        275                 280                 285

Cys Ile Pro Glu Phe Pro Val Thr Gly Lys Phe Asp Gly Lys Ala Leu
    290                 295                 300

Gly Glu Arg Ile Gln Lys Pro Arg Lys Phe Ser Leu Glu Ile Ala Glu
305             310                 315                 320

Leu Val Lys Ser Ala Thr Glu Gly Thr Pro Ser Ser His Lys Gln His
                325                 330                 335

Glu Glu Ser Pro Ala Ser Lys Leu Ala Ser Pro Thr Pro Pro Lys Ser
            340                 345                 350
```

Pro Phe Gly Ser Leu Ser Leu Lys Lys Lys Leu Met Gln Ser Asn
                355                 360                 365

Pro Leu Arg Asp Pro Phe Ser Pro Leu Asn Ile Asp Leu Gln Ser Glu
        370                 375                 380

His Pro Asp Trp Ser Val Lys Lys Ser Gln Cys Val Asn Asn
385                 390                 395                 400

Val Gly Pro Ile Glu Ser Arg Gly Cys Glu Asn Thr Asn Ile Met Val
                405                 410                 415

Pro Leu Arg Gly Ser Asp Leu Val His Glu Gln Pro Ile Glu Lys Asn
        420                 425                 430

Pro Gly Arg Asp Ser Val Lys Thr Gly Pro Asn Gly Ser Arg Ser Gly
        435                 440                 445

Met Glu Gln His Asn Gly Tyr Asp Asp Ile Asp Ala Asn Thr Asn Asp
    450                 455                 460

Asn Leu Asn Met Arg Asn Val Asp Ser His His Glu Ser Asp Gly Leu
465                 470                 475                 480

Asp Lys Val Lys Asp Ser Val Ile Lys Asn Val Leu Lys Ala Leu
                485                 490                 495

Gln Gly Leu Glu Thr Lys Ser Tyr Ile Asn Cys Gln Lys Leu Gln Asp
            500                 505                 510

Ser Glu Val Leu Ala Glu Thr Leu Pro Ser Leu Gln Ala Gln Gly Lys
        515                 520                 525

Ala Val Asp Thr Ala Asn Tyr Thr Ile Glu Thr Ala Val Glu Asp Phe
    530                 535                 540

Gly Ser Thr Glu Ile Asp Gln Leu Val Asp Asn Met Leu Pro Glu Thr
545                 550                 555                 560

Ala Pro Ser Ala Glu Gln Asp His Tyr Phe Glu Asp Ser Val Lys Asp
                565                 570                 575

Leu Asn Ser Asp Gln Leu Asn Ser Val Gly Val Glu Val Pro Ser Arg
        580                 585                 590

Asp Val Arg Pro Lys Phe Pro Glu Met Ser Pro Gln His His Lys Gln
    595                 600                 605

Ala Lys Asp Lys Gln Gln Lys Ala Lys Lys Leu Ala Val Gly Arg Arg
610                 615                 620

Glu Arg Lys His Leu Ser Ser Arg Pro Ser Leu Ala Asp Ala Gly Thr
625                 630                 635                 640

Ser Phe Glu Ser Gly Val Arg Arg Ser Lys Arg Met Lys Thr Arg Pro
                645                 650                 655

Leu Glu Tyr Trp Lys Gly Glu Arg Leu Tyr Gly Arg Val Asp Glu
        660                 665                 670

Gly Leu Lys Leu Val Gly Leu Lys Tyr Ile Ser Pro Gly Lys Gly Ser
    675                 680                 685

Phe Lys Val Lys Ser Tyr Ile Pro Asp Asp Tyr Lys Asp Leu Val Asp
690                 695                 700

Leu Ala Ala Arg Tyr
705

<210> SEQ ID NO 4
<211> LENGTH: 709
<212> TYPE: PRT
<213> ORGANISM: Solanum lycopersicum

<400> SEQUENCE: 4

Met Val Asn Glu Ala Leu Ile Ser Asp Pro Val Asp Pro Leu His Ser

```
1               5                   10                  15
Leu Ala Gly Leu Ser Leu Leu Pro Thr Thr Val Arg Val Ser Thr Gly
            20                  25                  30
Ala Ser Val Ser Val Asp Ser Lys Asp Leu Glu Ser Ile His Asn Phe
            35                  40                  45
Met Lys Ser Met Glu Thr Lys Gly Pro Gly Leu Leu Glu Glu Ala Arg
 50                 55                  60
Glu Ile Val Asp Asn Gly Ala Glu Leu Leu Asn Thr Lys Phe Thr Ser
 65                 70                  75                  80
Phe Ile Arg Ser Lys Gly Ile Asp Gly Asp Leu Ala Ile Lys Gly Lys
            85                  90                  95
Glu Lys Val Gln Glu Arg Arg Pro Gly Leu Gly Arg Lys Arg Ala Arg
            100                 105                 110
Phe Ser Leu Lys Pro Ser Thr Ser Gln Pro Thr Val Ser Ile Ala Pro
            115                 120                 125
Arg Leu Asp Ile Asp Gln Leu Ser Asp Pro Val Glu Phe Phe Ser Val
            130                 135                 140
Ala Glu Lys Leu Glu Val Ala Glu Lys Glu Ile Glu Arg Gln Lys Gly
145                 150                 155                 160
Gly Ser Ile His Asp Pro Asp Val Asn Asn Pro Ala Asn Ala Arg
            165                 170                 175
Arg Arg Arg Pro Gly Ile Leu Gly Lys Ser Val Lys Tyr Lys His Arg
            180                 185                 190
Phe Ser Ser Ser Gln Pro Glu Asn Asp Asp Ala Phe Ile Ser Ser Gln
            195                 200                 205
Glu Thr Leu Glu Asp Asp Ile Leu Val Glu His Gly Ser Gln Leu Pro
            210                 215                 220
Glu Glu Leu His Gly Leu Asn Val Glu Leu Gln Glu Ala Glu Leu Thr
225                 230                 235                 240
Gly Pro Ile Lys Lys Ser Glu Asn Arg Ile Asn Lys Ile Leu Asp Glu
            245                 250                 255
Leu Leu Ser Gly Ser Gly Glu Asp Leu Asp Arg Asp Met Ala Val Ser
            260                 265                 270
Lys Leu Gln Glu Gln Leu Lys Ile Lys Pro Ile Glu Leu Gly Thr Leu
            275                 280                 285
Cys Ile Pro Glu Phe Pro Val Thr Gly Lys Phe Asp Gly Lys Ala Leu
            290                 295                 300
Gly Glu Arg Ile Gln Lys Pro Ser Lys Phe Phe Leu Glu Ile Ala Glu
305                 310                 315                 320
Leu Val Lys Ser Ala Thr Glu Gly Thr Pro Ser Ser His Lys Gln His
            325                 330                 335
Glu Glu Ser Pro Ala Ser Lys Leu Ala Ser Pro Thr Pro Pro Lys Ser
            340                 345                 350
Pro Phe Gly Ser Leu Ser Leu Leu Lys Lys Lys Leu Met Gln Ser Asn
            355                 360                 365
Pro Leu Arg Asp Pro Phe Ser Pro Leu Asn Ile Asp Leu Gln Ser Glu
            370                 375                 380
His Pro Asp Trp Ser Ala Lys Lys Lys Ser Gln Cys Val Asn Asn Asn
385                 390                 395                 400
Val Gly Pro Ile Glu Ser Arg Gly Cys Glu Asn Thr Asn Ile Met Val
            405                 410                 415
Pro Leu Arg Gly Ser Asp Leu Val His Glu Gln Pro Ile Glu Lys Asn
            420                 425                 430
```

```
Pro Gly Arg Asp Ser Val Lys Thr Gly Pro Asn Gly Ser Arg Ser Gly
        435                 440                 445

Met Glu Gln His Asn Gly Tyr Asp Asp Ile Asp Ala Asn Thr Asn Asp
    450                 455                 460

Asn Leu Asn Met Arg Asn Val Asp Ser His His Glu Ser Asp Gly Leu
465                 470                 475                 480

Asp Lys Val Lys Asp Asp Ser Val Ile Lys Asn Val Leu Lys Ala Leu
            485                 490                 495

Gln Gly Leu Glu Thr Lys Ser Tyr Ile Asp Cys Gln Lys Leu Gln Asp
            500                 505                 510

Ser Glu Val Leu Ala Glu Thr Leu Pro Ser Leu Gln Ala Gln Gly Lys
            515                 520                 525

Ala Val Asp Thr Ala Asn Tyr Thr Ile Glu Thr Ala Val Glu Asp Phe
530                 535                 540

Gly Ser Thr Glu Ile Asp Pro Leu Val Asp Asn Met Leu Pro Glu Thr
545                 550                 555                 560

Ala Pro Ser Ala Glu Gln Asp His Tyr Phe Glu Asp Ser Val Lys Asp
                565                 570                 575

Leu Asn Ser Asp Gln Leu Asn Ser Val Gly Val Glu Val Pro Ser Arg
                580                 585                 590

Asp Val Arg Pro Lys Phe Pro Glu Met Ser Pro Gln His His Lys Gln
            595                 600                 605

Ala Lys Asp Lys Gln Gln Lys Ala Lys Glu Leu Ala Val Gly Arg Arg
            610                 615                 620

Glu Arg Lys His Leu Ser Ser Arg Pro Ser Leu Ala Asp Ala Gly Thr
625                 630                 635                 640

Ser Phe Glu Ser Gly Val Arg Arg Ser Lys Arg Met Lys Thr Arg Pro
                645                 650                 655

Leu Glu Tyr Trp Lys Gly Glu Arg Leu Leu Tyr Gly Arg Val Asp Glu
                660                 665                 670

Gly Leu Lys Leu Val Gly Leu Lys Tyr Ile Ser Pro Gly Lys Gly Ser
            675                 680                 685

Phe Lys Val Lys Ser Tyr Ile Pro Asp Asp Tyr Lys Asp Leu Val Asp
            690                 695                 700

Leu Ala Ala Arg Tyr
705

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Gly
<220> FEATURE:
<221> NAME/KEY: MOD_RES
<222> LOCATION: (4)..(4)
<223> OTHER INFORMATION: Gln, Gly or Pro
<220> FEATURE:
<221> NAME/KEY: MOD_RES
<222> LOCATION: (5)..(5)
<223> OTHER INFORMATION: Gln or Leu
<220> FEATURE:
<221> NAME/KEY: MOD_RES
<222> LOCATION: (8)..(8)
<223> OTHER INFORMATION: Asp or Asn
```

```
<220> FEATURE:
<221> NAME/KEY: MOD_RES
<222> LOCATION: (10)..(10)
<223> OTHER INFORMATION: Leu or Pro
<220> FEATURE:
<221> NAME/KEY: MOD_RES
<222> LOCATION: (12)..(12)
<223> OTHER INFORMATION: Gln or Glu
<220> FEATURE:
<221> NAME/KEY: MOD_RES
<222> LOCATION: (13)..(13)
<223> OTHER INFORMATION: Arg or Thr
<220> FEATURE:
<221> NAME/KEY: MOD_RES
<222> LOCATION: (15)..(15)
<223> OTHER INFORMATION: Asn, His or Pro

<400> SEQUENCE: 5

Glu Ile Xaa Xaa Xaa Val Asp Xaa Met Xaa Pro Xaa Xaa Ala Xaa
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Thr
<220> FEATURE:
<221> NAME/KEY: MOD_RES
<222> LOCATION: (4)..(4)
<223> OTHER INFORMATION: Gln or Pro

<400> SEQUENCE: 6

Glu Xaa Asp Xaa Leu Val Asp Asn Met Leu Pro Glu Thr Ala Pro
1               5                   10                  15

<210> SEQ ID NO 7
<211> LENGTH: 2133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggtgaacg aagctcttat ctccgatccg gtggatcctc tccacagcct tgccggactt     60
tctctactcc caacaacagt tagggtttcc accggcgcct cagtatcagt agactccaaa    120
gacctagagt caattcacaa tttcatgaag tccatggaaa ccaagggtcc tgggctcttg    180
gaggaggcta gggaaattgt ggataacggt gcggagcttt tgaataccaa gtttacaagt    240
ttcatacgat ctaaaggcat tgatggggat cttgcaatca agggaaagga aaggtccag    300 gagagaagac aggacttggg cgtaaaagg gctcgatttt ccctcaagcc tagtacaagt    360
caacctactg tcagcatagc tcctcgttta gatattgatc aactatcaga tccagtggaa    420 ttttttctcag ttgctgaaaa gctagaagtt gctgagaagg aaatagaaag acagaaaggt    480
ggcagtatcc atgatccaga tgtgaataat cccccagcca atgctcggcg tcgtcgacca    540
ggcatcttgg gcaaatcggt gaagtataag caccgtttct catcctccca gcctgagaat    600
gatgatgcat ttatatcatc tcaagagaca ttggaggatg atattctggt ggaacatggt    660
tctcagttgc agaagagct ccatggcctc aatgttgaac tacaagaagc agaactcaca    720
```

```
gggccaataa agaaatcaga aaacagaatc aacaagatac tggatgaatt actgtctggt    780
agtggtgaag atctagaccg ggacatggca gtatccaaat tgcaagagca gttgaagatc    840
aagcccattg aactaggaac tttatgtatt cctgagttcc ctgtgactgg aaagtttgat    900
ggtaaggctc ttggagagag aattcagaag cctagtaagt ttttttttgga gatagcggag    960 ttggttaaaa gtgcaactga gggaacgcca tcctctcaca aacagcatga agaaagtcct   1020
gccagtaaat tagcatcacc cactccacca aaaagtccat ttggttcatt gtctttgttg   1080
aaaaagaaac ttatgcagtc aaatccactg agagatcctt tttcgcctct caacattgat   1140
ctgcaatcag agcatccaga ttggtccgcg aagaagaaat cacaatgtgt aaataataat   1200
gttggaccta ttgaatctcg tggttgtgaa atacaaata ttatggtccc tttaagaggt    1260
tcagacttag tgcatgagca accaattgaa aagaatccag gcagagatag tgtaaaaact   1320
gggccaaatg gatctcgatc tggaatggag caacataatg gctatgatga tattgatgcc   1380
aatactaacg acaacttaaa tatgagaaat gtggattccc accatgagtc tgatgggctt   1440
gacaaagtga aagatgattc agttataaag aatgttttga aggctctaca aggtcttgag   1500
accaaatcct acattgactg tcaaaagctg caggatagtg aagttcttgc tgaaacacta   1560
ccttctcttc aagcccaagg aaaagctgtc gatacagcca attataccat agaaacagct   1620
gttgaggatt ttggatcaac tgaaattgat ccgctgcatg ttaaatatat gctaccagaa   1680
acagcgcctt ctgcagaaca agatcattac tttgaggatt ctgtcaaaga cttaaatagt   1740
gatcaattga actcagtggg agttgaagtt ccttctagag acgtgagacc taaatttccg   1800
gagatgagcc ctcagcatca aagcaggca aagataagc aacagaaagc aaaggaactt    1860
gctgttggaa ggcgtgaaag aaaacatctt tcttctaggc caagtctagc agatgctggc   1920
acatcatttg aaagtggggt tagacgaagc aaacgaatga agacaaggcc tttggaatat   1980
tggaaaggcg aaagattatt atatggacgg gttgatgagg gtttgaagct tgttggcttg   2040
aaatacatct ctccgggaaa gggatcattt aaggtgaagt cttacattcc tgatgactac   2100
aaagacctag ttgatttggc agctcgctat tga                               2133
```

<210> SEQ ID NO 8
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Val Asn Glu Ala Leu Ile Ser Asp Pro Val Asp Pro Leu His Ser
1               5                   10                  15

Leu Ala Gly Leu Ser Leu Leu Pro Thr Thr Val Arg Val Ser Thr Gly
            20                  25                  30

Ala Ser Val Ser Val Asp Ser Lys Asp Leu Glu Ser Ile His Asn Phe
        35                  40                  45

Met Lys Ser Met Glu Thr Lys Gly Pro Gly Leu Leu Glu Glu Ala Arg
    50                  55                  60

Glu Ile Val Asp Asn Gly Ala Glu Leu Leu Asn Thr Lys Phe Thr Ser
65                  70                  75                  80

Phe Ile Arg Ser Lys Gly Ile Asp Gly Asp Leu Ala Ile Lys Gly Lys
                85                  90                  95

Glu Lys Val Gln Glu Arg Arg Pro Gly Leu Gly Arg Lys Arg Ala Arg
            100                 105                 110

```
Phe Ser Leu Lys Pro Ser Thr Ser Gln Pro Thr Val Ser Ile Ala Pro
            115                 120                 125

Arg Leu Asp Ile Asp Gln Leu Ser Asp Pro Val Glu Phe Phe Ser Val
    130                 135                 140

Ala Glu Lys Leu Glu Val Ala Glu Lys Glu Ile Glu Arg Gln Lys Gly
145                 150                 155                 160

Gly Ser Ile His Asp Pro Asp Val Asn Asn Pro Pro Ala Asn Ala Arg
                165                 170                 175

Arg Arg Arg Pro Gly Ile Leu Gly Lys Ser Val Lys Tyr Lys His Arg
            180                 185                 190

Phe Ser Ser Gln Pro Glu Asn Asp Asp Ala Phe Ile Ser Ser Gln
            195                 200                 205

Glu Thr Leu Glu Asp Asp Ile Leu Val Glu His Gly Ser Gln Leu Pro
    210                 215                 220

Glu Leu His Gly Leu Asn Val Glu Leu Gln Glu Ala Glu Leu Thr
225                 230                 235                 240

Gly Pro Ile Lys Lys Ser Glu Asn Arg Ile Asn Lys Ile Leu Asp Glu
                245                 250                 255

Leu Leu Ser Gly Ser Gly Glu Asp Leu Asp Arg Asp Met Ala Val Ser
            260                 265                 270

Lys Leu Gln Glu Gln Leu Lys Ile Lys Pro Ile Glu Leu Gly Thr Leu
            275                 280                 285

Cys Ile Pro Glu Phe Pro Val Thr Gly Lys Phe Asp Gly Lys Ala Leu
            290                 295                 300

Gly Glu Arg Ile Gln Lys Pro Ser Lys Phe Leu Glu Ile Ala Glu
305                 310                 315                 320

Leu Val Lys Ser Ala Thr Glu Gly Thr Pro Ser Ser His Lys Gln His
                325                 330                 335

Glu Glu Ser Pro Ala Ser Lys Leu Ala Ser Pro Thr Pro Lys Ser
            340                 345                 350

Pro Phe Gly Ser Leu Ser Leu Leu Lys Lys Lys Leu Met Gln Ser Asn
            355                 360                 365

Pro Leu Arg Asp Pro Phe Ser Pro Leu Asn Ile Asp Leu Gln Ser Glu
    370                 375                 380

His Pro Asp Trp Ser Ala Lys Lys Ser Gln Cys Val Asn Asn Asn
385                 390                 395                 400

Val Gly Pro Ile Glu Ser Arg Gly Cys Glu Asn Thr Asn Ile Met Val
                405                 410                 415

Pro Leu Arg Gly Ser Asp Leu Val His Glu Gln Pro Ile Glu Lys Asn
            420                 425                 430

Pro Gly Arg Asp Ser Val Lys Thr Gly Pro Asn Gly Ser Arg Ser Gly
            435                 440                 445

Met Glu Gln His Asn Gly Tyr Asp Asp Ile Asp Ala Asn Thr Asn Asp
    450                 455                 460

Asn Leu Asn Met Arg Asn Val Asp Ser His His Glu Ser Asp Gly Leu
465                 470                 475                 480

Asp Lys Val Lys Asp Asp Ser Val Ile Lys Asn Val Leu Lys Ala Leu
                485                 490                 495

Gln Gly Leu Glu Thr Lys Ser Tyr Ile Asp Cys Gln Lys Leu Gln Asp
            500                 505                 510

Ser Glu Val Leu Ala Glu Thr Leu Pro Ser Leu Gln Ala Gln Gly Lys
            515                 520                 525
```

```
Ala Val Asp Thr Ala Asn Tyr Thr Ile Glu Thr Ala Val Glu Asp Phe
        530                 535                 540

Gly Ser Thr Glu Ile Asp Pro Leu His Val Lys Tyr Met Leu Pro Glu
545                 550                 555                 560

Thr Ala Pro Ser Ala Glu Gln Asp His Tyr Phe Glu Asp Ser Val Lys
                565                 570                 575

Asp Leu Asn Ser Asp Gln Leu Asn Ser Val Gly Val Glu Val Pro Ser
            580                 585                 590

Arg Asp Val Arg Pro Lys Phe Pro Glu Met Ser Pro Gln His His Lys
        595                 600                 605

Gln Ala Lys Asp Lys Gln Lys Ala Lys Glu Leu Ala Val Gly Arg
610                 615                 620

Arg Glu Arg Lys His Leu Ser Ser Arg Pro Ser Leu Ala Asp Ala Gly
625                 630                 635                 640

Thr Ser Phe Glu Ser Gly Val Arg Arg Ser Lys Arg Met Lys Thr Arg
                645                 650                 655

Pro Leu Glu Tyr Trp Lys Gly Arg Leu Leu Tyr Gly Arg Val Asp
            660                 665                 670

Glu Gly Leu Lys Leu Val Gly Leu Lys Tyr Ile Ser Pro Gly Lys Gly
        675                 680                 685

Ser Phe Lys Val Lys Ser Tyr Ile Pro Asp Tyr Lys Asp Leu Val
690                 695                 700

Asp Leu Ala Ala Arg Tyr
705                 710

<210> SEQ ID NO 9
<211> LENGTH: 2130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggtgaacg aagctcttat ctccgatccg gtggatcctc tccacagcct tgccggactt      60
tctctactcc caacaacagt tagggtttcc accggcgcct cagtatcagt agactccaaa     120
gacctagagt caattcacaa tttcatgaag tccatggaaa ccaagggtcc tgggctcttg     180
gaggaggcta gggaaattgt ggataacggt gcggagcttt tgaataccaa gtttacaagt     240
ttcatacgat ctaaaggcat tgatggggat cttgcaatca agggaaagga gaaggtccag     300
gagagaagac aggacttggg gcgtaaaagg gctcgatttt ccctcaagcc tagtacaagt     360
caacctactg tcagcatagc tcctcgttta gatattgatc aactatcaga tccagtggaa     420
tttttctcag ttgctgaaaa gctagaagtt gctgagaagg aaatagaaag acagaaaggt     480
ggcagtatcc atgatccaga tgtgaataat ccccagccaa tgctcggcg tcgtcgacca     540 ggcatcttgg gcaaatcggt gaagtataag caccgtttct catcctccca gcctgagaat     600
gatgatgcat ttatatcatc tcaagagaca ttggaggatg atattctggt ggaacatggt     660
tctcagttgc cagaagagct ccatggcctc aatgttgaac tacaagaagc agaactcaca     720
gggccaataa agaaatcaga aacagaatc aacaagatac tggatgaatt actgtctggt     780
agtggtgaag atctagaccg ggacatggca gtatccaaat gcaagagca gttgaagatc     840 aagcccattg aactaggaac tttatgtatt cctgagttcc ctgtgactgg aaagtttgat     900
ggtaaggctc ttggagagag aattcagaag cctagtaagt tttttttgga gatagcggag     960
```

```
ttggttaaaa gtgcaactga gggaacgcca tcctctcaca aacagcatga agaaagtcct   1020
gccagtaaat tagcatcacc cactccacca aaaagtccat ttggttcatt gtctttgttg   1080
aaaaagaaac ttatgcagtc aaatccactg agagatcctt tttcgcctct caacattgat   1140
ctgcaatcag agcatccaga ttggtccgcg aagaagaaat cacaatgtgt aaataataat   1200
gttggaccta ttgaatctcg tggttgtgaa aatacaaata ttatggtccc tttaagaggt   1260
tcagacttag tgcatgagca accaattgaa aagaatccag gcagagatag tgtaaaaact   1320
gggccaaatg gatctcgatc tggaatggag caacataatg gctatgatga tattgatgcc   1380
aatactaacg acaacttaaa tatgagaaat gtggattccc accatgagtc tgatgggctt   1440
gacaaagtga agatgattc agttataaag aatgttttga aggctctaca aggtcttgag   1500
accaaatcct acattgactg tcaaaagctg caggatagtg aagttcttgc tgaaacacta   1560
ccttctcttc aagcccaagg aaaagctgtc gatacagcca attataccat agaaacagct   1620
gttgaggatt ttggatcaac tgaaattgat ccgctggttg acaatgtgct accagaaaca   1680
gcgccttctg cagaacaaga tcattacttt gaggattctg tcaaagactt aaatagtgat   1740
caattgaact cagtgggagt tgaagttcct tctagagacg tgagacctaa atttccggag   1800
atgagccctc agcatcacaa gcaggcaaaa gataagcaac agaaagcaaa ggaacttgct   1860
gttggaaggc gtgaaagaaa acatctttct tctaggccaa gtctagcaga tgctggcaca   1920
tcatttgaaa gtggggttag acgaagcaaa cgaatgaaga caaggccttt ggaatattgg   1980
aaaggcgaaa gattattata tggacgggtt gatgagggtt tgaagcttgt tggcttgaaa   2040
tacatctctc cggaaaaggg atcatttaag gtgaagtctt acattcctga tgactacaaa   2100
gacctagttg atttggcagc tcgctattga                                     2130
```

<210> SEQ ID NO 10
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Val Asn Glu Ala Leu Ile Ser Asp Pro Val Asp Pro Leu His Ser
1               5                   10                  15

Leu Ala Gly Leu Ser Leu Leu Pro Thr Thr Val Arg Val Ser Thr Gly
                20                  25                  30

Ala Ser Val Ser Val Asp Ser Lys Asp Leu Glu Ser Ile His Asn Phe
            35                  40                  45

Met Lys Ser Met Glu Thr Lys Gly Pro Gly Leu Leu Glu Glu Ala Arg
        50                  55                  60

Glu Ile Val Asp Asn Gly Ala Glu Leu Leu Asn Thr Lys Phe Thr Ser
65                  70                  75                  80

Phe Ile Arg Ser Lys Gly Ile Asp Gly Asp Leu Ala Ile Lys Gly Lys
                85                  90                  95

Glu Lys Val Gln Glu Arg Arg Pro Gly Leu Gly Arg Lys Arg Ala Arg
            100                 105                 110

Phe Ser Leu Lys Pro Ser Thr Ser Gln Pro Thr Val Ser Ile Ala Pro
        115                 120                 125

Arg Leu Asp Ile Asp Gln Leu Ser Asp Pro Val Glu Phe Phe Ser Val
    130                 135                 140

Ala Glu Lys Leu Glu Val Ala Glu Lys Glu Ile Glu Arg Gln Lys Gly
```

```
            145                 150                 155                 160
        Gly Ser Ile His Asp Pro Asp Val Asn Asn Pro Ala Asn Ala Arg
                        165                 170                 175
        Arg Arg Arg Pro Gly Ile Leu Gly Lys Ser Val Lys Tyr Lys His Arg
                        180                 185                 190
        Phe Ser Ser Ser Gln Pro Glu Asn Asp Asp Ala Phe Ile Ser Ser Gln
                        195                 200                 205
        Glu Thr Leu Glu Asp Asp Ile Leu Val Glu His Gly Ser Gln Leu Pro
                        210                 215                 220
        Glu Glu Leu His Gly Leu Asn Val Glu Leu Gln Glu Ala Glu Leu Thr
        225                 230                 235                 240
        Gly Pro Ile Lys Lys Ser Glu Asn Arg Ile Asn Lys Ile Leu Asp Glu
                        245                 250                 255
        Leu Leu Ser Gly Ser Gly Glu Asp Leu Asp Arg Asp Met Ala Val Ser
                        260                 265                 270
        Lys Leu Gln Glu Gln Leu Lys Ile Lys Pro Ile Glu Leu Gly Thr Leu
                        275                 280                 285
        Cys Ile Pro Glu Phe Pro Val Thr Gly Lys Phe Asp Gly Lys Ala Leu
                        290                 295                 300
        Gly Glu Arg Ile Gln Lys Pro Ser Lys Phe Phe Leu Glu Ile Ala Glu
        305                 310                 315                 320
        Leu Val Lys Ser Ala Thr Glu Gly Thr Pro Ser Ser His Lys Gln His
                        325                 330                 335
        Glu Glu Ser Pro Ala Ser Lys Leu Ala Ser Pro Thr Pro Pro Lys Ser
                        340                 345                 350
        Pro Phe Gly Ser Leu Ser Leu Leu Lys Lys Lys Leu Met Gln Ser Asn
                        355                 360                 365
        Pro Leu Arg Asp Pro Phe Ser Pro Leu Asn Ile Asp Leu Gln Ser Glu
                        370                 375                 380
        His Pro Asp Trp Ser Ala Lys Lys Lys Ser Gln Cys Val Asn Asn Asn
        385                 390                 395                 400
        Val Gly Pro Ile Glu Ser Arg Gly Cys Glu Asn Thr Asn Ile Met Val
                        405                 410                 415
        Pro Leu Arg Gly Ser Asp Leu Val His Glu Gln Pro Ile Glu Lys Asn
                        420                 425                 430
        Pro Gly Arg Asp Ser Val Lys Thr Gly Pro Asn Gly Ser Arg Ser Gly
                        435                 440                 445
        Met Glu Gln His Asn Gly Tyr Asp Asp Ile Asp Ala Asn Thr Asn Asp
            450                 455                 460
        Asn Leu Asn Met Arg Asn Val Asp Ser His His Glu Ser Asp Gly Leu
        465                 470                 475                 480
        Asp Lys Val Lys Asp Asp Ser Val Ile Lys Asn Val Leu Lys Ala Leu
                        485                 490                 495
        Gln Gly Leu Glu Thr Lys Ser Tyr Ile Asp Cys Gln Lys Leu Gln Asp
                        500                 505                 510
        Ser Glu Val Leu Ala Glu Thr Leu Pro Ser Leu Gln Ala Gln Gly Lys
                        515                 520                 525
        Ala Val Asp Thr Ala Asn Tyr Thr Ile Glu Thr Ala Val Glu Asp Phe
                        530                 535                 540
        Gly Ser Thr Glu Ile Asp Pro Leu Val Asp Asn Val Leu Pro Glu Thr
        545                 550                 555                 560
        Ala Pro Ser Ala Glu Gln Asp His Tyr Phe Glu Asp Ser Val Lys Asp
                        565                 570                 575
```

```
Leu Asn Ser Asp Gln Leu Asn Ser Val Gly Val Glu Val Pro Ser Arg
                580                 585                 590

Asp Val Arg Pro Lys Phe Pro Glu Met Ser Pro Gln His His Lys Gln
            595                 600                 605

Ala Lys Asp Lys Gln Gln Lys Ala Lys Glu Leu Ala Val Gly Arg Arg
        610                 615                 620

Glu Arg Lys His Leu Ser Ser Arg Pro Ser Leu Ala Asp Ala Gly Thr
625                 630                 635                 640

Ser Phe Glu Ser Gly Val Arg Arg Ser Lys Arg Met Lys Thr Arg Pro
                645                 650                 655

Leu Glu Tyr Trp Lys Gly Glu Arg Leu Leu Tyr Gly Arg Val Asp Glu
            660                 665                 670

Gly Leu Lys Leu Val Gly Leu Lys Tyr Ile Ser Pro Gly Lys Gly Ser
        675                 680                 685

Phe Lys Val Lys Ser Tyr Ile Pro Asp Asp Tyr Lys Asp Leu Val Asp
    690                 695                 700

Leu Ala Ala Arg Tyr
705

<210> SEQ ID NO 11
<211> LENGTH: 6220
<212> TYPE: DNA
<213> ORGANISM: Solanum lycopersicum

<400> SEQUENCE: 11
atggtgaacg aagctcttat ctccgatccg gtggatcctc tccacagcct tgccggactt      60
tctctactcc caacaacagt tagggtttcc accggcgcct cagtatcagt agactccaaa     120
gacctagagt caattcacaa tttcatgaag tccatggtaa ttttccgttt gttttttcttc    180 acttctttag atttctagct cttttataga tcttacatgt taatttagag gagaagtagt     240
gttaatgtcg ttactatgga gttttcgctg ttcttcggtt cgttcctgca ctgaactcca     300
acttacaatt agtacaatta aaatggagtc taacttacat aattgttgta gtttgtccgt     360
ttacaattgg ctagttatat gattttggat gatgttgttc tccttcttta tgataataaa     420
aggaaaccaa gggtcctggg ctcttggagg aggctaggga aattgtggat aacggtgcgg     480
agcttttgaa taccaagttt acaagtttca tacgatctaa aggcattgat ggggatcttg     540
caatcaaggg aaaggagaag gtccaggaga aagaccagg acttgggcgt aaaagggctc     600
gattttccct caagcctagt acaaggtaaa ttatagacag ttttttcttta ttctctaatt    660 agatcctatt gaaaccatgg tgttagctta ccttgctatg cagtcaacct actgtcagca     720
tagctcctcg tttagatatt gatcaactat cagatccagt ggaattttc tcagttgctg      780 aaaagctaga aggtgatttt gtttcttttg ttatctctta actatctgct tgcaaatttg     840
atccgtcggc aactaaaaac agtatatatt atacttagaa aaataacagt tttagtgttt     900
tacatatggt gaacttacag ttgctgagaa ggaaatagaa agacagaaag gtggcagtat     960
ccatgatcca gatgtgaata atccccccagc caatgctcgg cgtcgtcgac caggcatctt    1020
ggggtacacc tagatactct ttgttttttt acatggaaat gcctgtccta cctttatcgt    1080
cctctcaact tgttgttgca cctttttaga gttctctttt ctgtctcagc aaatcggtga    1140
agtataagca ccgttttctca tcctcccagc ctgagaatga tgatgcattt atatcatctc   1200
aagagacatt ggaggatgat attctggtgg aacatggttc tcagttgcca gaagagctcc    1260
atggcctcaa tgttgaacta caagaagcag aactcacagg ttattgggtt aactaatca     1320
```

-continued

```
agatagatac cttctgattt ctagattata tttttaactt ctctatgagc agaatgtcat    1380
ttcagaagtg ataattgctt tccaattcaa cagggccaat aaagaaatca gaaaacagaa    1440
tcaacaagat actggatgaa ttactgtctg gtagtggtga agatctagac cgggacatgg    1500
cagtatccaa attgcaagag cagttgaaga tcaagcccat tgaactagga actttatgta    1560
ttcctgagtt ccctgtgact ggaaagtttg atggtaaggc tcttggagag agaattcaga    1620
agcctagtaa gttttttttg gagatagcgg agttggttaa aagtgcaact gagggaacgc    1680
catcctctca caaacagcat gaagaaagtc ctgccagtaa attagcatca cccactccac    1740
caaaaagtcc atttggttca ttgtctttgt tgaaaaagaa acttatgcag tcaaatccac    1800
tgagagatcc ttttcgcct ctcaacattg atctgcaatc agagcatcca gattggtccg    1860
cgaagaagaa atcacaatgt gtaaataata atgttggacc tattgaatct cgtggttgtg    1920
aaaatacaaa tattatggtc cctttaagag gttcagactt agtgcatgag caaccaattg    1980
aaaagaatcc aggcagagat agtgtaaaaa ctgggccaaa tggatctcga tctggaatgg    2040
agcaacataa tggctatgat gatattgatg ccaatactaa cgacaactta aatatgagaa    2100
atgtggattc ccaccatgag tctgatgggc ttgacaaagt gaaagatgat tcagttataa    2160
agaatgtttt gaaggctcta caaggtcttg agaccaaatc ctacattgac tgtcaaaagc    2220
tgcaggatag tgaagttctt gctgaaacac taccttctct tcaagcccaa ggaaaagctg    2280
tcgatacagc caattatacc atagaaacag ctgttgagga ttttggatca actgaaattg    2340
atccgctggc aagtctatcc acttcttact attatatgct gcatttgata cattattcca    2400
ggagttataa ttcaaactgt gacattttt cattcatacg tcattagcag gttgacaata    2460
tgctaccaga aacagcgcct tctgcagaac aagatcatta ctttgaggat tctgtcaaag    2520
acttaaatag tggtgagatt ctattttgga tgatttttt tatgccaagt catcatttat    2580
gaagatgcga catttgagca ttgtctattt cttgctagat tcttttgtat acacaaattt    2640
ttgtacgtat tcaaaacaat cttttttatg ttttaacaca tcgcttgagt tttacccgga    2700
atcatctgca gtcaactatt cgttttttga ccacttatat tcaactctta actgggtgat    2760
tcatggtact ggaactggac aattcttagg tctgctacag gctatagatt aaggtgtgaa    2820
gtgctggaat ttagtatacg aagaagtaac tgcccatgtt tgccagaaat tgtactgcaa    2880
tagaccaata ccttggttgc ttggaatgtt ctgtcataac ttctctttcc ttttcctttt    2940
catctctggt tttttaatgg gaggatgcat gtgatgcatc tttataaaaa atagatgtgt    3000
agaattttga acttgtagtt gtcaagaatc atgacttttg atcttcattt tttttaaaaa    3060
aggtaatgac tcaattgaga agatggggat aacgctctat cattgtatac catattgaaa    3120
accttacaaa agatatggtt ctcagcaaaa acacatgcat cactatttat catgatgttt    3180
taagtactcc aaaagtaaca agatttgtct aatatgtttg aacttcactt ctatctttcg    3240
agcatcctgt taggtactag atataaatta acgagacgta agtttgtact ggtacatgca    3300
agttattgct gcattctgat gttctattgt ggttatagga gcattaaggt gtctatagtg    3360
tcacgagcaa agcattaggg atgattaatc attaaagtaa cccatgtact gatagcaaaa    3420
gatcatatgc cacatattga tacctattgc gtagtcacaa actcaaccct gctcttcaga    3480
gtcagaaggc gcttccactt aacccagttt ataattggtt acttgcttta ctttcttta    3540 tttataaagt aatatgctac ctccaaatat gaacttcagc tgctgaaatc attctcacat    3600
tgatcacctt ctcttttgca atggttcttt gagcttgtgt cactctttac attataaagt    3660
```

```
tgtcatagta cctgtgcatt ctgaatatat gttgttttc ttgaacatat agctagttat   3720
tttacccact ctactttgca tatcttaact agtaataaca gtctaaagtt tggaaagaac   3780
ttgagaacct tggtatcttt atacagatca attgaactca gtgggagttg aagttccttc   3840
tagagacgtg agacctaaat ttccggagat gagccctcag catcacaagc aggttgcctc   3900
ctttcttgaa tggtccttca ttattttta tttatatagg aaactcaaag tgccaagtta   3960
atcctttggt attcacacac acacatacac actctctctc tctctctccc aaaagcaaat   4020
aatgatggca gggtttaagg ggtcaaaata cttgcgacat acaaaagcct ggtatttgag   4080
tggagaagtg agcacaatgt ccaaaattta tgctccatac agtttcaaac catttgccat   4140
tggtcctcag agtttttcgg atcgaaaaca attattgtta aagagtctac aatatcaaag   4200
tcagtaaaaa tcgtctgatt ctccaattgt aactgtaaat tagaagacag taaagctgat   4260
tgcttgtatg taaacaaatc tgtagatgcc taaacactag atagggtttt gtgcaaaaac   4320
atatcgcaat tcccaaattt aaaaaaaaac tagcatgaac tgcgtttgat aaccatgatt   4380 attttttgt tcttttgaaa aaagtgcaat gatgtgactg atttaagttg ccaaatgtgt   4440
tgatttctgt ctagggttag dacatttta agctgtctac tgaaatgacc ctctgatatt   4500
attggtgtta aaatttgaca accagtctgt ataagagtcg atatttctga cgtgacagtg   4560
gatattgaat gatattgatt gaacacatta atagttttag cccatcatgt ctcctaattt   4620
tgggtttaca tgtgaatgct tgtgctcttt gcagttgtat ttctttacct gtattggtta   4680
tactgattga catgcaatat ttctgatgca ttaggcaaaa gataagcaac agaaagcaaa   4740
ggaacttgct gttggaaggc gtgaaagaaa acatctttct tctaggccaa gtctagcagg   4800
tttttactct tgcgactatg gggatgtctt catttgaagt ctttcatttg tgtttttgat   4860
aaagaatttc atgaatttga cagatgctgg cacatcattt gaaagtgggg ttagacgaag   4920
caaacgaatg aagacaaggc ctttggaata ttggaaaggc gaaagattat tatatggacg   4980
ggttgatgag ggtgagtatt gtcttgtaaa ttcttgtgtt gttactttgc tgggtttctg   5040
ttggattcat ttgttagact tgggtgatag ggtaataatt catcttgatc ctcaaatcta   5100
gtttttcttt ttttggcgcg tgcgtgtgag agagagatgt gtgaaactag gccacaacat   5160
gctagacttt atacttatag tcttgggaag gtaactactc aaggatattt tcttgtcctt   5220
tagataggat gtttatcaca ctaaacgacc taatattgga gaggttggtg gtaacatatg   5280
cacattttgc atagaactct acaagacagc gaaagaaaat attagggacg gcttagctat   5340
tagagaagca tggtaactag gttacttgca tgtctgctaa gagagtgcaa gttagggtat   5400
cagaatctag ttttcaggga ttagtttcgt acttggtcaa gtctcttcca gcaggagatt   5460
aacttagtta aggctctcct agttggtgac ttactagctc agaatactca ttggaacttg   5520
aattacagga aattaggtaa tttgatcctc aatattttg tgcttgaaaa tcatcaccga   5580
gataatgtag tagacttatt tcctaaatca gccaacatgc tgaattccat aaattgtcaa   5640
gcacaaaatt gaagtaattt ttgaaaacta atcatttcaa ttttggatat ttcacttaag   5700
ggatgccttt agttactttg gcaagtttat tctagttgag cactctctta tagaaagtag   5760
aaacttgagc cataggaact taggtagttt aacccatcat attttcttgc ttgaaaattt   5820
atcattgaga taatagatca gacgtagttc atatatcatc caacttgctg aattccataa   5880
atggtcaaca aaaattaaag taattcgaaa gtgattgttt cagtgtagaa gcaaattgca   5940
gccaacattg agtagcagct tttggatatt acttctatcg taactagcaa ttcaatacat   6000
taaagcatat gctaaacaca atgaacttat cttttcgact ggttgtttct atgtttaacc   6060
```

```
tgtggagaaa acaacagatt tagtatatcc gtgtgtttct gttgcaggtt tgaagcttgt    6120
tggcttgaaa tacatctctc cgggaaaggg atcatttaag gtgaagtctt acattcctga    6180
tgactacaaa gacctagttg atttggcagc tcgctattga                          6220

<210> SEQ ID NO 12
<211> LENGTH: 6220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggtgaacg aagctcttat ctccgatccg gtggatcctc tccacagcct tgccggactt     60
tctctactcc caacaacagt tagggtttcc accggcgcct cagtatcagt agactccaaa    120
gacctagagt caattcacaa tttcatgaag tccatggtaa ttttccgttt gttttttcttc   180 acttctttag atttctagct cttttataga tcttacatgt taatttagag gagaagtagt    240
gttaatgtcg ttactatgga gttttcgctg ttcttcggtt cgttcctgca ctgaactcca    300
acttacaatt agtacaatta aaatggagtc taacttacat aattgttgta gtttgtccgt    360
ttacaattgg ctagttatat gattttggat gatgttgttc ccttctttta tgataataaa    420
aggaaaccaa gggtcctggg ctcttggagg aggctaggga aattgtggat aacggtgcgg    480
agcttttgaa taccaagttt acaagtttca tacgatctaa aggcattgat ggggatcttg    540
caatcaaggg aaaggagaag gtccaggaga gaagaccagg acttgggcgt aaaagggctc    600
gattttccct caagcctagt acaaggtaaa ttatagacag ttttttcttta ttctctaatt    660 agatcctatt gaaaccatgg tgttagctta ccttgctatg cagtcaacct actgtcagca    720
tagctcctcg tttagatatt gatcaactat cagatccagt ggaattttc tcagttgctg     780 aaaagctaga aggtgatttt gtttcttttg ttatctctta actatctgct tgcaaatttg    840
atccgtcggc aactaaaaac agtatatatt atacttagaa aaataacagt tttagtgttt    900
tacatatggt gaacttacag ttgctgagaa ggaaatagaa agacagaaag gtggcagtat    960
ccatgatcca gatgtgaata atccccccagc caatgctcgg cgtcgtcgac caggcatctt   1020
ggggtacacc tagatactct ttgttttttt acatggaaat gcctgtccta cctttatcgt   1080
cctctcaact tgttgttgca ccttttttaga gttctctttt ctgtctcagc aaatcggtga   1140
agtataagca ccgtttctca tcctcccagc ctgagaatga tgatgcattt atatcatctc    1200
aagagacatt ggaggatgat attctggtgg aacatggttc tcagttgcca gaagagctcc    1260
atggcctcaa tgttgaacta caagaagcag aactcacagg ttattgggtt taactaatca    1320
agatagatac cttctgattt ctagattata tttttaactt ctctatgagc agaatgtcat    1380
ttcagaagtg ataattgctt tccaattcaa cagggccaat aaagaaatca gaaacagaa     1440 tcaacaagat actggatgaa ttactgtctg gtagtggtga agatcctagac cgggacatgg    1500 cagtatccaa attgcaagag cagttgaaga tcaagcccat tgaactagga actttatgta   1560
ttcctgagtt ccctgtgact ggaaagtttg atggtaaggc tcttggagag agaattcaga   1620
agcctagtaa gttttttttg gagatagcgg agttggttaa aagtgcaact gagggaacgc    1680
catcctctca caaacagcat gaagaaagtc ctgccagtaa attagcatca cccactccac    1740
caaaaagtcc atttggttca ttgtctttgt tgaaaaagaa acttatgcag tcaaatccac    1800
tgagagatcc ttttttcgcct ctcaacattg atctgcaatc agagcatcca gattggtccg   1860
```

```
cgaagaagaa atcacaatgt gtaaataata atgttggacc tattgaatct cgtggttgtg   1920
aaaatacaaa tattatggtc cctttaagag gttcagactt agtgcatgag caaccaattg   1980
aaaagaatcc aggcagagat agtgtaaaaa ctgggccaaa tggatctcga tctggaatgg   2040
agcaacataa tggctatgat gatattgatg ccaatactaa cgacaactta aatatgagaa   2100
atgtggattc ccaccatgag tctgatgggc ttgacaaagt gaaagatgat tcagttataa   2160
agaatgtttt gaaggctcta caaggtcttg agaccaaatc ctacattgac tgtcaaaagc   2220
tgcaggatag tgaagttctt gctgaaacac taccttctct tcaagcccaa ggaaaagctg   2280
tcgatacagc caattatacc atagaaacag ctgttgagga ttttggatca actgaaattg   2340
atccgctggc aagtctatcc acttcttact attatatgct gcatttgata cattattcca   2400
ggagttataa ttcaaactgt gacattttt cattcatacg tcattagcat gttaaatata   2460
tgctaccaga aacagcgcct tctgcagaac aagatcatta ctttgaggat tctgtcaaag   2520
acttaaatag tggtgagatt ctattttgga tgatttttt tatgccaagt catcattat   2580 gaagatgcga catttgagca ttgtctattt cttgctagat tcttttgtat acacaaattt   2640
ttgtacgtat tcaaaacaat cttttttatg ttttaacaca tcgcttgagt tttacccgga   2700
atcatctgca gtcaactatt cgttttttga ccacttatat tcaactctta actgggtgat   2760
tcatggtact ggaactggac aattcttagg tctgctacag gctatagatt aaggtgtgaa   2820
gtgctggaat ttagtatacg aagaagtaac tgcccatgtt gccagaaat tgtactgcaa   2880 tagaccaata ccttggttgc ttggaatgtt ctgtcataac ttctctttcc ttttccttt   2940 catctctggt ttttaatgg gaggatgcat gtgatgcatc tttataaaaa atagatgtgt   3000
agaattttga acttgtagtt gtcaagaatc atgacttttg atcttcattt tttttaaaaa   3060
aggtaatgac tcaattgaga agatggggat aacgctctat cattgtatac catattgaaa   3120
accttacaaa agatatggtt ctcagcaaaa acacatgcat cactatttat catgatgttt   3180
taagtactcc aaaagtaaca agatttgtct aatatgtttg aacttcactt ctatctttcg   3240
agcatcctgt taggtactag atataaatta acgagacgta agtttgtact ggtacatgca   3300
agttattgct gcattctgat gttctattgt ggttatagga gcattaaggt gtctatagtg   3360
tcacgagcaa agcattaggg atgattaatc attaaagtaa cccatgtact gatagcaaaa   3420
gatcatatgc cacatattga tacctattgc gtagtcacaa actcaaccct gctcttcaga   3480
gtcagaaggc gcttccactt aacccagttt ataattggtt acttgcttta ctttctttta   3540
tttataaagt aatatgctac ctccaaatat gaacttcagc tgctgaaatc attctcacat   3600
tgatcacctt ctcttttgca atggttcttt gagcttgtgt cactctttac attataaagt   3660
tgtcatagta cctgtgcatt ctgaatatat gttgttttc ttgaacatat agctagttat   3720
tttacccact ctactttgca tatcttaact agtaataaca gtctaaagtt tggaaagaac   3780
ttgagaacct tggtatcttt atacagatca attgaactca gtgggagttg aagttccttc   3840
tagagacgtg agacctaaat ttccggagat gagccctcag catcacaagc aggttgcctc   3900
ctttcttgaa tggtccttca ttattttta tttatatagg aaactcaaag tgccaagtta   3960
atcctttggt attcacacac acacatacac actctctctc tctctctccc aaaagcaaat   4020
aatgatggca gggtttaagg ggtcaaaata cttgcgacat acaaaagcct ggtatttgag   4080
tggagaagtg agcacaatgt ccaaaattta tgctccatac agtttcaaac catttgccat   4140
tggtcctcag agttttcgg atcgaaaaca attattgtta aagagtctac aatatcaaag   4200
```

| | | | | |
|---|---|---|---|---|
| tcagtaaaaa | tcgtctgatt | ctccaattgt | aactgtaaat | tagaagacag taaagctgat | 4260 |
| tgcttgtatg | taaacaaatc | tgtagatgcc | taaacactag | gataggggttt gtgcaaaaac | 4320 |
| atatcgcaat | tcccaaattt | aaaaaaaaac | tagcatgaac | tgcgtttgat aaccatgatt | 4380 |
| atttttttgt | tcttttgaaa | aaagtgcaat | gatgtgactg | atttaagttg ccaaatgtgt | 4440 |
| tgatttctgt | ctagggttag | gacatttaa | agctgtctac | tgaaatgacc ctctgatatt | 4500 |
| attggtgtta | aaatttgaca | accagtctgt | ataagagtcg | atatttctga cgtgacagtg | 4560 |
| gatattgaat | gatattgatt | gaacacatta | atagtttag | cccatcatgt ctcctaattt | 4620 |
| tgggtttaca | tgtgaatgct | tgtgctcttt | gcagttgtat | ttctttacct gtattggtta | 4680 |
| tactgattga | catgcaatat | ttctgatgca | ttaggcaaaa | gataagcaac agaaagcaaa | 4740 |
| ggaacttgct | gttggaaggc | gtgaaagaaa | acatctttct | tctaggccaa gtctagcagg | 4800 |
| ttttactct | tgcgactatg | gggatgtctt | catttgaagt | ctttcatttg tgttttgat | 4860 |
| aaagaatttc | atgaatttga | cagatgctgg | cacatcattt | gaaagtgggg ttagacgaag | 4920 |
| caaacgaatg | aagacaaggc | ctttggaata | ttggaaaggc | gaaagattat tatatggacg | 4980 |
| ggttgatgag | ggtgagtatt | gtcttgtaaa | ttcttgtgtt | gttactttgc tgggtttctg | 5040 |
| ttggattcat | ttgttagact | tgggtgatag | gtaataatt | catcttgatc ctcaaatcta | 5100 |
| gtttttcttt | ttttggcgcg | tgcgtgtgag | agagagatgt | gtgaaactag gccacaacat | 5160 |
| gctagacttt | atacttatag | tcttgggaag | gtaactactc | aaggatattt tcttgtcctt | 5220 |
| tagataggat | gtttatcaca | ctaaacgacc | taatattgga | gaggttggtg gtaacatatg | 5280 |
| cacattttgc | atagaactct | acaagacagc | gaaagaaaat | attagggacg gcttagctat | 5340 |
| tagagaagca | tggtaactag | gttacttgca | tgtctgctaa | gagagtgcaa gttagggtat | 5400 |
| cagaatctag | ttttcaggga | ttagtttcgt | acttggtcaa | gtctcttcca gcaggagatt | 5460 |
| aacttagtta | aggctctcct | agttggtgac | ttactagctc | agaatactca ttggaacttg | 5520 |
| aattacagga | aattaggtaa | tttgatcctc | aatattttg | tgcttgaaaa tcatcaccga | 5580 |
| gataatgtag | tagacttatt | tcctaaatca | gccaacatgc | tgaattccat aaattgtcaa | 5640 |
| gcacaaaatt | gaagtaattt | ttgaaaacta | atcatttcaa | ttttggatat ttcacttaag | 5700 |
| ggatgccttt | agttactttg | gcaagtttat | tctagttgag | cactctctta tagaaagtag | 5760 |
| aaacttgagc | cataggaact | taggtagttt | aacccatcat | attttcttgc ttgaaaattt | 5820 |
| atcattgaga | taatagatca | gacgtagttc | atatatcatc | caacttgctg aattccataa | 5880 |
| atggtcaaca | aaaattaaag | taattcgaaa | gtgattgttt | cagtgtagaa gcaaattgca | 5940 |
| gccaacattg | agtagcagct | tttggatatt | acttctatcg | taactagcaa ttcaatacat | 6000 |
| taaagcatat | gctaaacaca | atgaacttat | cttttcgact | ggttgtttct atgtttaacc | 6060 |
| tgtggagaaa | acaacagatt | tagtatatcc | gtgtgtttct | gttgcaggtt tgaagcttgt | 6120 |
| tggcttgaaa | tacatctctc | cgggaaaggg | atcatttaag | gtgaagtctt acattcctga | 6180 |
| tgactacaaa | gacctagttg | atttggcagc | tcgctattga | | 6220 |

<210> SEQ ID NO 13
<211> LENGTH: 6220
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 13

```
atggtgaacg aagctcttat ctccgatccg gtggatcctc tccacagcct tgccggactt      60
tctctactcc caacaacagt tagggtttcc accggcgcct cagtatcagt agactccaaa     120
gacctagagt caattcacaa tttcatgaag tccatggtaa ttttccgttt gttttcttc     180 acttctttag atttctagct cttttataga tcttacatgt taatttagag agaagtagt     240 gttaatgtcg ttactatgga gttttcgctg ttcttcggtt cgttcctgca ctgaactcca     300
acttacaatt agtacaatta aaatggagtc taacttacat aattgttgta gtttgtccgt     360
ttacaattgg ctagttatat gattttggat gatgttgttc tccttcttta tgataataaa     420
aggaaaccaa gggtcctggg ctcttggagg aggctaggga aattgtggat aacggtgcgg     480
agcttttgaa taccaagttt acaagtttca tacgatctaa aggcattgat ggggatcttg     540
caatcaaggg aaaggagaag gtccaggaga aagaccagg acttgggcgt aaaagggctc     600 gatttttccct caagcctagt acaaggtaaa ttatagacag ttttttcttta ttctctaatt     660 agatcctatt gaaccatgg tgttagctta ccttgctatg cagtcaacct actgtcagca     720
tagctcctcg tttagatatt gatcaactat cagatccagt ggaattttc tcagttgctg     780 aaaagctaga aggtgatttt gtttcttttg ttatctctta actatctgct tgcaaatttg     840
atccgtcggc aactaaaaac agtatatatt atacttagaa aaataacagt tttagtgttt     900
tacatatggt gaacttacag ttgctgagaa ggaaatagaa agacagaaag gtggcagtat     960
ccatgatcca gatgtgaata tcccccagc caatgctcgg cgtcgtcgac caggcatctt    1020
ggggtacacc tagatactct ttgttttttt acatggaaat gcctgtccta cctttatcgt    1080
cctctcaact tgttgttgca cctttttaga gttctctttt ctgtctcagc aaatcggtga    1140
agtataagca ccgtttctca tcctcccagc ctgagaatga tgatgcattt atatcatctc    1200
aagagacatt ggaggatgat attctggtgg aacatggttc tcagttgcca gaagagctcc    1260
atggcctcaa tgttgaacta caagaagcag aactcacagg ttattgggtt taactaatca    1320
agatagatac cttctgattt ctagattata tttttaactt ctctatgagc agaatgtcat    1380
ttcagaagtg ataattgctt tccaattcaa cagggccaat aaagaaatca gaaaacagaa    1440
tcaacaagat actggatgaa ttactgtctg gtagtggtga agatctagac cgggacatgg    1500
cagtatccaa attgcaagag cagttgaaga tcaagcccat tgaactagga actttatgta    1560
ttcctgagtt ccctgtgact ggaaagtttg atggtaaggc tcttggagag agaattcaga    1620
agcctagtaa gttttttttg gagatagcgg agttggttaa aagtgcaact gagggaacgc    1680
catcctctca caaacagcat gaagaaagtc ctgccagtaa attagcatca cccactccac    1740
caaaaagtcc atttggttca ttgtctttgt tgaaaaagaa acttatgcag tcaaatccac    1800
tgagagatcc ttttttcgcct ctcaacattg atctgcaatc agagcatcca gattggtccg    1860
cgaagaagaa atcacaatgt gtaaataata atgttggacc tattgaatct cgtggttgtg    1920
aaaatacaaa tattatggtc cctttaagag gttcagactt agtgcatgag caaccaattg    1980
aaaagaatcc aggcagagat agtgtaaaaa ctgggccaaa tggatctcga tctggaatgg    2040
agcaacataa tggctatgat gatattgatg ccaatactaa cgacaactta aatatgagaa    2100
atgtggattc ccaccatgag tctgatgggc ttgacaaagt gaaagatgat tcagttataa    2160
agaatgtttt gaaggctcta caaggtcttg agaccaaatc ctacattgac tgtcaaaagc    2220
tgcaggatag tgaagttctt gctgaaacac taccttctct tcaagcccaa ggaaaagctg    2280
tcgatacagc caattatacc atagaaacag ctgttgagga ttttgatca actgaaattg    2340 atccgctggc aagtctatcc acttcttact attatatgct gcatttgata cattattcca    2400
```

```
ggagttataa ttcaaactgt gacatttttt cattcatacg tcattagcag gttgacaatg  2460
tgctaccaga aacagcgcct tctgcagaac aagatcatta ctttgaggat tctgtcaaag  2520
acttaaatag tggtgagatt ctattttgga tgattttttt tatgccaagt catcatttat  2580
gaagatgcga catttgagca ttgtctattt cttgctagat tcttttgtat acacaaattt  2640
ttgtacgtat tcaaaacaat ctttttttatg ttttaacaca tcgcttgagt tttacccgga  2700
atcatctgca gtcaactatt cgttttttga ccacttatat tcaactctta actgggtgat  2760
tcatggtact ggaactggac aattcttagg tctgctacag gctatagatt aaggtgtgaa  2820
gtgctggaat ttagtatacg aagaagtaac tgcccatgtt tgccagaaat tgtactgcaa  2880
tagaccaata ccttggttgc ttggaatgtt ctgtcataac ttctctttcc ttttccttt   2940 catctctggt tttttaatgg gaggatgcat gtgatgcatc tttataaaaa atagatgtgt  3000
agaattttga acttgtagtt gtcaagaatc atgactttg atcttcattt tttttaaaaa   3060
aggtaatgac tcaattgaga agatggggat aacgctctat cattgtatac catattgaaa  3120
accttacaaa agatatggtt ctcagcaaaa acacatgcat cactatttat catgatgttt  3180
taagtactcc aaaagtaaca agatttgtct aatatgtttg aacttcactt ctatctttcg  3240
agcatcctgt taggtactag atataaatta acgagacgta agtttgtact ggtacatgca  3300
agttattgct gcattctgat gttctattgt ggttatagga gcattaaggt gtctatagtg  3360
tcacgagcaa agcattaggg atgattaatc attaaagtaa cccatgtact gatagcaaaa  3420
gatcatatgc cacatattga tacctattgc gtagtcacaa actcaaccct gctcttcaga  3480
gtcagaaggc gcttccactt aacccagttt ataattggtt acttgcttta ctttctttta  3540
tttataaagt aatatgctac ctccaaatat gaacttcagc tgctgaaatc attctcacat  3600
tgatcacctt ctcttttgca atggttcttt gagcttgtgt cactctttac attataaagt  3660
tgtcatagta cctgtgcatt ctgaatatat gttgttttc ttgaacatat agctagttat   3720
tttacccact ctactttgca tatcttaact agtaataaca gtctaaagtt tggaaagaac  3780
ttgagaacct tggtatcttt atacagatca attgaactca gtgggagttg aagttccttc  3840
tagagacgtg agacctaaat ttccggagat gagccctcag catcacaagc aggttgcctc  3900
ctttcttgaa tggtccttca ttattttttta tttatatagg aaactcaaag tgccaagtta  3960
atcctttggt attcacacac acacatacac actctctctc tctctctccc aaaagcaaat  4020
aatgatggca gggtttaagg ggtcaaaata cttgcgacat acaaaagcct ggtatttgag  4080
tggagaagtg agcacaatgt ccaaaattta tgctccatac agtttcaaac catttgccat  4140
tggtcctcag agttttcgg atcgaaaaca attattgtta aagagtctac aatatcaaag   4200
tcagtaaaaa tcgtctgatt ctccaattgt aactgtaaat tagaagacag taaagctgat  4260
tgcttgtatg taaacaaatc tgtagatgcc taaacactag gatagggttt gtgcaaaaac  4320
atatcgcaat tcccaaattt aaaaaaaaac tagcatgaac tgcgtttgat aaccatgatt  4380 attttttttgt tcttttgaaa aaagtgcaat gatgtgactg atttaagttg ccaaatgtgt  4440
tgatttctgt ctagggttag gacattttaa agctgtctac tgaaatgacc ctctgatatt  4500
attggtgtta aaatttgaca accagtcgtg ataagagtcg atatttctga cgtgacagtg  4560
gatattgaat gatattgatt gaacacatta atagttttag cccatcatgt ctcctaattt  4620
tgggtttaca tgtgaatgct tgtgctcttt gcagttgtat ttctttacct gtattggtta  4680
tactgattga catgcaatat ttctgatgca ttaggcaaaa gataagcaac agaaagcaaa  4740
```

```
ggaacttgct gttggaaggc gtgaaagaaa acatctttct tctaggccaa gtctagcagg    4800 ttttttactct tgcgactatg gggatgtctt catttgaagt ctttcatttg tgttttttgat    4860 aaagaatttc atgaatttga cagatgctgg cacatcattt gaaagtgggg ttagacgaag    4920
caaacgaatg aagacaaggc ctttggaata ttggaaaggc gaaagattat tatatggacg    4980
ggttgatgag ggtgagtatt gtcttgtaaa ttcttgtgtt gttactttgc tgggtttctg    5040
ttggattcat tgttagact tgggtgatag ggtaataatt catcttgatc ctcaaatcta    5100
gttttctttt tttggcgcg tgcgtgtgag agagagatgt gtgaaactag gccacaacat    5160
gctagacttt atacttatag tcttgggaag gtaactactc aaggatattt tcttgtcctt    5220
tagataggat gtttatcaca ctaaacgacc taatattgga gaggttggtg gtaacatatg    5280
cacattttgc atagaactct acaagacagc gaaagaaaat attagggacg cttagctat    5340 tagagaagca tggtaactag gttacttgca tgtctgctaa gagagtgcaa gttagggtat    5400
cagaatctag ttttcaggga ttagtttcgt acttggtcaa gtctcttcca gcaggagatt    5460
aacttagtta aggctctcct agttggtgac ttactagctc agaatactca ttggaacttg    5520
aattacagga aattaggtaa tttgatcctc aatattttg tgcttgaaaa tcatcaccga    5580
gataatgtag tagacttatt tcctaaatca gccaacatgc tgaattccat aaattgtcaa    5640
gcacaaaatt gaagtaattt tgaaaactaa atcatttcaa ttttggatat ttcacttaag    5700
ggatgccttt agttactttg gcaagtttat tctagttgag cactctctta tagaaagtag    5760
aaacttgagc cataggaact taggtagttt aacccatcat atttcttgc ttgaaaattt    5820 atcattgaga taatagatca gacgtagttc atatatcatc caacttgctg aattccataa    5880
atggtcaaca aaaattaaag taattcgaaa gtgattgttt cagtgtagaa gcaaattgca    5940
gccaacattg agtagcagct tttggatatt acttctatcg taactagcaa ttcaatacat    6000
taaagcatat gctaaacaca atgaacttat cttttcgact ggttgtttct atgtttaacc    6060
tgtggagaaa acaacagatt tagtatatcc gtgtgttttct gttgcaggtt tgaagcttgt    6120
tggcttgaaa tacatctctc cgggaagggg atcatttaag gtgaagtctt acattcctga    6180
tgactacaaa gacctagttg atttggcagc tcgctattga                          6220
```

<210> SEQ ID NO 14
<211> LENGTH: 2130
<212> TYPE: DNA
<213> ORGANISM: Solanum lycopersicum

<400> SEQUENCE: 14

```
atggtgaacg aagctcttat ctccgatccg gtggatcctc tccacagcct tgccggactt      60
tctctactcc caacaacagt tagggtttcc accggcgcct cagtatcagt agactccaaa     120
gacctagagt caattcacaa tttcatgaag tccatggaaa ccaagggtcc tgggctcttg     180
gaggaggcta gggaaattgt ggataacggt gcggagcttt tgaataccaa gtttacaagt     240
ttcatacgat ctaaaggcat tgatggggat cttgcaatca agggaaagga gaaggtccag     300
gagagaagac caggacttgg gcgtaaaagg gctcgatttt ccctcaagcc tagtacaagt     360
caacctactg tcagcatagc tcctcgttta gatattgatc aactatcaga tccagtggaa     420
tttttctcag ttgctgaaaa gctagaagtt gctgagaagg aaatagaaag acagaaaggt     480
ggcagtatcc atgatccaga tgtgaataat ccccccagcca atgctcggcg tcgtcgacca     540
ggcatcttgg gcaaatcggt gaagtataag caccgtttct catcctccca gcctgagaat     600
gatgatgcat ttatatcatc tcaagagaca ttggaggatg atattctggt ggaacatggt     660
```

```
tctcagttgc cagaagagct ccatggcctc aatgttgaac tacaagaagc agaactcaca    720
gggccaataa agaaatcaga aaacagaatc aacaagatac tggatgaatt actgtctggt    780
agtggtgaag atctagaccg ggacatggca gtatccaaat gcaagagca gttgaagatc     840 aagcccattg aactaggaac tttatgtatt cctgagttcc ctgtgactgg aaagtttgat    900
ggtaaggctc ttggagagag aattcagaag cctagtaagt tttttttgga gatagcggag    960
ttggttaaaa gtgcaactga gggaacgcca tcctctcaca acagcatga agaaagtcct    1020 gccagtaaat tagcatcacc cactccacca aaaagtccat tggttcatt gtctttgttg    1080 aaaaagaaac ttatgcagtc aaatccactg agagatcctt tttcgcctct caacattgat    1140
ctgcaatcag agcatccaga ttggtccgcg aagaagaaat cacaatgtgt aaataataat    1200
gttggaccta ttgaatctcg tggttgtgaa aatacaaata ttatggtccc tttaagaggt    1260
tcagacttag tgcatgagca accaattgaa aagaatccag gcagagatag tgtaaaaact    1320
gggccaaatg gatctcgatc tggaatggag caacataatg ctatgatga tattgatgcc    1380 aatactaacg acaacttaaa tatgagaaat gtggattccc accatgagtc tgatgggctt    1440
gacaaagtga aagatgattc agttataaag aatgttttga aggctctaca aggtcttgag    1500
accaaatcct acattgactg tcaaaagctg caggatagtg aagttcttgc tgaaacacta    1560
ccttctcttc aagcccaagg aaaagctgtc gatacagcca attataccat agaaacagct    1620
gttgaggatt ttggatcaac tgaaattgat ccgctggttg acaatatgct accagaaaca    1680
gcgccttctg cagaacaaga tcattacttt gaggattctg tcaaagactt aaatagtgat    1740
caattgaact cagtgggagt tgaagttcct tctagagacg tgagacctaa atttccggag    1800
atgagccctc agcatcacaa gcaggcaaaa gataagcaac agaaagcaaa ggaacttgct    1860
gttggaaggc gtgaaagaaa acatctttct tctaggccaa gtctagcaga tgctggcaca    1920
tcatttgaaa gtggggttag acgaagcaaa cgaatgaaga caaggccttt ggaatattgg    1980
aaaggcgaaa gattattata tggacgggtt gatgagggtt tgaagcttgt tggcttgaaa    2040
tacatctctc cgggaaaggg atcatttaag gtgaagtctt acattcctga tgactacaaa    2100
gacctagttg atttggcagc tcgctattga                                    2130
```

<210> SEQ ID NO 15
<211> LENGTH: 670
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (200)..(200)
<223> OTHER INFORMATION: Any naturally occurring amino acid
<220> FEATURE:
<221> NAME/KEY: MOD_RES
<222> LOCATION: (342)..(342)
<223> OTHER INFORMATION: Any naturally occurring amino acid
<220> FEATURE:
<221> NAME/KEY: MOD_RES
<222> LOCATION: (383)..(383)
<223> OTHER INFORMATION: Any naturally occurring amino acid
<220> FEATURE:
<221> NAME/KEY: MOD_RES
<222> LOCATION: (556)..(556)
<223> OTHER INFORMATION: Any naturally occurring amino acid

<400> SEQUENCE: 15

Met Val Asn Glu Glu Ala Arg His Ser Asp Val Ile Asp Pro Leu Ala

```
1               5                   10                  15
Ala Tyr Ser Gly Ile Asn Leu Phe Pro Thr Ala Phe Gly Thr Leu Pro
                20                  25                  30

Asp Pro Ser Lys Pro His Asp Leu Gly Thr Asp Leu Asp Gly Ile His
                35                  40                  45

Lys Arg Leu Lys Ser Met Val Leu Arg Ser Pro Lys Leu Leu Glu
                50                  55                  60

Gln Ala Arg Ser Ile Leu Asp Gly Asn Ser Asn Ser Met Ile Ser Glu
65                  70                  75                  80

Ala Ala Thr Phe Leu Val Lys Asn Glu Lys Asn Glu Glu Ala Thr Val
                85                  90                  95

Lys Ala Glu Glu Asn Pro Gln Glu Arg Arg Pro Ala Leu Asn Arg Lys
                100                 105                 110

Arg Ala Arg Phe Ser Leu Lys Pro Asp Ala Arg Gln Pro Pro Val Asn
                115                 120                 125

Leu Glu Pro Thr Phe Asp Ile Lys Gln Leu Lys Asp Pro Glu Glu Phe
                130                 135                 140

Phe Leu Ala Tyr Glu Lys His Glu Asn Ala Lys Lys Glu Ile Gln Lys
145                 150                 155                 160

Gln Thr Gly Ala Val Leu Lys Asp Leu Asn Gln Asn Pro Ser Thr
                165                 170                 175

Asn Thr Arg Gln Arg Arg Pro Gly Ile Leu Gly Arg Ser Val Arg Tyr
                180                 185                 190

Lys His Gln Tyr Ser Ser Ile Xaa Thr Glu Asp Asp Gln Asn Val Asp
                195                 200                 205

Pro Ser Gln Val Thr Phe Asp Ser Gly Ile Phe Ser Pro Leu Lys Leu
                210                 215                 220

Gly Thr Glu Thr His Pro Ser Pro His Ile Ile Asp Ser Glu Lys Lys
225                 230                 235                 240

Thr Asp Glu Asp Val Ala Phe Glu Glu Glu Glu Glu Glu Leu
                245                 250                 255

Val Ala Ser Ala Thr Lys Ala Glu Asn Arg Val Asn Asp Ile Leu Asp
                260                 265                 270

Glu Phe Leu Ser Gly Asn Cys Glu Asp Leu Glu Gly Asp Arg Ala Ile
                275                 280                 285

Asn Ile Leu Gln Glu Arg Leu Gln Ile Lys Pro Leu Thr Leu Glu Lys
                290                 295                 300

Leu Cys Leu Pro Asp Leu Glu Ala Ile Pro Thr Met Asn Leu Lys Ser
305                 310                 315                 320

Ser Arg Gly Asn Leu Ser Lys Arg Ser Leu Ile Ser Val Asp Asn Gln
                325                 330                 335

Leu Gln Lys Ile Glu Xaa Leu Lys Ser Lys Gln Asp Asn Glu Asn Leu
                340                 345                 350

Val Asn Pro Val Ser Thr Pro Ser Ser Met Arg Ser Pro Leu Ala Ser
                355                 360                 365

Leu Ser Ala Leu Asn Arg Arg Ile Ser Leu Ser Asn Ser Ser Xaa Asp
                370                 375                 380

Ser Phe Ser Ala His Gly Ile Asp Gln Ser Pro Ala Arg Asp Pro Tyr
385                 390                 395                 400

Leu Phe Glu Leu Gly Asn His Leu Ser Asp Ala Val Gly Ile Thr Glu
                405                 410                 415

Gln Ser Ser Val Ser Lys Leu Lys Pro Leu Leu Thr Arg Asp Gly Gly
                420                 425                 430
```

```
Thr Val Ala Asn Gly Ile Lys Pro Ser Lys Ile Leu Ser Gly Asp Asp
            435                 440                 445

Ser Met Ser Lys Ile Ser Ser Asn Ile Leu Asn Val Pro Gln Val
    450                 455                 460

Gly Gly Asn Thr Ala Leu Ser Gly Thr Tyr Ala Ser Thr Glu Ala Lys
465                 470                 475                 480

Asn Val Ser Gly Ser Ser Thr Asp Val Glu Ile Asn Glu Lys Leu Ser
                485                 490                 495

Cys Leu Glu Ala Gln Ala Asp Ala Val Ala Asn Met Gln Ile Glu Asp
                500                 505                 510

His Glu Gly Ser Ala Ser Glu Gln Pro Lys Leu Ser Glu Val Asp Leu
            515                 520                 525

Ile Lys Glu Tyr Pro Val Gly Ile Arg Ser Gln Leu Asp Gln Ser Thr
        530                 535                 540

Thr Thr Thr Cys Ala Glu Asn Ile Val Asp Gly Xaa Ser Arg Ser Ser
545                 550                 555                 560

Gly Thr Asp His His Asp Gly Glu Gln Val Lys Pro Lys Ser Arg Ala
                565                 570                 575

Asn Lys Gln Arg Lys Gly Lys Lys Ile Ser Gly Arg Gln Ser Leu Ala
                580                 585                 590

Gly Ala Gly Thr Thr Trp Gln Ser Gly Val Arg Arg Ser Thr Arg Phe
            595                 600                 605

Lys Thr Arg Pro Leu Glu Tyr Trp Lys Gly Glu Arg Leu Leu Tyr Gly
        610                 615                 620

Arg Val His Glu Ser Leu Ala Thr Val Ile Gly Leu Lys Tyr Val Ser
625                 630                 635                 640

Pro Ala Lys Gly Asn Gly Lys Pro Thr Met Lys Val Lys Ser Leu Val
                645                 650                 655

Ser Asn Glu Tyr Lys Asp Leu Val Glu Leu Ala Ala Leu His
                660                 665                 670

<210> SEQ ID NO 16
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any naturally occurring amino acid
<220> FEATURE:
<221> NAME/KEY: MOD_RES
<222> LOCATION: (40)..(40)
<223> OTHER INFORMATION: Any naturally occurring amino acid
<220> FEATURE:
<221> NAME/KEY: MOD_RES
<222> LOCATION: (103)..(103)
<223> OTHER INFORMATION: Any naturally occurring amino acid
<220> FEATURE:
<221> NAME/KEY: MOD_RES
<222> LOCATION: (206)..(206)
<223> OTHER INFORMATION: Any naturally occurring amino acid
<220> FEATURE:
<221> NAME/KEY: MOD_RES
<222> LOCATION: (215)..(215)
<223> OTHER INFORMATION: Any naturally occurring amino acid
<220> FEATURE:
<221> NAME/KEY: MOD_RES
<222> LOCATION: (242)..(242)
<223> OTHER INFORMATION: Any naturally occurring amino acid
<220> FEATURE:
```

-continued

```
<221> NAME/KEY: MOD_RES
<222> LOCATION: (256)..(256)
<223> OTHER INFORMATION: Any naturally occurring amino acid
<220> FEATURE:
<221> NAME/KEY: MOD_RES
<222> LOCATION: (271)..(271)
<223> OTHER INFORMATION: Any naturally occurring amino acid
<220> FEATURE:
<221> NAME/KEY: MOD_RES
<222> LOCATION: (277)..(277)
<223> OTHER INFORMATION: Any naturally occurring amino acid
<220> FEATURE:
<221> NAME/KEY: MOD_RES
<222> LOCATION: (296)..(296)
<223> OTHER INFORMATION: Any naturally occurring amino acid
<220> FEATURE:
<221> NAME/KEY: MOD_RES
<222> LOCATION: (363)..(363)
<223> OTHER INFORMATION: Any naturally occurring amino acid
<220> FEATURE:
<221> NAME/KEY: MOD_RES
<222> LOCATION: (365)..(365)
<223> OTHER INFORMATION: Any naturally occurring amino acid
<220> FEATURE:
<221> NAME/KEY: MOD_RES
<222> LOCATION: (477)..(477)
<223> OTHER INFORMATION: Any naturally occurring amino acid
<220> FEATURE:
<221> NAME/KEY: MOD_RES
<222> LOCATION: (484)..(484)
<223> OTHER INFORMATION: Any naturally occurring amino acid
<220> FEATURE:
<221> NAME/KEY: MOD_RES
<222> LOCATION: (537)..(537)
<223> OTHER INFORMATION: Any naturally occurring amino acid
<220> FEATURE:
<221> NAME/KEY: MOD_RES
<222> LOCATION: (583)..(583)
<223> OTHER INFORMATION: Any naturally occurring amino acid
<220> FEATURE:
<221> NAME/KEY: MOD_RES
<222> LOCATION: (606)..(606)
<223> OTHER INFORMATION: Any naturally occurring amino acid
<220> FEATURE:
<221> NAME/KEY: MOD_RES
<222> LOCATION: (624)..(624)
<223> OTHER INFORMATION: Any naturally occurring amino acid
<220> FEATURE:
<221> NAME/KEY: MOD_RES
<222> LOCATION: (688)..(688)
<223> OTHER INFORMATION: Any naturally occurring amino acid

<400> SEQUENCE: 16

Met Ala Asp Xaa Ser Arg Ser Ser Ser Leu Glu Asp Pro Leu His
1               5                  10                  15

Ala Tyr Ser Gly Leu Ser Leu Phe Pro Arg Thr Leu Lys Ser Leu Ser
            20                  25                  30

Asn Pro Leu Pro Pro Pro Leu Xaa Gln Ser Glu Asp Leu Gln Gln Thr
        35                  40                  45

His Thr Leu Leu Glu Ser Met Pro Phe Glu Ile Gln Lys Glu His Gln
    50                  55                  60

Glu Gln Ala Lys Ala Ile Leu Glu Asp Val Asn Val Asp Val Lys Leu
65                  70                  75                  80

Asn Pro Ile Pro Asn Lys Arg Glu Arg Arg Pro Gly Leu Asp Arg Lys
                85                  90                  95

Arg Lys Ser Phe Ser Leu Xaa Leu Thr Thr Ser Gln Pro Pro Pro Val
            100                 105                 110

Ala Pro Ser Phe Asp Pro Ser Lys Tyr Pro Lys Pro Glu Asp Tyr Phe
        115                 120                 125

Ala Ala Tyr Asp Lys Phe Glu Leu Ala Asn Arg Glu Trp Gln Lys Gln
```

-continued

```
                130               135               140
Thr Gly Ser Ser Val Ile Asp Thr Gln Gln Asn Pro Pro Ser Arg Arg
145                 150               155               160

Pro Arg Arg Pro Gly Ile Pro Gly Arg Lys Arg Gly Pro Tyr Lys His
                165               170               175

Thr Tyr Thr Asp Ser Tyr Phe Thr Asp Ala Ile Asn Leu Glu Ala Ser
                180               185               190

Glu Lys Glu Asn Pro Ile Pro Ser Glu Gln Ser Leu Glu Xaa Thr Thr
                195               200               205

Ala Ala His Val Thr Thr Xaa Asp Arg Glu Val Asp Asp Ser Thr Val
210                 215               220

Asp Thr Asp Lys Asp Leu Asn Asn Ile Leu Thr Glu Leu Leu Ala Cys
225                 230               235               240

Ser Xaa Asp Glu Leu Glu Gly Asp Ala Ala Val Lys Leu Leu Glu Xaa
                245               250               255

Arg Leu Gln Ile Lys Pro Phe Asn Glu Lys Phe Asp Ile Pro Xaa Phe
                260               265               270

Gln Asp Val Arg Xaa Met Asp Leu Lys Ala Ser Gly Ser Asn Pro Ser
                275               280               285

Asn Arg Lys Ser Ala Leu Ser Xaa Ile Gln Asn Leu Leu Lys Gly Ile
290                 295               300

Asn Arg Asp Ala Val Arg Lys Asn Ser His Ser Pro Ser Pro Lys His
305                 310               315               320

Phe Ser Ser Pro Asn Pro Pro Glu Asp Gln Phe Ser Phe Pro Asp Ile
                325               330               335

His Asn Leu Leu Pro Gly Asp Gln Gln Pro Ser Glu Val Asp Ile Gln
                340               345               350

Pro Ala Lys Asp Leu Asn Ile Gly Ser Ser Xaa Ala Xaa Asp Ala Asp
                355               360               365

Lys Asp Ile Pro Asn Thr Ser Pro Ser Asn Val Gly Thr Val Asp Val
370                 375               380

Ala Ser Pro Phe Asn Ser Ser Val Gln Lys Ser Ser Gly Glu Asp Asp
385                 390               395               400

Ser Thr His Ser Gly Ile His Arg Ser His Ser Ser Arg Asp Gly Asn
                405               410               415

Ala Asp Asn Cys Val Asp Asp Ser Ile Thr Asn Ile Asn Ser Ala Thr
                420               425               430

Leu Glu Val Asn Val Asp Met Gln Thr Lys Gly Lys Glu Gly Asp Val
                435               440               445

Pro Met Ser Glu Ser Gly Ala Asn Arg Asn Thr Gly Arg Arg Glu Asn
450                 455               460

Asp Ala Asp Ile Asn Glu Thr Asp Tyr Leu Glu Xaa Leu Ala Glu
465                 470               475               480

Tyr Ala Ser Xaa Glu Val Thr Arg Pro Phe Thr Val Glu Glu Asp Ser
                485               490               495

Ile Pro Tyr Gln Gln Gly Glu Ser Ser Lys Ser Pro Asn Arg Ala Pro
                500               505               510

Glu Gln Tyr Asn Thr Met Asp Gly Ser Phe Glu His Ala Glu His Ile
                515               520               525

Gln Gly Gln His Glu Glu Glu Asn Xaa Asn Thr Asp Thr Ala Cys Gly
                530               535               540

Leu Gln Val Glu Asn Ala Gln Glu Val His Asn Ser Ser His Lys Gln
545                 550               555               560
```

```
Thr Asn Lys Arg Arg Lys Arg Gly Ser Ser Asp Ser Asn Met Lys Lys
            565                 570                 575

Arg Ser Lys Thr Val His Xaa Glu Thr Gly Gly Asp Lys Gln Met Lys
        580                 585                 590

Thr Leu Pro His Glu Ser Gly Ala Lys Lys Gln Thr Lys Xaa Lys Ser
    595                 600                 605

Asn Glu Arg Glu Glu Lys Lys Gln Lys Lys Thr Val Thr Arg Glu Xaa
610                 615                 620

Lys Leu Phe Ser Arg Arg Lys Ser Leu Ala Ala Ala Gly Thr Lys Met
625                 630                 635                 640

Glu Gly Gly Val Arg Arg Ser Thr Arg Ile Lys Ser Arg Pro Leu Glu
                645                 650                 655

Tyr Trp Arg Gly Glu Arg Phe Leu Tyr Gly Arg Ile His Glu Ser Leu
                660                 665                 670

Thr Thr Val Ile Gly Ile Lys Tyr Ala Ser Pro Gly Lys Gly Lys Xaa
            675                 680                 685

Asp Lys Arg Ala Ser Lys Val Lys Ser Phe Val Ser Asp Asp Tyr Lys
    690                 695                 700

Glu Leu Val Asp Phe Ala Ala Leu His
705                 710

<210> SEQ ID NO 17
<211> LENGTH: 657
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any naturally occurring amino acid
<220> FEATURE:
<221> NAME/KEY: MOD_RES
<222> LOCATION: (36)..(36)
<223> OTHER INFORMATION: Any naturally occurring amino acid
<220> FEATURE:
<221> NAME/KEY: MOD_RES
<222> LOCATION: (45)..(45)
<223> OTHER INFORMATION: Any naturally occurring amino acid
<220> FEATURE:
<221> NAME/KEY: MOD_RES
<222> LOCATION: (55)..(55)
<223> OTHER INFORMATION: Any naturally occurring amino acid
<220> FEATURE:
<221> NAME/KEY: MOD_RES
<222> LOCATION: (61)..(61)
<223> OTHER INFORMATION: Any naturally occurring amino acid
<220> FEATURE:
<221> NAME/KEY: MOD_RES
<222> LOCATION: (79)..(79)
<223> OTHER INFORMATION: Any naturally occurring amino acid
<220> FEATURE:
<221> NAME/KEY: MOD_RES
<222> LOCATION: (89)..(89)
<223> OTHER INFORMATION: Any naturally occurring amino acid
<220> FEATURE:
<221> NAME/KEY: MOD_RES
<222> LOCATION: (116)..(116)
<223> OTHER INFORMATION: Any naturally occurring amino acid
<220> FEATURE:
<221> NAME/KEY: MOD_RES
<222> LOCATION: (119)..(119)
<223> OTHER INFORMATION: Any naturally occurring amino acid
<220> FEATURE:
<221> NAME/KEY: MOD_RES
<222> LOCATION: (125)..(125)
<223> OTHER INFORMATION: Any naturally occurring amino acid
```

-continued

```
<220> FEATURE:
<221> NAME/KEY: MOD_RES
<222> LOCATION: (129)..(129)
<223> OTHER INFORMATION: Any naturally occurring amino acid
<220> FEATURE:
<221> NAME/KEY: MOD_RES
<222> LOCATION: (134)..(134)
<223> OTHER INFORMATION: Any naturally occurring amino acid
<220> FEATURE:
<221> NAME/KEY: MOD_RES
<222> LOCATION: (138)..(138)
<223> OTHER INFORMATION: Any naturally occurring amino acid
<220> FEATURE:
<221> NAME/KEY: MOD_RES
<222> LOCATION: (142)..(142)
<223> OTHER INFORMATION: Any naturally occurring amino acid
<220> FEATURE:
<221> NAME/KEY: MOD_RES
<222> LOCATION: (152)..(152)
<223> OTHER INFORMATION: Any naturally occurring amino acid
<220> FEATURE:
<221> NAME/KEY: MOD_RES
<222> LOCATION: (153)..(153)
<223> OTHER INFORMATION: Any naturally occurring amino acid
<220> FEATURE:
<221> NAME/KEY: MOD_RES
<222> LOCATION: (155)..(155)
<223> OTHER INFORMATION: Any naturally occurring amino acid
<220> FEATURE:
<221> NAME/KEY: MOD_RES
<222> LOCATION: (161)..(161)
<223> OTHER INFORMATION: Any naturally occurring amino acid
<220> FEATURE:
<221> NAME/KEY: MOD_RES
<222> LOCATION: (162)..(162)
<223> OTHER INFORMATION: Any naturally occurring amino acid
<220> FEATURE:
<221> NAME/KEY: MOD_RES
<222> LOCATION: (167)..(167)
<223> OTHER INFORMATION: Any naturally occurring amino acid
<220> FEATURE:
<221> NAME/KEY: MOD_RES
<222> LOCATION: (168)..(168)
<223> OTHER INFORMATION: Any naturally occurring amino acid
<220> FEATURE:
<221> NAME/KEY: MOD_RES
<222> LOCATION: (171)..(171)
<223> OTHER INFORMATION: Any naturally occurring amino acid
<220> FEATURE:
<221> NAME/KEY: MOD_RES
<222> LOCATION: (174)..(174)
<223> OTHER INFORMATION: Any naturally occurring amino acid
<220> FEATURE:
<221> NAME/KEY: MOD_RES
<222> LOCATION: (179)..(179)
<223> OTHER INFORMATION: Any naturally occurring amino acid
<220> FEATURE:
<221> NAME/KEY: MOD_RES
<222> LOCATION: (185)..(185)
<223> OTHER INFORMATION: Any naturally occurring amino acid
<220> FEATURE:
<221> NAME/KEY: MOD_RES
<222> LOCATION: (198)..(198)
<223> OTHER INFORMATION: Any naturally occurring amino acid
<220> FEATURE:
<221> NAME/KEY: MOD_RES
<222> LOCATION: (211)..(211)
<223> OTHER INFORMATION: Any naturally occurring amino acid
<220> FEATURE:
<221> NAME/KEY: MOD_RES
<222> LOCATION: (237)..(237)
<223> OTHER INFORMATION: Any naturally occurring amino acid
<220> FEATURE:
<221> NAME/KEY: MOD_RES
<222> LOCATION: (238)..(238)
<223> OTHER INFORMATION: Any naturally occurring amino acid
<220> FEATURE:
<221> NAME/KEY: MOD_RES
<222> LOCATION: (266)..(266)
```

-continued

```
<223> OTHER INFORMATION: Any naturally occurring amino acid
<220> FEATURE:
<221> NAME/KEY: MOD_RES
<222> LOCATION: (274)..(274)
<223> OTHER INFORMATION: Any naturally occurring amino acid
<220> FEATURE:
<221> NAME/KEY: MOD_RES
<222> LOCATION: (314)..(314)
<223> OTHER INFORMATION: Any naturally occurring amino acid
<220> FEATURE:
<221> NAME/KEY: MOD_RES
<222> LOCATION: (320)..(320)
<223> OTHER INFORMATION: Any naturally occurring amino acid
<220> FEATURE:
<221> NAME/KEY: MOD_RES
<222> LOCATION: (322)..(322)
<223> OTHER INFORMATION: Any naturally occurring amino acid
<220> FEATURE:
<221> NAME/KEY: MOD_RES
<222> LOCATION: (335)..(335)
<223> OTHER INFORMATION: Any naturally occurring amino acid
<220> FEATURE:
<221> NAME/KEY: MOD_RES
<222> LOCATION: (341)..(341)
<223> OTHER INFORMATION: Any naturally occurring amino acid
<220> FEATURE:
<221> NAME/KEY: MOD_RES
<222> LOCATION: (342)..(342)
<223> OTHER INFORMATION: Any naturally occurring amino acid
<220> FEATURE:
<221> NAME/KEY: MOD_RES
<222> LOCATION: (350)..(350)
<223> OTHER INFORMATION: Any naturally occurring amino acid
<220> FEATURE:
<221> NAME/KEY: MOD_RES
<222> LOCATION: (358)..(358)
<223> OTHER INFORMATION: Any naturally occurring amino acid
<220> FEATURE:
<221> NAME/KEY: MOD_RES
<222> LOCATION: (410)..(410)
<223> OTHER INFORMATION: Any naturally occurring amino acid
<220> FEATURE:
<221> NAME/KEY: MOD_RES
<222> LOCATION: (411)..(411)
<223> OTHER INFORMATION: Any naturally occurring amino acid
<220> FEATURE:
<221> NAME/KEY: MOD_RES
<222> LOCATION: (416)..(416)
<223> OTHER INFORMATION: Any naturally occurring amino acid
<220> FEATURE:
<221> NAME/KEY: MOD_RES
<222> LOCATION: (426)..(426)
<223> OTHER INFORMATION: Any naturally occurring amino acid
<220> FEATURE:
<221> NAME/KEY: MOD_RES
<222> LOCATION: (458)..(458)
<223> OTHER INFORMATION: Any naturally occurring amino acid
<220> FEATURE:
<221> NAME/KEY: MOD_RES
<222> LOCATION: (479)..(479)
<223> OTHER INFORMATION: Any naturally occurring amino acid
<220> FEATURE:
<221> NAME/KEY: MOD_RES
<222> LOCATION: (488)..(488)
<223> OTHER INFORMATION: Any naturally occurring amino acid
<220> FEATURE:
<221> NAME/KEY: MOD_RES
<222> LOCATION: (523)..(523)
<223> OTHER INFORMATION: Any naturally occurring amino acid
<220> FEATURE:
<221> NAME/KEY: MOD_RES
<222> LOCATION: (534)..(534)
<223> OTHER INFORMATION: Any naturally occurring amino acid
<220> FEATURE:
<221> NAME/KEY: MOD_RES
<222> LOCATION: (571)..(571)
<223> OTHER INFORMATION: Any naturally occurring amino acid
<220> FEATURE:
<221> NAME/KEY: MOD_RES
```

```
<222> LOCATION: (587)..(587)
<223> OTHER INFORMATION: Any naturally occurring amino acid
<220> FEATURE:
<221> NAME/KEY: MOD_RES
<222> LOCATION: (609)..(609)
<223> OTHER INFORMATION: Any naturally occurring amino acid

<400> SEQUENCE: 17
```

| Met | Ala | Ser | Leu | Pro | Ser | Ser | Glu | Pro | Tyr | Asn | Asp | Thr | Ile | His |
|---|---|---|---|---|---|---|---|---|---|---|---|---|---|---|
| 1 | | | | 5 | | | | | 10 | | | | | 15 |

| His | Leu | Arg | Ser | Met | Ala | Leu | Arg | Val | Phe | Xaa | Thr | Glu | Asn | Leu | Thr |
|---|---|---|---|---|---|---|---|---|---|---|---|---|---|---|---|
| | | | 20 | | | | | 25 | | | | | 30 | | |

| Gln | Asp | Val | Xaa | Asn | Asp | Ala | Ser | Glu | Gly | Glu | Phe | Xaa | Arg | Lys | Arg |
|---|---|---|---|---|---|---|---|---|---|---|---|---|---|---|---|
| | | 35 | | | | | 40 | | | | | 45 | | | |

| Arg | Pro | Gly | Leu | Gly | Leu | Xaa | Arg | Pro | Arg | Phe | Ser | Xaa | Lys | Pro | Thr |
|---|---|---|---|---|---|---|---|---|---|---|---|---|---|---|---|
| | 50 | | | | | 55 | | | | | 60 | | | | |

| Lys | Lys | Pro | Ser | Val | Glu | Asp | Leu | Leu | Pro | Ile | Leu | Asp | Leu | Xaa | Ala |
|---|---|---|---|---|---|---|---|---|---|---|---|---|---|---|---|
| 65 | | | | | 70 | | | | | 75 | | | | | 80 |

| Leu | Lys | Asp | Pro | Ala | Glu | Phe | Phe | Xaa | Ala | His | Glu | Arg | Leu | Glu | Asn |
|---|---|---|---|---|---|---|---|---|---|---|---|---|---|---|---|
| | | | | 85 | | | | | 90 | | | | | 95 | |

| Ala | Lys | Arg | Glu | Ile | Gln | Lys | Gln | Leu | Gly | Ala | Ser | Glu | Ser | Asp | Gln |
|---|---|---|---|---|---|---|---|---|---|---|---|---|---|---|---|
| | | | 100 | | | | | 105 | | | | | 110 | | |

| Asp | Ser | Thr | Xaa | Pro | Arg | Xaa | Arg | Pro | Gly | Leu | Xaa | Gly | Asn | Arg |
|---|---|---|---|---|---|---|---|---|---|---|---|---|---|---|
| | | 115 | | | | | 120 | | | | | 125 | | |

| Xaa | Pro | Ile | Arg | Tyr | Xaa | His | Arg | Tyr | Xaa | Thr | Glu | Thr | Xaa | Asp | Asp |
|---|---|---|---|---|---|---|---|---|---|---|---|---|---|---|---|
| | 130 | | | | | 135 | | | | | 140 | | | | |

| Val | Leu | Ser | Ser | Gln | Glu | Ala | Xaa | Xaa | Ser | Xaa | Ser | Leu | Asp | Pro | Val |
|---|---|---|---|---|---|---|---|---|---|---|---|---|---|---|---|
| 145 | | | | | 150 | | | | | 155 | | | | | 160 |

| Xaa | Xaa | Asn | Thr | Asp | Lys | Xaa | Xaa | Ala | Ser | Xaa | Ala | Ser | Xaa | Glu | Lys |
|---|---|---|---|---|---|---|---|---|---|---|---|---|---|---|---|
| | | | | 165 | | | | | 170 | | | | | 175 | |

| Glu | Val | Xaa | Asp | Ser | Ser | Ala | Ile | Xaa | Gly | Asn | Glu | Leu | Asp | Glu | Leu |
|---|---|---|---|---|---|---|---|---|---|---|---|---|---|---|---|
| | | | 180 | | | | | 185 | | | | | 190 | | |

| Leu | Asp | Gly | Leu | Leu | Xaa | Cys | Asn | Ser | Glu | Asp | Leu | Glu | Gly | Asp | Gly |
|---|---|---|---|---|---|---|---|---|---|---|---|---|---|---|---|
| | | | 195 | | | | | 200 | | | | | 205 | | |

| Ala | Met | Xaa | Leu | Leu | Gln | Glu | Arg | Leu | Gln | Ile | Lys | Pro | Ile | Ala | Leu |
|---|---|---|---|---|---|---|---|---|---|---|---|---|---|---|---|
| | | 210 | | | | | 215 | | | | | 220 | | | |

| Glu | Lys | Phe | Ser | Val | Pro | Asp | Phe | Pro | Asp | Lys | Gln | Xaa | Xaa | Asp | Leu |
|---|---|---|---|---|---|---|---|---|---|---|---|---|---|---|---|
| 225 | | | | | 230 | | | | | 235 | | | | | 240 |

| Lys | Ser | Leu | Gln | Gly | Asn | Lys | Ser | Lys | Pro | Arg | Lys | Ala | Leu | Ser | Asp |
|---|---|---|---|---|---|---|---|---|---|---|---|---|---|---|---|
| | | | | 245 | | | | | 250 | | | | | 255 | |

| Ile | Asp | Asn | Leu | Leu | Lys | Gly | Met | Asn | Xaa | Lys | Lys | Thr | Pro | Leu | Lys |
|---|---|---|---|---|---|---|---|---|---|---|---|---|---|---|---|
| | | | 260 | | | | | 265 | | | | | 270 | | |

| Arg | Xaa | Val | Gln | Cys | Pro | Val | Gln | Gln | Leu | Ala | Ser | Pro | Thr | Pro | Pro |
|---|---|---|---|---|---|---|---|---|---|---|---|---|---|---|---|
| | 275 | | | | | 280 | | | | | 285 | | | | |

| Arg | Ser | Pro | Phe | Ala | Ser | Leu | Leu | Ser | Leu | Gln | Lys | His | Ile | Ser | Arg |
|---|---|---|---|---|---|---|---|---|---|---|---|---|---|---|---|
| | 290 | | | | | 295 | | | | | 300 | | | | |

| Ser | Lys | Gln | Ser | Val | Asp | Pro | Phe | Ser | Xaa | His | Glu | Ile | Asp | His | Xaa |
|---|---|---|---|---|---|---|---|---|---|---|---|---|---|---|---|
| 305 | | | | | 310 | | | | | 315 | | | | | 320 |

| Ser | Xaa | Lys | Asn | Tyr | Ser | Pro | Thr | His | Met | Val | Asn | Pro | Glu | Xaa | Asn |
|---|---|---|---|---|---|---|---|---|---|---|---|---|---|---|---|
| | | | | 325 | | | | | 330 | | | | | 335 | |

| Leu | Val | Gly | Ser | Xaa | Xaa | Leu | Ser | Asn | Glu | Leu | Asn | Ala | Xaa | Met | Ile |
|---|---|---|---|---|---|---|---|---|---|---|---|---|---|---|---|
| | | | 340 | | | | | 345 | | | | | 350 | | |

| Glu | Asp | Val | Ile | Ala | Xaa | Gly | Lys | Thr | Ser | Leu | Asp | Thr | Asp | Arg | Asn |
|---|---|---|---|---|---|---|---|---|---|---|---|---|---|---|---|
| | | | 355 | | | | | 360 | | | | | 365 | | |

| Gly | Thr | Ser | Thr | Ser | Glu | Ile | Pro | Arg | Phe | Asp | Val | Ser | Asn | Glu | Pro |

```
                    370                 375                 380
His Asp Ile Asn Thr His Thr Ser Glu Ile Ser Lys Glu Asp Asn Ser
385                 390                 395                 400

Gly Lys Ser Ser Asn Asn Leu Asn Val Xaa Xaa Ile Glu Asp Ile Xaa
                405                 410                 415

Ala Val Gly Thr Ser Leu Ala Glu Asp Xaa Ala Arg Asn Cys Thr Ser
            420                 425                 430

Thr Pro Gln Lys Ser Met Val Asp Asn Ser Arg Glu Pro Arg Phe Asp
        435                 440                 445

Ala Asn Val Asp Ser Asn Glu Pro Val Xaa Met Asp Val Asp Ile Gly
    450                 455                 460

Gly Ile Ser Gly Met Gly Lys Arg Val Met Asp Thr Glu Xaa Arg
465                 470                 475                 480

Gln Asn Ile Glu Pro Asn Glu Xaa Cys Gln Ser Glu Asp Lys Thr Asn
                485                 490                 495

Met Gln Thr Phe Thr Ala Ser Ile Pro Thr Asp Asp Thr Asn Leu Asn
            500                 505                 510

Val Val Pro Leu Ala Asp Gln Ser Asn Pro Xaa Gly Tyr Gln Ala Ser
        515                 520                 525

Ser Val Asp Lys Arg Xaa Arg Arg Ser Asp Asp Gly Pro Glu His Gln
    530                 535                 540

Cys Leu Gln Glu Lys Thr Asp Gly Ser Met Ala Pro Val Asn Gly Gln
545                 550                 555                 560

Lys Arg Val Lys Ser Arg Val Lys Ser Lys Xaa Lys Lys Leu Ser Arg
                565                 570                 575

Lys Ser Leu Ala Asp Ala Gly Thr Ser Trp Xaa Ser Gly Leu Arg Arg
            580                 585                 590

Ser Thr Arg Ile Arg Thr Arg Pro Leu Glu Tyr Trp Lys Gly Glu Arg
        595                 600                 605

Xaa Val Tyr Gly Arg Val His Gln Ser Leu Ala Thr Val Ile Gly Val
    610                 615                 620

Lys Cys Met Ser Pro Gly Ser Asp Gly Lys Pro Thr Met Lys Val Lys
625                 630                 635                 640

Ser Tyr Val Ser Asp Lys Tyr Lys Glu Leu Phe Glu Leu Ala Ser Leu
                645                 650                 655

Tyr

<210> SEQ ID NO 18
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Any naturally occurring amino acid
<220> FEATURE:
<221> NAME/KEY: MOD_RES
<222> LOCATION: (110)..(110)
<223> OTHER INFORMATION: Any naturally occurring amino acid
<220> FEATURE:
<221> NAME/KEY: MOD_RES
<222> LOCATION: (128)..(128)
<223> OTHER INFORMATION: Any naturally occurring amino acid
<220> FEATURE:
<221> NAME/KEY: MOD_RES
<222> LOCATION: (133)..(133)
<223> OTHER INFORMATION: Any naturally occurring amino acid
```

-continued

```
<220> FEATURE:
<221> NAME/KEY: MOD_RES
<222> LOCATION: (144)..(144)
<223> OTHER INFORMATION: Any naturally occurring amino acid
<220> FEATURE:
<221> NAME/KEY: MOD_RES
<222> LOCATION: (153)..(153)
<223> OTHER INFORMATION: Any naturally occurring amino acid
<220> FEATURE:
<221> NAME/KEY: MOD_RES
<222> LOCATION: (192)..(192)
<223> OTHER INFORMATION: Any naturally occurring amino acid
<220> FEATURE:
<221> NAME/KEY: MOD_RES
<222> LOCATION: (197)..(197)
<223> OTHER INFORMATION: Any naturally occurring amino acid
<220> FEATURE:
<221> NAME/KEY: MOD_RES
<222> LOCATION: (220)..(220)
<223> OTHER INFORMATION: Any naturally occurring amino acid
<220> FEATURE:
<221> NAME/KEY: MOD_RES
<222> LOCATION: (242)..(242)
<223> OTHER INFORMATION: Any naturally occurring amino acid
<220> FEATURE:
<221> NAME/KEY: MOD_RES
<222> LOCATION: (246)..(246)
<223> OTHER INFORMATION: Any naturally occurring amino acid
<220> FEATURE:
<221> NAME/KEY: MOD_RES
<222> LOCATION: (249)..(249)
<223> OTHER INFORMATION: Any naturally occurring amino acid
<220> FEATURE:
<221> NAME/KEY: MOD_RES
<222> LOCATION: (265)..(265)
<223> OTHER INFORMATION: Any naturally occurring amino acid
<220> FEATURE:
<221> NAME/KEY: MOD_RES
<222> LOCATION: (286)..(286)
<223> OTHER INFORMATION: Any naturally occurring amino acid
<220> FEATURE:
<221> NAME/KEY: MOD_RES
<222> LOCATION: (295)..(295)
<223> OTHER INFORMATION: Any naturally occurring amino acid
<220> FEATURE:
<221> NAME/KEY: MOD_RES
<222> LOCATION: (299)..(299)
<223> OTHER INFORMATION: Any naturally occurring amino acid
<220> FEATURE:
<221> NAME/KEY: MOD_RES
<222> LOCATION: (311)..(311)
<223> OTHER INFORMATION: Any naturally occurring amino acid
<220> FEATURE:
<221> NAME/KEY: MOD_RES
<222> LOCATION: (328)..(328)
<223> OTHER INFORMATION: Any naturally occurring amino acid
<220> FEATURE:
<221> NAME/KEY: MOD_RES
<222> LOCATION: (349)..(349)
<223> OTHER INFORMATION: Any naturally occurring amino acid
<220> FEATURE:
<221> NAME/KEY: MOD_RES
<222> LOCATION: (379)..(379)
<223> OTHER INFORMATION: Any naturally occurring amino acid
<220> FEATURE:
<221> NAME/KEY: MOD_RES
<222> LOCATION: (416)..(416)
<223> OTHER INFORMATION: Any naturally occurring amino acid
<220> FEATURE:
<221> NAME/KEY: MOD_RES
<222> LOCATION: (423)..(423)
<223> OTHER INFORMATION: Any naturally occurring amino acid
<220> FEATURE:
<221> NAME/KEY: MOD_RES
<222> LOCATION: (439)..(439)
<223> OTHER INFORMATION: Any naturally occurring amino acid
<220> FEATURE:
<221> NAME/KEY: MOD_RES
<222> LOCATION: (488)..(488)
```

```
<223> OTHER INFORMATION: Any naturally occurring amino acid
<220> FEATURE:
<221> NAME/KEY: MOD_RES
<222> LOCATION: (503)..(503)
<223> OTHER INFORMATION: Any naturally occurring amino acid
<220> FEATURE:
<221> NAME/KEY: MOD_RES
<222> LOCATION: (526)..(526)
<223> OTHER INFORMATION: Any naturally occurring amino acid
<220> FEATURE:
<221> NAME/KEY: MOD_RES
<222> LOCATION: (533)..(533)
<223> OTHER INFORMATION: Any naturally occurring amino acid
<220> FEATURE:
<221> NAME/KEY: MOD_RES
<222> LOCATION: (580)..(580)
<223> OTHER INFORMATION: Any naturally occurring amino acid
<220> FEATURE:
<221> NAME/KEY: MOD_RES
<222> LOCATION: (611)..(611)
<223> OTHER INFORMATION: Any naturally occurring amino acid
<220> FEATURE:
<221> NAME/KEY: MOD_RES
<222> LOCATION: (649)..(649)
<223> OTHER INFORMATION: Any naturally occurring amino acid
<220> FEATURE:
<221> NAME/KEY: MOD_RES
<222> LOCATION: (692)..(692)
<223> OTHER INFORMATION: Any naturally occurring amino acid

<400> SEQUENCE: 18

Met Asp Ala Ala Asp Pro Leu Xaa Ala Ile Ser Ser Pro Ala Arg Leu
1               5                   10                  15

Leu Pro Arg Thr Leu Gly Pro Ala Ala Ser Pro Ser Lys Ala Arg
            20                  25                  30

Glu Ala Leu Leu Glu Ala Ile Ser Arg Leu Lys Gly Ser Lys Glu Leu
        35                  40                  45

Val Glu Gln Ala Arg Met Val Leu Lys Glu His Gly Asp Ile Gln Lys
50                  55                  60

Leu Tyr His Asp Asp Gly Val Lys Ala Pro Ala Asn Gly Ser Lys Asn
65                  70                  75                  80

Gln Gln Gly Arg Arg Pro Ala Leu Asp Arg Lys Arg Ala Arg Phe Thr
                85                  90                  95

Met Lys Asp Thr Ala Ser Lys Pro Val Pro Val Val Asp Xaa Ser Lys
            100                 105                 110

Leu Leu Asn Ile Ser Asp Pro Glu Glu Tyr Phe Met Thr Leu Asp Xaa
        115                 120                 125

Leu Glu Glu Ala Xaa Lys Glu Ile Lys Arg Leu Asn Gly Glu Val Xaa
130                 135                 140

Lys Ala Val Leu Asn Phe Asp Pro Xaa Asp Pro Lys Arg Arg Pro
145                 150                 155                 160

Gly Leu Leu Gly Arg Lys Ser Val Arg Ser Phe Lys Phe Ile Asp Ala
                165                 170                 175

Asp Thr Gln Asp Pro Ile Glu Val Pro Ala Ser Gln Thr Glu Thr Xaa
            180                 185                 190

Thr Gly Ser Gln Xaa Ser Gln Asp Asp Met His Ala Ser Val Ala Glu
        195                 200                 205

Lys Asn Glu Gln Ser Val Pro Ser Ser Ser Xaa Ala Ile Ser Asp
210                 215                 220

Val Ser Gly Lys Glu Asp Ser Leu Ala Glu Lys Asp Gly Arg Asp Asp
225                 230                 235                 240

Leu Xaa Tyr Leu Leu Xaa Ser Leu Xaa Asn Leu Asp Glu Ser Glu Glu
        245                 250                 255
```

-continued

```
Glu Asn Phe Leu Arg Lys Thr Leu Xaa Ile Lys Glu Ile Arg Lys Ile
                260                 265                 270

Glu Lys Val Cys Leu Pro Asn Ser Ile Pro Gly Asp Arg Xaa Leu Arg
            275                 280                 285

Ser Asn Thr Glu Gln Lys Xaa Ser Met Arg Xaa His Pro Pro Glu Ser
290                 295                 300

Leu Pro Gln Ser His Gln Xaa Arg Ile Ser Glu Leu Glu Lys His Leu
305                 310                 315                 320

Phe Pro Gly Asp Ala Ala Asn Xaa Lys Cys Thr Asp Leu Glu Asp Asp
                325                 330                 335

Glu Ser Glu Gly Ser Pro Asp Ile Val Met Gly Glu Xaa Ser Leu Val
            340                 345                 350

His Asp Ser Ser Asp Val Leu Met Thr Asp Glu Ala Asn Thr Ala Ser
        355                 360                 365

Glu Ile Asp Arg Glu Thr Pro Asn Leu Gly Xaa Lys Ala Ala Asp His
370                 375                 380

Val Leu Asp Pro Glu Pro Asn Asp His Ala Tyr Glu Arg Gln Pro Gly
385                 390                 395                 400

Ser Ser Leu Gly Leu Asp Thr Glu Val Ala Lys Glu Lys Glu Ala Xaa
                405                 410                 415

Ser Arg Ser Asn Ile Ser Xaa Glu Glu Asp Asp Val Pro Ile Asp Tyr
            420                 425                 430

Pro Thr Gly Arg Ser Asn Xaa Glu Thr Glu Val Ser Ser Pro His His
        435                 440                 445

Leu Glu Gly Ser Ser Thr Glu Val Leu Ser Ser Thr Pro Gly Arg Asn
    450                 455                 460

Ala Ser Pro Asp Gly Ile Asp Arg Thr Ser His Thr Ala Glu Asp Ser
465                 470                 475                 480

Ile Gln His Leu Glu Ala Val Xaa Glu Asp Gly Val Lys Gln Asp Lys
                485                 490                 495

Ser Ser Gln Pro Ser Glu Xaa Pro Leu Glu Asp Ile Asp Pro Gln Asn
            500                 505                 510

Gln Ser Gln Met His Gly Gly Ser Thr Lys Lys Leu Ala Xaa Asp Ser
        515                 520                 525

Asn Ala Leu Ser Xaa Ser Lys Gln Lys Lys Gln Gln Ala Ala Gln Glu
    530                 535                 540

Gly Lys Met Lys Lys Gln Ser Lys Arg Gly Lys Lys Val Ala Asp Glu
545                 550                 555                 560

Ser Ser Pro Leu Glu Ile Pro Gln Asn Phe Asp Ser Glu Asn Gln Pro
                565                 570                 575

His Asn Asp Xaa Asn Ile Glu Gln Gln His Thr Val Thr Ser Ser Pro
            580                 585                 590

Leu Ser Pro Asn Lys Gly Lys Gly Gln Lys Gly Ala Gln Arg Arg Asn
        595                 600                 605

Lys Thr Xaa Lys Leu Asn Gln Arg Lys Ser Leu Gly Asp Ala Gly Leu
    610                 615                 620

Ala Trp Gln Ser Gly Val Arg Arg Ser Thr Arg Ile Arg Ser Arg Pro
625                 630                 635                 640

Leu Glu His Trp Leu Gly Glu Arg Xaa Leu Tyr Gly Arg Ile His Asp
                645                 650                 655

Thr Met Ala Val Ile Gly Ile Lys Ser Tyr Ser Pro Ser Gln Asp Gly
            660                 665                 670
```

Lys Lys Thr Leu Lys Val Lys Ser Phe Val Pro Asp Gln Tyr Ser Asp
        675                 680                 685

Leu Val Ala Xaa Ser Ala Lys Tyr
    690                 695

<210> SEQ ID NO 19
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (73)..(73)
<223> OTHER INFORMATION: Any naturally occurring amino acid
<220> FEATURE:
<221> NAME/KEY: MOD_RES
<222> LOCATION: (118)..(118)
<223> OTHER INFORMATION: Any naturally occurring amino acid
<220> FEATURE:
<221> NAME/KEY: MOD_RES
<222> LOCATION: (150)..(150)
<223> OTHER INFORMATION: Any naturally occurring amino acid
<220> FEATURE:
<221> NAME/KEY: MOD_RES
<222> LOCATION: (170)..(170)
<223> OTHER INFORMATION: Any naturally occurring amino acid
<220> FEATURE:
<221> NAME/KEY: MOD_RES
<222> LOCATION: (185)..(185)
<223> OTHER INFORMATION: Any naturally occurring amino acid
<220> FEATURE:
<221> NAME/KEY: MOD_RES
<222> LOCATION: (197)..(197)
<223> OTHER INFORMATION: Any naturally occurring amino acid
<220> FEATURE:
<221> NAME/KEY: MOD_RES
<222> LOCATION: (199)..(199)
<223> OTHER INFORMATION: Any naturally occurring amino acid
<220> FEATURE:
<221> NAME/KEY: MOD_RES
<222> LOCATION: (211)..(211)
<223> OTHER INFORMATION: Any naturally occurring amino acid
<220> FEATURE:
<221> NAME/KEY: MOD_RES
<222> LOCATION: (219)..(219)
<223> OTHER INFORMATION: Any naturally occurring amino acid
<220> FEATURE:
<221> NAME/KEY: MOD_RES
<222> LOCATION: (221)..(221)
<223> OTHER INFORMATION: Any naturally occurring amino acid
<220> FEATURE:
<221> NAME/KEY: MOD_RES
<222> LOCATION: (233)..(233)
<223> OTHER INFORMATION: Any naturally occurring amino acid
<220> FEATURE:
<221> NAME/KEY: MOD_RES
<222> LOCATION: (241)..(241)
<223> OTHER INFORMATION: Any naturally occurring amino acid
<220> FEATURE:
<221> NAME/KEY: MOD_RES
<222> LOCATION: (269)..(269)
<223> OTHER INFORMATION: Any naturally occurring amino acid
<220> FEATURE:
<221> NAME/KEY: MOD_RES
<222> LOCATION: (274)..(274)
<223> OTHER INFORMATION: Any naturally occurring amino acid
<220> FEATURE:
<221> NAME/KEY: MOD_RES
<222> LOCATION: (319)..(319)
<223> OTHER INFORMATION: Any naturally occurring amino acid
<220> FEATURE:
<221> NAME/KEY: MOD_RES
<222> LOCATION: (321)..(321)
<223> OTHER INFORMATION: Any naturally occurring amino acid
<220> FEATURE:

```
<221> NAME/KEY: MOD_RES
<222> LOCATION: (339)..(339)
<223> OTHER INFORMATION: Any naturally occurring amino acid
<220> FEATURE:
<221> NAME/KEY: MOD_RES
<222> LOCATION: (369)..(369)
<223> OTHER INFORMATION: Any naturally occurring amino acid
<220> FEATURE:
<221> NAME/KEY: MOD_RES
<222> LOCATION: (370)..(370)
<223> OTHER INFORMATION: Any naturally occurring amino acid
<220> FEATURE:
<221> NAME/KEY: MOD_RES
<222> LOCATION: (375)..(375)
<223> OTHER INFORMATION: Any naturally occurring amino acid
<220> FEATURE:
<221> NAME/KEY: MOD_RES
<222> LOCATION: (383)..(383)
<223> OTHER INFORMATION: Any naturally occurring amino acid
<220> FEATURE:
<221> NAME/KEY: MOD_RES
<222> LOCATION: (420)..(420)
<223> OTHER INFORMATION: Any naturally occurring amino acid
<220> FEATURE:
<221> NAME/KEY: MOD_RES
<222> LOCATION: (450)..(450)
<223> OTHER INFORMATION: Any naturally occurring amino acid
<220> FEATURE:
<221> NAME/KEY: MOD_RES
<222> LOCATION: (451)..(451)
<223> OTHER INFORMATION: Any naturally occurring amino acid
<220> FEATURE:
<221> NAME/KEY: MOD_RES
<222> LOCATION: (456)..(456)
<223> OTHER INFORMATION: Any naturally occurring amino acid
<220> FEATURE:
<221> NAME/KEY: MOD_RES
<222> LOCATION: (458)..(458)
<223> OTHER INFORMATION: Any naturally occurring amino acid
<220> FEATURE:
<221> NAME/KEY: MOD_RES
<222> LOCATION: (459)..(459)
<223> OTHER INFORMATION: Any naturally occurring amino acid
<220> FEATURE:
<221> NAME/KEY: MOD_RES
<222> LOCATION: (467)..(467)
<223> OTHER INFORMATION: Any naturally occurring amino acid
<220> FEATURE:
<221> NAME/KEY: MOD_RES
<222> LOCATION: (472)..(472)
<223> OTHER INFORMATION: Any naturally occurring amino acid
<220> FEATURE:
<221> NAME/KEY: MOD_RES
<222> LOCATION: (476)..(476)
<223> OTHER INFORMATION: Any naturally occurring amino acid
<220> FEATURE:
<221> NAME/KEY: MOD_RES
<222> LOCATION: (482)..(482)
<223> OTHER INFORMATION: Any naturally occurring amino acid
<220> FEATURE:
<221> NAME/KEY: MOD_RES
<222> LOCATION: (496)..(496)
<223> OTHER INFORMATION: Any naturally occurring amino acid
<220> FEATURE:
<221> NAME/KEY: MOD_RES
<222> LOCATION: (508)..(508)
<223> OTHER INFORMATION: Any naturally occurring amino acid
<220> FEATURE:
<221> NAME/KEY: MOD_RES
<222> LOCATION: (519)..(519)
<223> OTHER INFORMATION: Any naturally occurring amino acid
<220> FEATURE:
<221> NAME/KEY: MOD_RES
<222> LOCATION: (520)..(520)
<223> OTHER INFORMATION: Any naturally occurring amino acid
<220> FEATURE:
<221> NAME/KEY: MOD_RES
<222> LOCATION: (526)..(526)
<223> OTHER INFORMATION: Any naturally occurring amino acid
```

```
<220> FEATURE:
<221> NAME/KEY: MOD_RES
<222> LOCATION: (536)..(536)
<223> OTHER INFORMATION: Any naturally occurring amino acid
<220> FEATURE:
<221> NAME/KEY: MOD_RES
<222> LOCATION: (538)..(538)
<223> OTHER INFORMATION: Any naturally occurring amino acid
<220> FEATURE:
<221> NAME/KEY: MOD_RES
<222> LOCATION: (542)..(542)
<223> OTHER INFORMATION: Any naturally occurring amino acid
<220> FEATURE:
<221> NAME/KEY: MOD_RES
<222> LOCATION: (549)..(549)
<223> OTHER INFORMATION: Any naturally occurring amino acid
<220> FEATURE:
<221> NAME/KEY: MOD_RES
<222> LOCATION: (553)..(553)
<223> OTHER INFORMATION: Any naturally occurring amino acid
<220> FEATURE:
<221> NAME/KEY: MOD_RES
<222> LOCATION: (574)..(574)
<223> OTHER INFORMATION: Any naturally occurring amino acid
<220> FEATURE:
<221> NAME/KEY: MOD_RES
<222> LOCATION: (579)..(579)
<223> OTHER INFORMATION: Any naturally occurring amino acid
<220> FEATURE:
<221> NAME/KEY: MOD_RES
<222> LOCATION: (585)..(585)
<223> OTHER INFORMATION: Any naturally occurring amino acid
<220> FEATURE:
<221> NAME/KEY: MOD_RES
<222> LOCATION: (589)..(589)
<223> OTHER INFORMATION: Any naturally occurring amino acid
<220> FEATURE:
<221> NAME/KEY: MOD_RES
<222> LOCATION: (615)..(615)
<223> OTHER INFORMATION: Any naturally occurring amino acid
<220> FEATURE:
<221> NAME/KEY: MOD_RES
<222> LOCATION: (633)..(633)
<223> OTHER INFORMATION: Any naturally occurring amino acid
<220> FEATURE:
<221> NAME/KEY: MOD_RES
<222> LOCATION: (650)..(650)
<223> OTHER INFORMATION: Any naturally occurring amino acid
<220> FEATURE:
<221> NAME/KEY: MOD_RES
<222> LOCATION: (657)..(657)
<223> OTHER INFORMATION: Any naturally occurring amino acid
<220> FEATURE:
<221> NAME/KEY: MOD_RES
<222> LOCATION: (661)..(661)
<223> OTHER INFORMATION: Any naturally occurring amino acid
<220> FEATURE:
<221> NAME/KEY: MOD_RES
<222> LOCATION: (663)..(663)
<223> OTHER INFORMATION: Any naturally occurring amino acid
<220> FEATURE:
<221> NAME/KEY: MOD_RES
<222> LOCATION: (705)..(705)
<223> OTHER INFORMATION: Any naturally occurring amino acid
<220> FEATURE:
<221> NAME/KEY: MOD_RES
<222> LOCATION: (710)..(710)
<223> OTHER INFORMATION: Any naturally occurring amino acid
<220> FEATURE:
<221> NAME/KEY: MOD_RES
<222> LOCATION: (716)..(716)
<223> OTHER INFORMATION: Any naturally occurring amino acid
<220> FEATURE:
<221> NAME/KEY: MOD_RES
<222> LOCATION: (722)..(722)
<223> OTHER INFORMATION: Any naturally occurring amino acid

<400> SEQUENCE: 19
```

```
Met Asn Trp Ser Ser Asp Pro Val Asp Pro Leu Gln Gly Phe Thr Gly
1               5                   10                  15
Leu Ala Phe Lys Pro Leu Asn Thr Ala Ser Gln Val Lys Leu Val Asp
            20                  25                  30
Gln Val Lys Asn Ile Leu Ser Asp Thr Ser Lys Thr Leu Lys Ser Gly
        35                  40                  45
Asn Pro Gln Ala Thr Lys Gln Lys Ser Glu Gly Pro Glu Lys Ala Ser
    50                  55                  60
Gln Pro Asn Met Ser Leu Leu Pro Xaa Asp Ile Asn Gly Leu Glu Ala
65                  70                  75                  80
Arg Lys Glu Asn Phe Arg Gly Asp Ala Ala Leu Ala Asp Gln Gln Ala
                85                  90                  95
Ile His Ile Arg Leu Lys Ser Met Ala Ser Gln His Ser Pro Ser Lys
            100                 105                 110
Leu Lys Asp Gln Ala Xaa Asn Ile Val Ser Gly Thr Ser Glu Ile Leu
        115                 120                 125
Glu Pro Gly Asn Arg Gln Ala Leu Lys Gln Lys Asn Lys Val Val Pro
    130                 135                 140
Glu Lys Ala Val Glu Xaa Pro Arg Gln Arg Pro Ala Leu Gly Leu
145                 150                 155                 160
Lys Arg Ala Arg Phe Ser Met Lys Pro Xaa Ser Ser Gln Pro Asp Thr
                165                 170                 175
Ser Leu Leu Pro Pro Phe Asp Ala Xaa Lys Tyr Thr Asp Pro Glu Glu
            180                 185                 190
Leu Phe Lys Glu Xaa Glu Xaa Tyr Glu Asn Ala Lys Lys Glu Leu Glu
        195                 200                 205
Lys Gln Xaa Gly Gly Ala Ile Leu Asp Ala Xaa Lys Xaa Asn Pro Ser
    210                 215                 220
Pro Ile Lys Arg Thr Arg Arg Pro Xaa Ile Leu Arg Lys Arg Ala Lys
225                 230                 235                 240
Xaa Lys His Ser Tyr Pro Leu Met Asp Phe Glu Ser Ser Glu Asn Gly
                245                 250                 255
Gln Glu Thr Ser Ile Ser Pro Leu Asn His Ser Thr Xaa Ile Glu Pro
            260                 265                 270
Asn Xaa Asn Val Ala Leu Glu Glu Met Asp Leu Ala Gly Ser Leu Ala
        275                 280                 285
Glu Lys Glu Val Asn Gly Asp Ile Leu Phe Asp Glu Leu Leu Ser Leu
    290                 295                 300
Asn Thr Glu Cys Glu Leu Glu Gly Asp Gly Ala Val Thr His Xaa Gln
305                 310                 315                 320
Xaa Cys Leu Arg Met Lys Pro Ile Glu Pro Glu Lys Ser Asp Leu Pro
                325                 330                 335
Glu Phe Xaa Ser Ile Asp Ser Ser Arg Arg Thr Leu Pro Lys Gly Asp
            340                 345                 350
Cys Leu Thr Asp Ile Asp Asn Leu Leu Lys Gly Leu Ile Ser Ser Thr
        355                 360                 365
Xaa Xaa Lys His Arg Lys Xaa Gly Ala Glu Gly Ser Ile His Xaa Ala
    370                 375                 380
Ser Pro Thr Pro Pro Lys Ser Pro Phe Ala Ser Ile Leu Asp Leu His
385                 390                 395                 400
Lys Arg Ile Leu His Ser Ser Pro Ser Ser Asp Pro Phe Ser Ala His
                405                 410                 415
Asp Ile Asp Xaa Phe Leu Pro Glu Thr Asn Pro Ser Ser Val Glu Asn
```

-continued

```
                420             425             430
Arg Asn Lys Gln Ser Glu Leu Val Asp Met Arg Glu Gln Ile Thr Val
        435             440             445

Ser Xaa Xaa Leu Lys Ser Pro Xaa Ile Xaa Xaa Asn Asp Asn Ile Glu
        450             455             460

Val Ala Xaa Gly Gly Ser Ser Xaa Val Asp Ile Xaa Glu Phe Ser Tyr
465             470             475             480

Ala Xaa Lys Arg Ser Val Ser Glu Asp Ser Ser Lys His Gly Asp Xaa
            485             490             495

Arg Ile Asp Val Gly Ser Ser Gly Ser His Val Xaa Leu Glu Asp Asn
            500             505             510

Ile Gly Gly Ser Asn Met Xaa Xaa Arg Val Ile Asn Asp Xaa Ser His
        515             520             525

Ser Pro Gly Ala Asp Thr Asp Xaa Trp Xaa Asn Gly Asp Xaa Gly Asp
        530             535             540

Asn Asp Gly Asp Xaa Ile Val Glu Xaa Glu His Glu Glu Ala Val Ala
545             550             555             560

Ser Ala Glu Pro Glu Leu Asn Val Ala Asp Ser Thr Leu Xaa Lys Ala
            565             570             575

Asn Gly Xaa Thr Leu Asn Asp Asn Xaa His Pro Asp Xaa Asp Glu Thr
            580             585             590

Asp Leu Asn Arg Asp Asn Val Ala Asn Asp Gly Asp Glu Thr Gln Val
        595             600             605

Glu Asp Lys His Glu Glu Xaa Leu Ala Ser Glu Glu Pro Glu Leu Asn
        610             615             620

Val Ala Asp Ser Thr Leu Glu Asn Xaa Ser Ser Ala Leu Asn Glu Asn
625             630             635             640

Ile Gln Ile Lys Ala Asn Ser Arg Pro Xaa Ile Arg Lys Arg Lys Ser
            645             650             655

Xaa Glu Val Ser Xaa Arg Xaa Ser Leu Ala Gly Ala Gly Thr Thr Trp
            660             665             670

Gln Ser Gly Val Arg Arg Ser Thr Arg Ile Lys Thr Arg Pro Leu Glu
        675             680             685

Tyr Trp Lys Gly Glu Arg Leu Leu Tyr Gly Arg Ile His Asp Ser Leu
        690             695             700

Xaa Thr Val Ile Gly Xaa Lys Tyr Ala Ser Pro Xaa Lys Gly Asp Asn
705             710             715             720

Gly Xaa Gly Pro Leu Lys Val Lys Ser Phe Val Ser Asp Glu Tyr Lys
            725             730             735

Glu Leu Val Glu Leu Ala Ala Leu His
        740             745
```